US008906874B2

(12) United States Patent
Rao et al.

(10) Patent No.: US 8,906,874 B2
(45) Date of Patent: Dec. 9, 2014

(54) BI-FUNCTIONAL SHRNA TARGETING STATHMIN 1 AND USES THEREOF

(75) Inventors: Donald Rao, Dallas, TX (US); John J. Nemunaitis, Dallas, TX (US); Neil Senzer, Dallas, TX (US)

(73) Assignee: Gradalis, Inc., Carrollton, TX (US)

( * ) Notice: Subject to any disclaimer, the term of this patent is extended or adjusted under 35 U.S.C. 154(b) by 73 days.

(21) Appl. No.: 13/410,130

(22) Filed: Mar. 1, 2012

(65) Prior Publication Data

US 2012/0251617 A1  Oct. 4, 2012

Related U.S. Application Data

(63) Continuation-in-part of application No. 13/364,053, filed on Feb. 1, 2012, now Pat. No. 8,758,998, which is a continuation-in-part of application No. 11/983,482, filed on Nov. 9, 2007, now Pat. No. 8,252,526, and a continuation-in-part of application No. 11/601,431, filed on Nov. 17, 2006, now Pat. No. 8,603,991.

(60) Provisional application No. 60/932,653, filed on Jun. 1, 2007, provisional application No. 60/897,214, filed on Jan. 24, 2007, provisional application No. 60/857,846, filed on Nov. 9, 2006.

(51) Int. Cl.
*A01N 43/04* (2006.01)
*A61K 48/00* (2006.01)
*C07H 21/04* (2006.01)

(52) U.S. Cl.
USPC ........ 514/44; 435/6.1; 435/91.41; 435/91.51; 536/23.1; 536/24.5

(58) Field of Classification Search
USPC .................. 435/6, 91.1, 91.31, 455, 6.1, 458, 435/91.41, 91.51; 514/44, 1, 2; 536/23.1, 536/24.5, 24.3
See application file for complete search history.

(56) References Cited

U.S. PATENT DOCUMENTS

| 6,506,559 | B1 | 1/2003 | Fire et al. |
| 7,615,618 | B2 | 11/2009 | Manoharan et al. |
| 7,763,722 | B2 | 7/2010 | Chang et al. |
| 8,252,526 | B2 | 8/2012 | Rao |
| 2003/0138407 | A1 | 7/2003 | Lu et al. |
| 2003/0148295 | A1 | 8/2003 | Wan et al. |
| 2004/0023390 | A1 | 2/2004 | Davidson et al. |
| 2004/0213764 | A1 | 10/2004 | Wold et al. |
| 2004/0241854 | A1 | 12/2004 | Davidson et al. |
| 2005/0043263 | A1 | 2/2005 | Giese et al. |
| 2005/0080031 | A1 | 4/2005 | McSwiggen |
| 2005/0142578 | A1 | 6/2005 | Usman et al. |
| 2005/0143333 | A1 | 6/2005 | Richards et al. |
| 2008/0269474 | A1 | 10/2008 | Rao |
| 2009/0004668 | A1 | 1/2009 | Chen et al. |
| 2009/0208514 | A1 | 8/2009 | Nakamura et al. |
| 2012/0183955 | A1 | 7/2012 | Rao |

FOREIGN PATENT DOCUMENTS

| WO | 02/44321 A2 | 6/2002 |
| WO | 0244321 A2 | 6/2002 |
| WO | 03006477 A1 | 1/2003 |

OTHER PUBLICATIONS

Opalinska et al., Nature Rev., vol. 1, pp. 503-514 (2002).*
Peracchi et al., Rev. Med. Virol., vol. 14, pp. 47-64 (2004).*
Crooke, S., Ann. Rev. Medicine, vol. 55, pp. 61-95 (2004).*
Chirila et al., Biomaterials, vol. 23, pp. 321-342 (2002).*
Agrawal et al., Molecular Med. Today, vol. 6, pp. 72-81 (2000).*
Agrawal, Sudhir, et al., "Antisense Therapeutics: Is it as Simple as Complementary Base Recognition?" Molecular Medicine Today, Feb. 2000, vol. 6, 12 pages.
Ameres, Stefan Ludwig, et al., "Molecular Vasis for Target RNA Recognition and Cleavage by Human RISC," Cell, Jul. 13, 2007, pp. 101-112.
Carette, Jan E., et al., "Conditionally Replicating Adenoviruses Expressing Short Hairpin RNAs Silence the Expression of a Target Gene in Cancer Cells," Cancer Research, Apr. 15, 2004, 64:2663-2667.
Chirila, Trajan V., et al., "The Use of Synthetic Polymers for Delivery of Therapeutic Antisense Oligodeoxynucleotides," Biomaterials, (2002), vol. 23, pp. 321-342.
Crooke, Stanley T., "Progress in Antisense Technology," Annu. Rev. Med., (2004), 55:61-95.
Davidson, Beverly L., et al., "Current Prospects for RNA Interference-Based Therapies," Nature Reviews Genetics, May 2011, vol. 12, pp. 329-340.
Drews, Jurgen, et al., "Drug Discovery: A Historical Perspective," Science, Mar. 17, 2000, vol. 287, pp. 1960-1964.
Fire, et al., "Nobel Lectures, The Nobel Prize in Physiology or Medicine 2006," Angew. Chem. Int. Ed., (2007), 46:6966-6984.
Giering, Jeffery C., et al., "Expression of shRNA From a Tissue-Specific Pol II Promoter is an Effective and Safe RNAi Therapeutic," www.moleculartherapy.org, Sep. 2008, vol. 16, No. 9, pp. 1630-1636.
Gregory, Richard I., et al., "Human RISC Couples MicroRNA Biogenesis and Posttrranscriptional Gene Silencing," Cell, Nov. 18, 2005, vol. 123, pp. 631-640.
Grimson, Andrew, et al., "MicroRNA Targeting Specificity in Mammals: Determinants Beyond Seed Pairing," Molecular Cell, Jul. 6, 2007, 27:91-105.
Jang, Jae-Hyung, et al., "Gene Delivery from Polymer Scaffolds for Tissue Engineering," Expert Rev. Medical Devices, (2004), 1(1):127-138.

(Continued)

*Primary Examiner* — Jane Zara
(74) *Attorney, Agent, or Firm* — Edwin S. Flores; Chalker Flores, LLp

(57) ABSTRACT

The present invention includes bifunctional shRNAs capable of reducing an expression of a Stathmin 1 gene; wherein at least one target site sequence of the bifunctional RNA molecule is located within the Stathmin 1 gene, wherein the bifunctional RNA molecule is capable of activating a cleavage-dependent and a cleavage-independent RNA-induced silencing complex for reducing the expression level of Stathmin 1.

33 Claims, 19 Drawing Sheets

(56) References Cited

OTHER PUBLICATIONS

Kim, Dong-Ho, et al., "Synthetic dsRNA Dicer Substrates Enhance RNAi Potency and Efficacy," Nature Biotechnology, Feb. 2005, vol. 23, No. 2, pp. 222-226.

Matranga, Christian, et al., "Passenger-Strand Cleavage Facilitates Assembly of siRNA into Ago2-Containing RNAi Enzyme Complexes," Cell, Nov. 15, 2005, vol. 123, pp. 607-620.

Mello, CC, "Return to the RNAi World: Rethinking Gene Expression and Evolution," Cell Death and Differentiation, (2007), 14:2013-2020.

Opalinska, Joanna B., et al., "Nucleic-Acid Therapeutics: Basic Principles and Recent Applications," Nature Reviews, Jul. 2002, vol. 1, pp. 503-514.

Paroo, Zain, et al., "Challenges for RNAi in vivo," Trends in Biotechnology, Aug. 2004, vol. 22, No. 8, pp. 390-394.

Peracchi, Alessio, "Prospects for Antiviral Ribozymes and Deoxyribozymes," Rev. Med. Virol., (2004), 14:47-64.

Petricoin, Emanuel F., et al., "Clinical Proteomics: Translating Benchside Promise into Bedside Reality," Nature Reviews—Drug Discovery, Sep. 2002, vol. 1, pp. 683-695.

Preall, Jonathan B., et al., "RNAi: RISC Gets Loaded," Cell, Nov. 18, 2005, vol. 123, pp. 543-553.

Rao, Donald D., et al., "siRNA vs. shRNA: Similarities and Differences," Advanced Drug Delivery Reviews, (2009), 61:746-759.

Rao, DD., et al., "Enhanced Target Gene Knockdown by a Bifunctional shRNA: A Novel Approach of RNA Interference," Cancer Gene Therapy, (2010), pp. 1-12.

Shen, Yuqiao, et al., Individualised Cancer Therapeutics: Dream or Reality? Therapeutics Construction, Expert Opin. Biol. Ther., (2005) 5(11):1427-1441.

Simari, Robert D., et al., "Requirements for Enhanced Transgene Expression by Untranslated Sequences from the Human Cytomegalovirus Immediate-Early Gene," Molecular Medicine, (1998), 4:700-706.

Siolas, Despina, et al., "Synthetic shRNAs as Potent RNAi Triggers," Nature Biotechnoloty, Feb. 2005, vol. 23, No. 2, pp. 227-231.

Verdine, Gregory L., et al., "The Challenge of Drugging Undruggable Targets in Cancer: Lessons Learned from Targeting BCL-2 Family Members," Clinical Cancer Res., (2007), 13:7264-7270.

Walton, S. Patrick, et al., "Designing Highly Active siRNAs for Therapeutic Applications," FEBS Journal, (2010) 277:4806-4813.

Welsh, John B., et al., "Analysis of Gene Expression Profiles in Normal and Neoplastic Ovarian Tissue Samples Identifies Candidate Molecular Markers of Epithelial Ovarian Cancer," PNAS, Jan. 30, 2001, vol. 98, No. 3, pp. 1176-1181.

Doench J., et al., "Specificity of MicroRNA Target Selection in Translational Repression", Genes Dev., 2004, 18, 504-511.

Nolen, T., "Positional Effects of Short Interfering RNAs Targeting the Human Coagulation Trigger Tissue Factor", Nucleic Acids Research, 2002, 30, 8, 1757-1766.

* cited by examiner

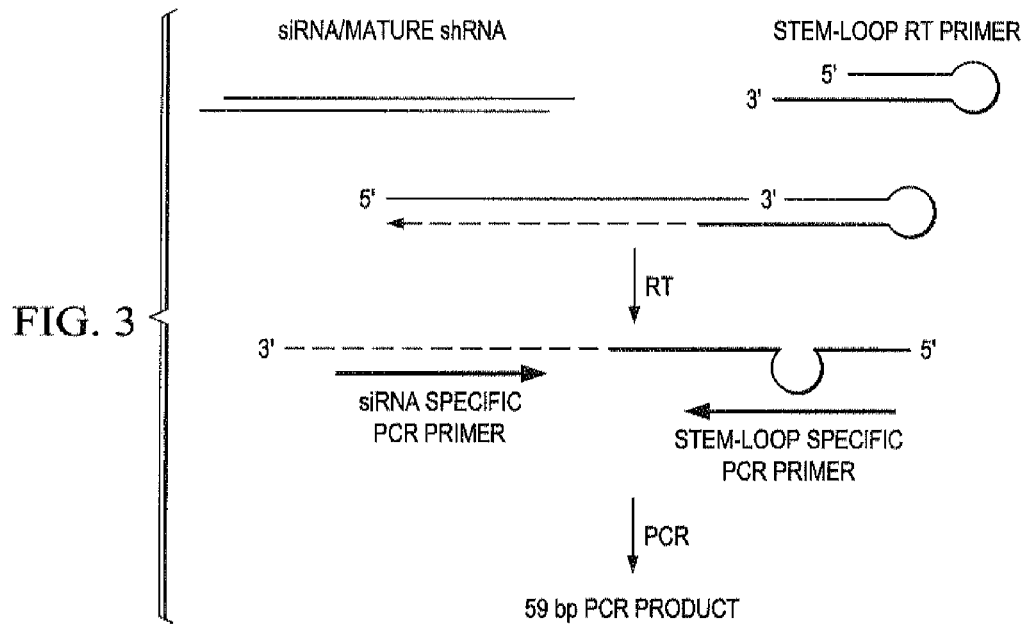
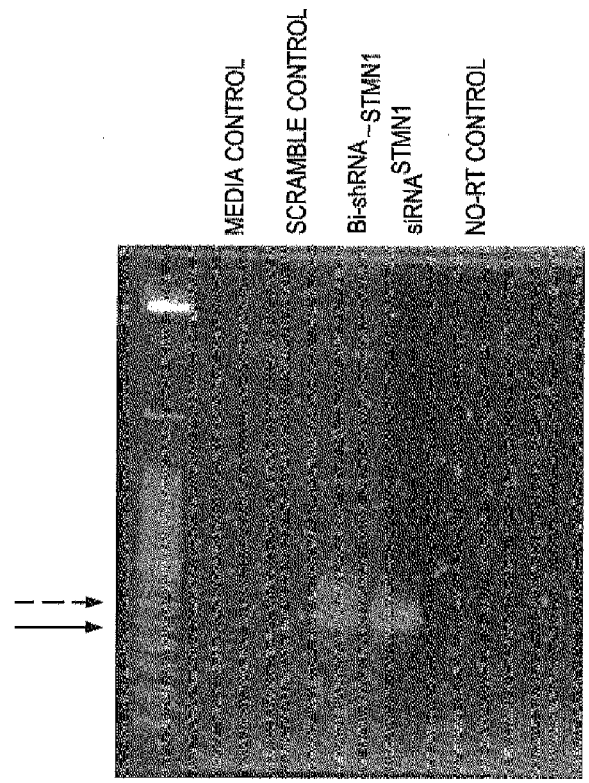
FIG. 4a

FIG. 8

| PLASMIDS | shRNA SEQUENCE | PREDICTED MECHANISM |
|---|---|---|
| pGBI-1<br>SEQ ID NO: 3 | ```
        G    GA   C       GUGAAG
GGAUCCU  GCU UUGA CAGU GCG GGCACAAAUGGCUGCCAAAUA
         ||| |||| |||| ||| ||||||||||||||||||||
         CGA GGCU GUCA CGU CCGUGUUUACCGACGGUUUAU
GUUU    A    CC   UC  U        GUAGAC
                                  CCA
``` | CLEAVAGE DEPENDENT |
| bi-sh-STMN1<br>SEQ ID NO: 4 | ```
        G    GA   C       GUGAAG
GGAUCCU GCU UUGA CAGU GCG GGCACAAAUGGCUGCCAAAUA
        ||| |||| |||| ||| ||||||||||||||||||||
        CGA GGCU GUCA CGU CCGUGUUUACCGACGGUUUAU
     GGCU   CC   UC  U       GUAGAC
                                CCA
            ACUCCU
        G    GA   C       AU    GUGAAG
        GCU UUGA CAGU GCG GGCACAAAUG UGCCAAAUA
        ||| |||| |||| ||| |||||||||| |||||||||
        CGA GGCU GUCA CGU CCGUGUUUAC ACGGUUUAU
            CC   UC  U    CG       GUAGAC
                                     CCA
``` | BI-FUNCTIONAL |
| pGBI-3<br>SEQ ID NO: 5 | ```
        G    GA   C       AU    GUGAAG
GGAUCCU GCU UUGA CAGU GCG GGCACAAAUG UGCCAAAUA
        ||| |||| |||| ||| |||||||||| |||||||||
        CGA GGCU GUCA CGU CCGUGUUUAC ACGGUUUAU
GUUU    A    CC   UC  U    CG       GUAGAC
                                      CCA
``` | CLEAVAGE INDEPENDENT |

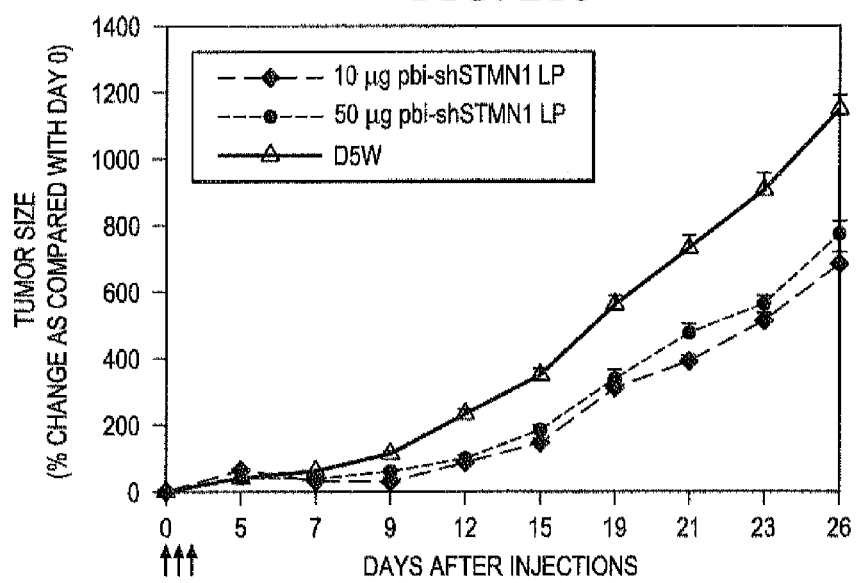

| KINASE | Ser16 | Ser25 | Ser38 | Ser63 |
|---|---|---|---|---|
| CaM II | √ | | | |
| CaM IV/Gr | √ | | | |
| CDK1 | | √ | √ | |
| CDK2 | | √ | √ | |
| CASEIN KINASE II | | | | |
| DNA-DEPENDENT KINASE | | | | |
| KINASE DOWNSTREAM OF TNF | √ | √ | √ | √ |
| MAPK | | √ | √ | |
| KINASE | Ser16 | Ser25 | Ser38 | Ser63 |
| UNKNOWN MT-assoc. | √ | | | |
| PKA | √ | | | √ |
| PKG | | | | |
| p38δ | | √ | √ | |
| p65PAK | √ | | | |
| Plx1 | (UNMAPPED) | | | |

BI-FUNCTIONAL SHRNA TARGETING STATHMIN 1 AND USES THEREOF

CROSS-REFERENCE TO RELATED APPLICATIONS

This patent application is a continuation-in-part of, claims priority to, and incorporates by reference U.S. patent application Ser. No. 13/364,053, filed on Feb. 1, 2012, U.S. patent application Ser. No. 11/983,482, filed on Nov. 9, 2007 and 11/601,431, filed Nov. 17, 2006. This patent application further claims priority to, and incorporates by reference, U.S. provisional patent application Ser. No. 60/932,653, filed Jun. 1, 2007; Ser. No. 60/897,214, filed Jan. 24, 2007; and Ser. No. 60/857,846, filed Nov. 9, 2006. The entire contents of these applications are incorporated herein by reference.

TECHNICAL FIELD OF THE INVENTION

The present invention relates in general to the field of treatment of cancer, and more particularly, to bi-functional shRNA designs to knockdown the expression of Stathmin 1 (STMN1).

STATEMENT OF FEDERALLY FUNDED RESEARCH

None

INCORPORATION-BY-REFERENCE OF MATERIALS FILED ON COMPACT DISC

None

BACKGROUND OF THE INVENTION

Without limiting the scope of the invention, its background is described in connection with Bi-functional shRNA targeting stathmin 1 and uses thereof.

U.S. Patent Application 20070248659 (Shanahan et al 2006) discloses methods for treating cancer, which comprise obtaining a specimen of cancer tissue from a patient; obtaining a specimen of normal tissue in the proximity of the cancer tissue from such patient; extracting total protein and RNA from the cancer tissue and normal tissue; obtaining a protein expression profile of the cancer tissue and normal tissue using 2D DIGE and mass spectrometry; identifying proteins that are expressed in such cancer tissue at significantly different levels than in the normal tissue; obtaining a gene expression profile of the cancer tissue and normal tissue using microarray technology and comparing the results thereof to the protein expression profile; prioritizing over-expressed proteins by assessing the connectivity thereof to other cancer-related or stimulatory proteins; designing an appropriate RNA interference expression cassette to, directly or indirectly, modulate the expression of genes encoding such prioritized proteins; incorporating said cassette into an appropriate delivery vehicle; and providing the patient with an effective amount of the delivery vehicle to, directly or indirectly, modify the expression (i.e., production) of such proteins. Claim 15 recites a method for reducing the rate of cancer cell growth or inducing cancer cell apoptosis, which comprises preparing one or more RNA interference expression cassettes, wherein the cassettes encode nucleic acid sequences at least substantially complementary to mRNA transcripts encoded by the RACK1 gene, the Syntenin gene, and the Stathmin 1 gene; and (b) providing the one or more RNA interference expression cassettes to a cancer cell.

SUMMARY OF THE INVENTION

The present invention includes bi-functional shRNA targeting stathmin 1 and uses thereof. On embodiment of the invention includes bifunctional shRNAs capable of reducing an expression of a Stathmin 1 gene; wherein at least one target site sequence of the bifunctional RNA molecule is located within the Stathmin 1 gene, wherein the bifunctional RNA molecule is capable of activating a cleavage-dependent and a cleavage-independent RNA-induced silencing complex for reducing the expression level of Stathmin 1. In certain aspects, the bifunctional shRNA comprises a RNA sequence defined by DNA SEQ ID NO: 3, SEQ ID NO: 4, or SEQ ID NO: 5. The bifunctional shRNAs may have at least one target site sequence is within a Stathmin 1 gene cDNA sequence; at least one target site sequence may be defined by SEQ ID NO: 1 or SEQ ID NO: 2. In one embodiment, the invention includes an expression vector comprising: a promoter; and a nucleic acid insert operably linked to the promoter, wherein the nucleic acid insert encodes one or more shRNA capable of inhibiting an expression of at least one target gene that is a Stathmin 1 gene via RNA interference, wherein the one or more shRNA comprise a bifunctional RNA molecule that activates a cleavage-dependent and a cleavage-independent RNA-induced silencing complex for reducing the expression level of Stathmin 1. In one aspect, the target site sequence of at least one shRNA comprises SEQ ID NO: 1. A sequence arrangement for the shRNA may comprise a 5' stem arm-19 nucleotide target, which is Stathmin 1-TA-15 nucleotide loop-19 nucleotide target complementary sequence-3' stem arm-Spacer-5' stem arm-19 nucleotide target variant-TA-15 nucleotide loop-19 nucleotide target complementary sequence-3' stem arm. The expression vector may also comprise a nucleic acid insert comprising at least one sequence selected from SEQ ID NO: 3, SEQ ID NO: 4, or SEQ ID NO: 5. In one aspect, at least one shRNA has a target site sequence that is within a Stathmin 1 gene cDNA sequence. In one embodiment, the invention includes a therapeutic delivery system comprising a therapeutic agent carrier; and an expression vector comprising a promoter and a nucleic acid insert operably linked to the promoter, the nucleic acid insert encoding one or more short hairpin RNA (shRNA) capable inhibiting an expression of a target gene sequence that is Stathmin 1 gene via RNA interference, wherein the one or more shRNA comprise a bifunctional RNA molecule that activates a cleavage-dependent and a cleavage-independent RNA-induced silencing complex for reducing the expression level of Stathmin 1. In one aspect, the delivery system includes a therapeutic agent carrier that is a compacted DNA nanoparticle. The DNA nanoparticle may be compacted with one or more polycations, and the one or more polycations may be a 10 kDA polyethylene glycol (PEG)-substituted cysteine-lysine 3-mer peptide (CK30PEG10k). In one aspect, the compacted DNA nanoparticles are further encapsulated in a liposome, and the delivery system of claim 16, wherein the liposome may be a bilamellar invaginated vesicle (BIV). The liposome may also be a reversibly masked liposome; and/or the therapeutic agent carrier may be a liposome. In certain aspects, the target gene sequence comprises SEQ ID NO: 1 or 2; and/or the nucleic acid insert comprises at least one of the sequences selected from SEQ ID NO: 3, SEQ ID NO: 4, or SEQ ID NO: 5. In an embodiment, the invention includes methods to deliver one or more shRNAs to a target tissue expressing an Stathmin 1 gene comprising the steps of preparing an expression vector comprising a promoter and a nucleic acid insert operably linked to the promoter that encodes the one or more shRNA, wherein the one or more shRNA comprise a bifunctional RNA molecule that activates a cleavage-dependent and a cleavage-independent RNA-induced silencing complex for reducing the expression level of Stathmin 1, combining the expression vector with a therapeutic agent carrier, wherein the therapeutic agent carrier comprises a liposome; and administering a therapeutically effective amount of the expression vector and therapeutic agent carrier complex to a patient in need thereof. In certain aspects of the invention, the therapeutic agent carrier is a compacted DNA nanoparticle; the DNA nanoparticle is compacted with one or more polycations, wherein the one or more polycations comprise a 10 kDA polyethylene glycol (PEG)-substituted cysteine-lysine 3-mer peptide (CK30PEG10k) or a 30-mer lysine condensing peptide; the compacted DNA nanoparticles are further encapsulated in a liposome, wherein the liposome is a bilamellar invaginated vesicle (BIV) and is decorated with one or more "smart" receptor targeting moieties; the one or more "smart" receptor targeting moieties are small molecule bivalent beta-turn mimics; the liposome is a reversibly masked liposome; the liposome is a bilamellar invaginated vesicle (BIV); the liposome is a reversibly masked liposome; and/or the one or more "smart" receptor targeting moieties are small molecule bivalent beta-turn mimics. In one aspect, a target site sequence from at least one of SEQ ID NO: 1 or SEQ ID NO: 1. In certain aspects, the nucleic acid insert comprises a sequence selected from SEQ ID NO: 3, SEQ ID NO: 4, or SEQ ID NO: 5. In one embodiment, the invention includes a method to inhibit an expression of a Stathmin 1 gene in one or more target cells comprising the steps of: selecting the one or more target cells; and transfecting the target cell with a vector that expresses one or more short hairpin RNA (shRNAs) capable of inhibiting an expression of a Stathmin 1 gene in the one or more target cells via RNA interference, wherein the one or more shRNA comprise a bifunctional RNA molecule that activates a cleavage-dependent and a cleavage-independent RNA-induced silencing complex for reducing the expression level of Stathmin 1. In one embodiment, the invention includes methods of suppressing a tumor cell growth in a human subject comprising the steps of identifying the human subject in need for suppression of the tumor cell growth; and administering an expression vector in a therapeutic agent carrier complex to the human subject in an amount sufficient to suppress the tumor cell growth, wherein the expression vector expresses one or more shRNA capable inhibiting an expression of a target gene that is Stathmin 1 in the one or more target cells via RNA interference, wherein the one or more shRNA comprise a bifunctional RNA molecule that activates a cleavage-dependent and a cleavage-independent RNA-induced silencing complex for reducing the expression level of the target gene, wherein the inhibition results in an apoptosis, an arrested proliferation, or a reduced invasiveness of the tumor cells. In certain aspects, the therapeutic agent carrier comprises a bilamellar invaginated vesicle (BIV); and/or the therapeutic agent carrier comprises one or more "smart" receptor targeting moieties are small molecule bivalent beta-turn mimics. In certain aspects, administering is selected from the group consisting of subcutaneous, intravenous, intraperitoneal, intramuscular, and intravenous injection; administering comprises intratumoral injection; and/or administering comprises injecting with a DNA:lipoplex. In certain aspects, the tumor cell growth is selected from the group consisting of osteosarcoma, melanoma, colon cancer, breast cancer, pancreatic cancer, lung cancer, adenocarcinoma, ovarian carcinoma, prostate cancer, head cancer, neck cancer, hepatocellular carcinoma, osteosarcoma, lung cancer, lung adenocarcinoma, insulinoma, brain Glioma, mammary adenocarcinoma, liver hepatoma, nasal squamous carcinoma, small intestine adenocarcinoma, colorectal carcinoma, and leukemia, wilms tumor.

BRIEF DESCRIPTION OF THE DRAWINGS

For a more complete understanding of the features and advantages of the present invention, reference is now made to the detailed description of the invention along with the accompanying figures and in which:

FIG. 3 shows a diagram illustrating the detection of mature shRNA by the Stem-Loop RT-PCR Method. Schematic illustration of mature shRNA amplification by stem-loop RT-PCR method. Total RNA is first reverse-transcribed with a sequence specific stem-loop RT primer that recognizes the 3' end of a siRNA/miRNA for cDNA synthesis. Stem-loop RT primer synthesized cDNA was then amplified with a set of PCR primers that are specific for siRNA/miRNA and for the stem-loop RT primer. The resulting RT-PCR product is predicted to be 59 base pairs. The strategy can be used to detect either the guide strand or the passenger strand of siRNA/miRNA.

FIG. 4a shows a photo-image of agarose gel demonstrating the RT-PCR product of the guide (antisense) strand (black arrow). Total cellular RNA was first reverse-transcribed with guide strand specific stem-loop RT primer and subsequently amplified with the guide strand specific and stem-loop specific PCR primer set. PCR amplified product was run onto a 4% agarose gel and stained with ethidium bromide and visualized under UV light. The red arrow indicates a processing intermediate, containing 11 bases of the miR30 stem (sequence of both PCR products were confirmed by SeqWright).

FIG. 8 shows expression constructs for pbi-shRNA™ STMN1, pGBI-1 (cleavage dependent component) and pGBI-3 (cleavage independent component). shRNA sequences inserted into the multiple cloning sites of pUMVC3.

| Lane 1 | MW size marker |
| --- | --- |
| Lane 2 | Electroporation without plasmid DNA |
| Lane 3 | Electroporation with 25 ug of plasmid DNA |
| Lane 4 | Electroporation with 50 ug of plasmid DNA |
| Lane 5 | Electroporation with 75 ug of plasmid DNA |

Figure 14:
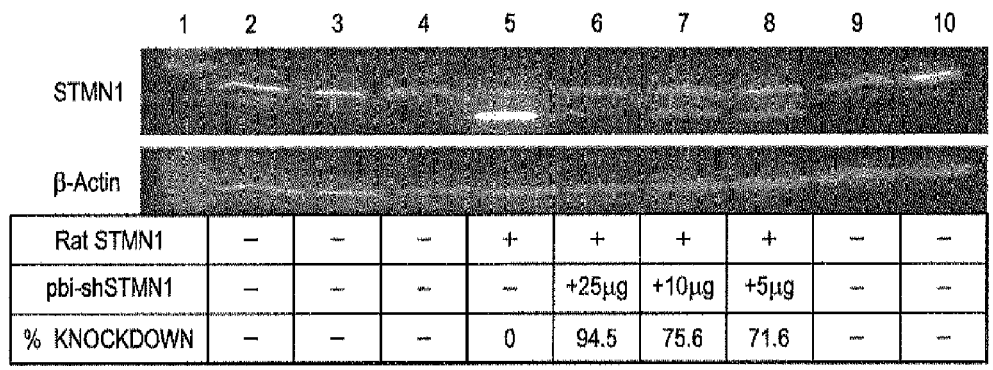

FIG. 14 shows knockdown truncated rat STMN1 by pbi-shRNA™ STMN1. CCL-247 cells were co-transfected by electroporation with 25 ug of truncated rat STMN1 expression plasmid and varied amount of pbi-shRNA™ STMN1. At 72 hours post electroporation, 30 ug of protein from the cell extract of each treatment condition was loaded per well of SDS-PAGE for Western immunoblot (upper STMN1 band=endogenous human STMN1; lower STMN1 band=truncated rat STMN1 transgene). Percent (%) knockdown indicate rat STMN1 knockdown was assessed by semi-quantitative comparison to expression level of Lane 5.

| Lane 1 | MW size marker |
| --- | --- |
| Lane 2 | CCL-247 cells without electroporation |
| Lane 3 | CCL-247 cells electroporated without DNA |
| Lane 4 | CCL-247 cells electroporated with 50 ug of salmon sperm DNA |
| Lane 5 | CCL-247 cells electroporated with 25 ug of rat STMN1 expression plasmid plus 25 ug of salmon sperm DNA |
| Lane 6 | CCL-247 cells electroporated with 25 ug of rat STMN1 expression plasmid plus 25 ug of pbi-shRNA ™ STMN1 |
| Lane 7 | CCL-247 cells electroporated with 25 ug of rat Stmn1 expression plasmid plus 10 ug of pbi-shRNA ™ STMN1 and 15 ug of salmon sperm DNA |
| Lane 8 | CCL-247 cells electroporated with 25 ug of rat STMN1 expression plasmid plus 5 ug of pbi-shRNA ™ STMN1 and 20 ug of salmon sperm DNA |
| Lane 9 | CCL-247 cells electroporated with 25 ug of empty vector (pUMVC3) |
| Lane 10 | CCL-247 cells without treatment |

Figure 15:
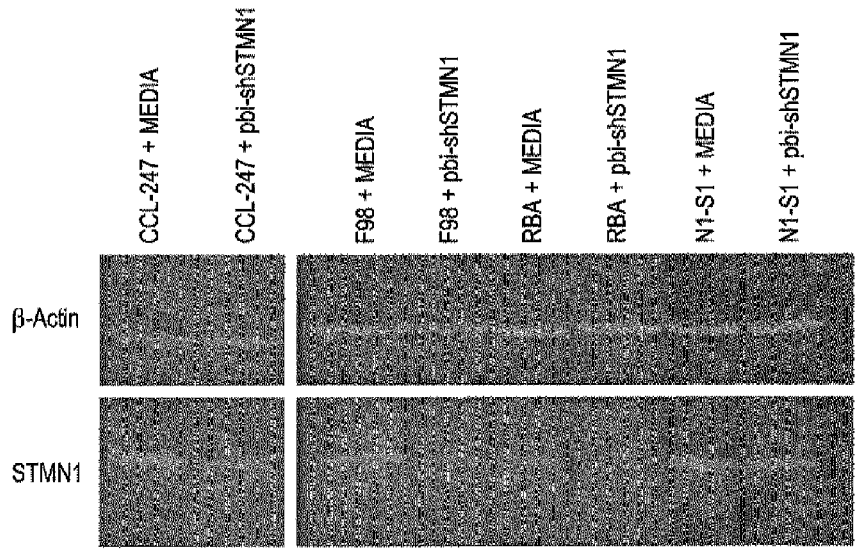

FIG. 15 shows rat STMN1 knockdown by pbi-shRNA™ STMN1. Rat tumor cell line cells and human colorectal cancer cells were either transfected (+pbi-shRNA™ STMN1) or not transfected (+media) with pbi-shRNA™ STMN1. Cell extracts were prepared 24 hours post transfection, β-actin and STMN1 were detected by Western immunoblot.

Figure 16:
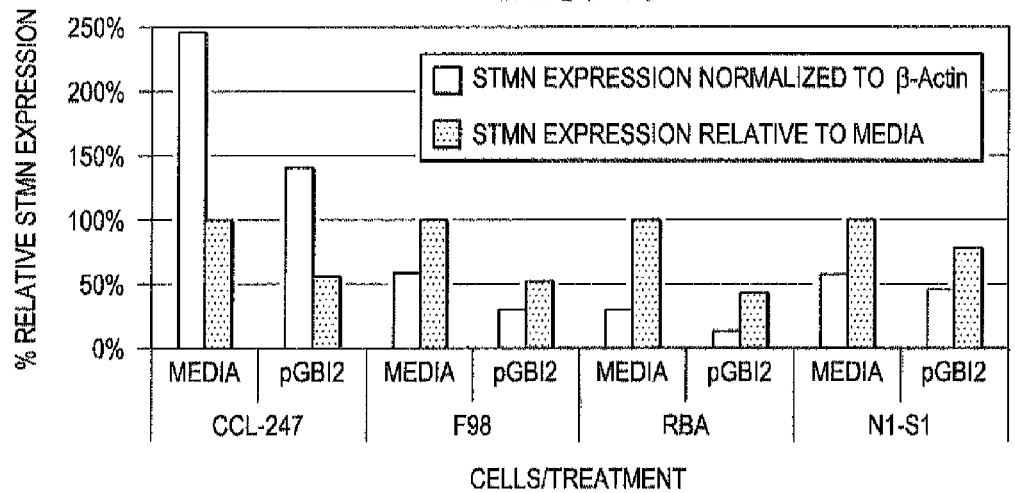

FIG. 16 shows semi-Quantitative Analysis of STMN1 knockdown. Western immunoblot shown on FIG. 13 was scanned for semi-quantitative analysis of STMN1 protein expression. Comparative percentage of STMN1 expression was either normalized to β-actin level (blue bar) or relative to the media control (red bar). (pGBI2=pbi-shRNA™ STMN1).

Figure 17:
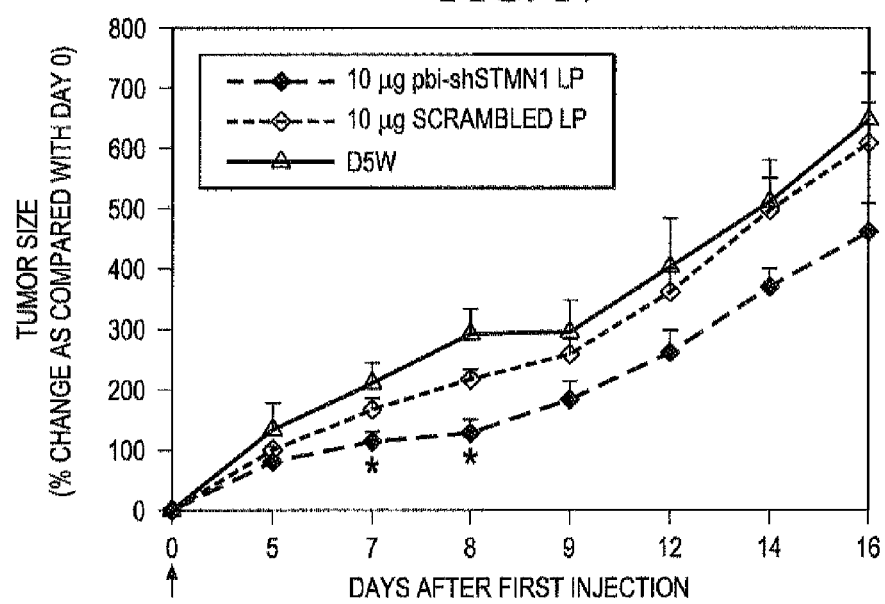

FIG. 17 shows growth inhibitory activity of a single intra-tumoral injection of pbi-shRNA™ STMN1 LP on CCL-247 xenograft growth (Results of RE-PTL-105 study). * p<0.05 by student t test as compared with D5W cohort. (Red arrow indicates injection day.)

Figure 18:
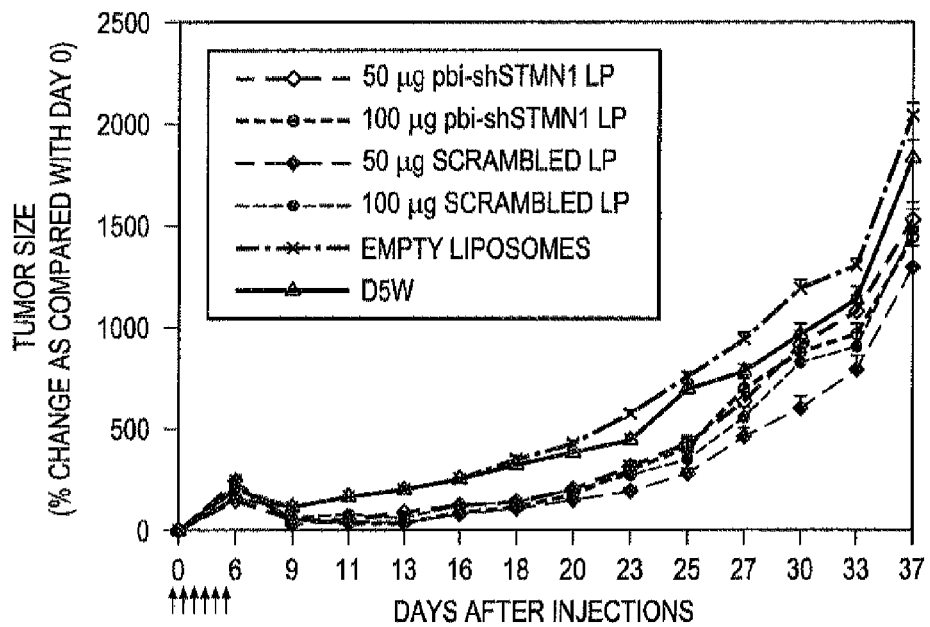

FIG. 18 (RE-PTL-107) shows the effect of six IT injections of pbi-shRNA™ STMN1 LP at two doses (50 ug and 100 ug) compared to controls, on CCL-247 tumor xenograft size. (*CCL-247 tumor xenografts were intratumorally injected once a day on Days 5, 4, 3, 2, 1 and Day 0. Red arrows indicate injection days.)

Figure 19:
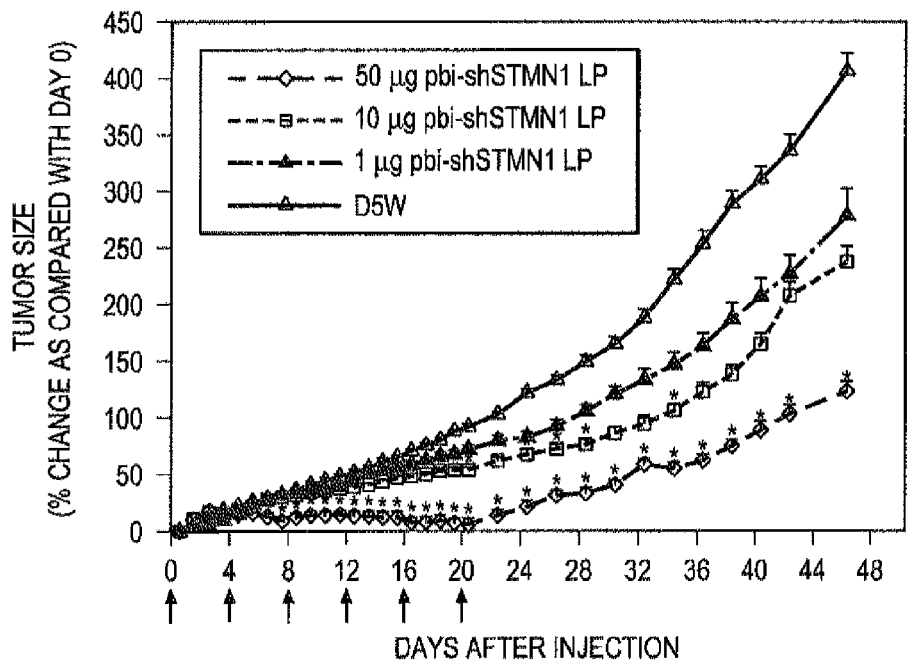

FIG. 19 shows anti-tumor activity of pbi-shRNA™ STMN1 LP against low passage human melanoma tumorgrafts (Result of RE-PTL-120 study). Melanoma tumorgrafts were injected bi-weekly for 3 weeks. Values represent mean±SEM. Significant reduction by pbi-shRNA™ STMN1 LP was extended to day 46 for the 50 ug dose group. (Red arrow indicates injection days.)

Figure 20:
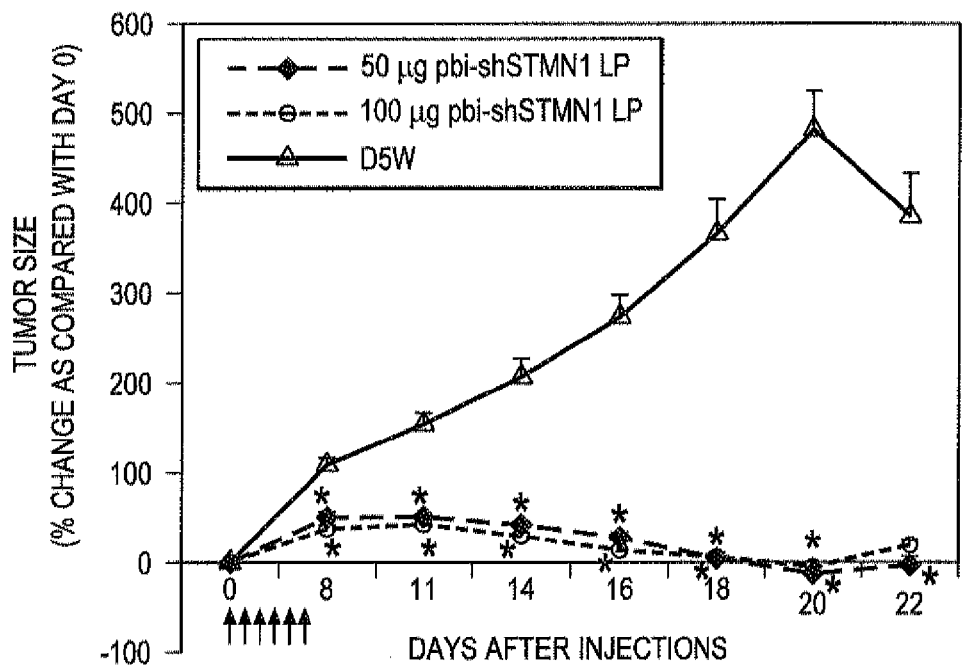

FIG. 20 shows anti-tumor activity of pbi-shRNA™ STMN1 against low passage human osteosarcoma tumorgrafts. Daily IT injections of pbi-shRNA™ STMN1 or control were administered to osteosarcoma tumorgrafts. Values represents mean±SEM. (Red arrow indicates injection days.)

Figure 21A:
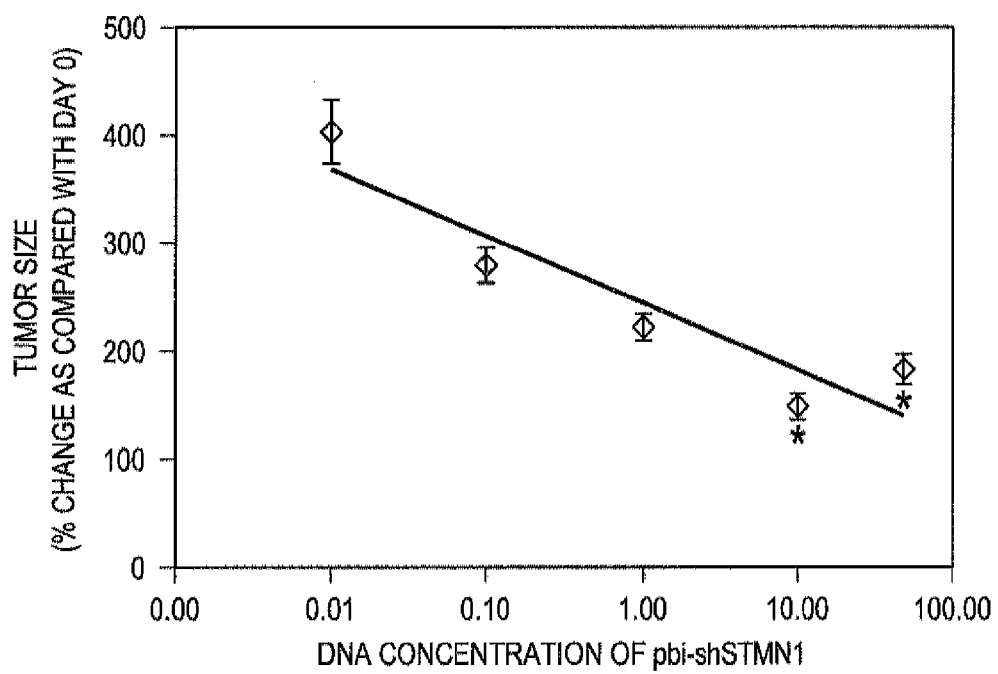

FIG. 21a shows a dose-dependent inhibitory activity of pbi-shRNA™ STMN1 LP (Day 15) (Results of RE-PTL-115 study). CCL-247 tumor xenografts in athymic nude mice were injected once daily for 3 consecutive days, values represent mean±SEM. Diluent (D5W) treated tumors attained 352% of its original size at Day 15.

FIG. 21b shows prolonged tumor growth reduction by pbi-shRNA™ STMN1 LP (Results of RE-PTL-115 study). CCL-247 tumor xenografts in athymic nude mice were injected once daily for 3 consecutive days, values represent mean±SEM. (Red arrow indicates injection days.)

Figure 22:
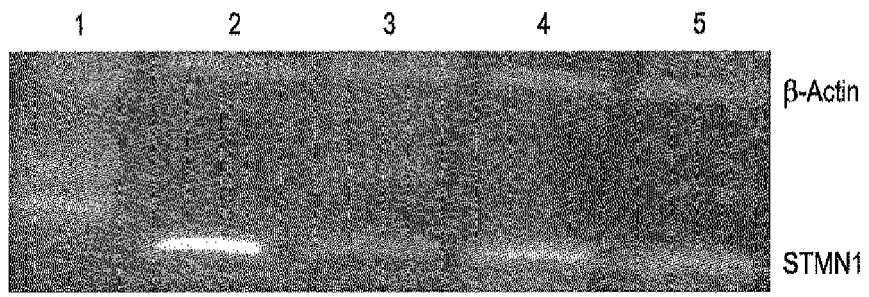

FIG. 22 shows in vivo STMN1 expression following pbi-shRNA™ STMN1 LP treatment in CCL-247 tumor xenografts.

| Lane 1 | Molecular weight ladder | % STMN1 Expression |
|---|---|---|
| Lane 2 | CCL-247 cell lysate (positive control) | 100% |
| Lane 3 | CCL-247 tumor xenografts treated with 10 ug pbi-shSTMN1 LP, harvested at 24 hr | 56% |
| Lane 4 | CCL-247 tumor xenografts treated with 10 ug scrambled LP, harvested at 24 hr | 100% |
| Lane 5 | CCL-247 tumor xenografts treated with D5W, harvested at 24 hr | 100% |

Figure 23:
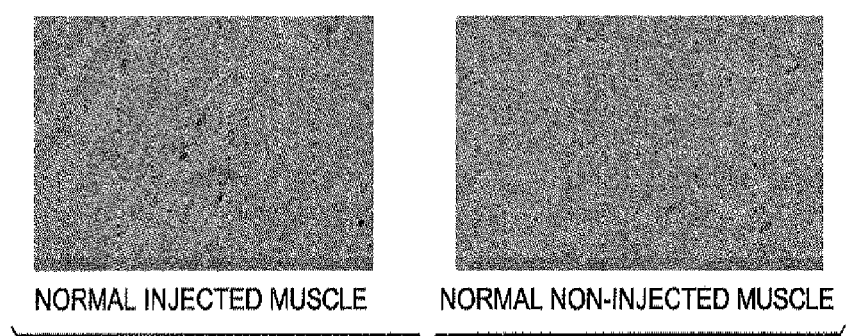

FIG. 23 documents that there was no observable histopathology from injection of GNE-lipoplexes.

Figure 24:
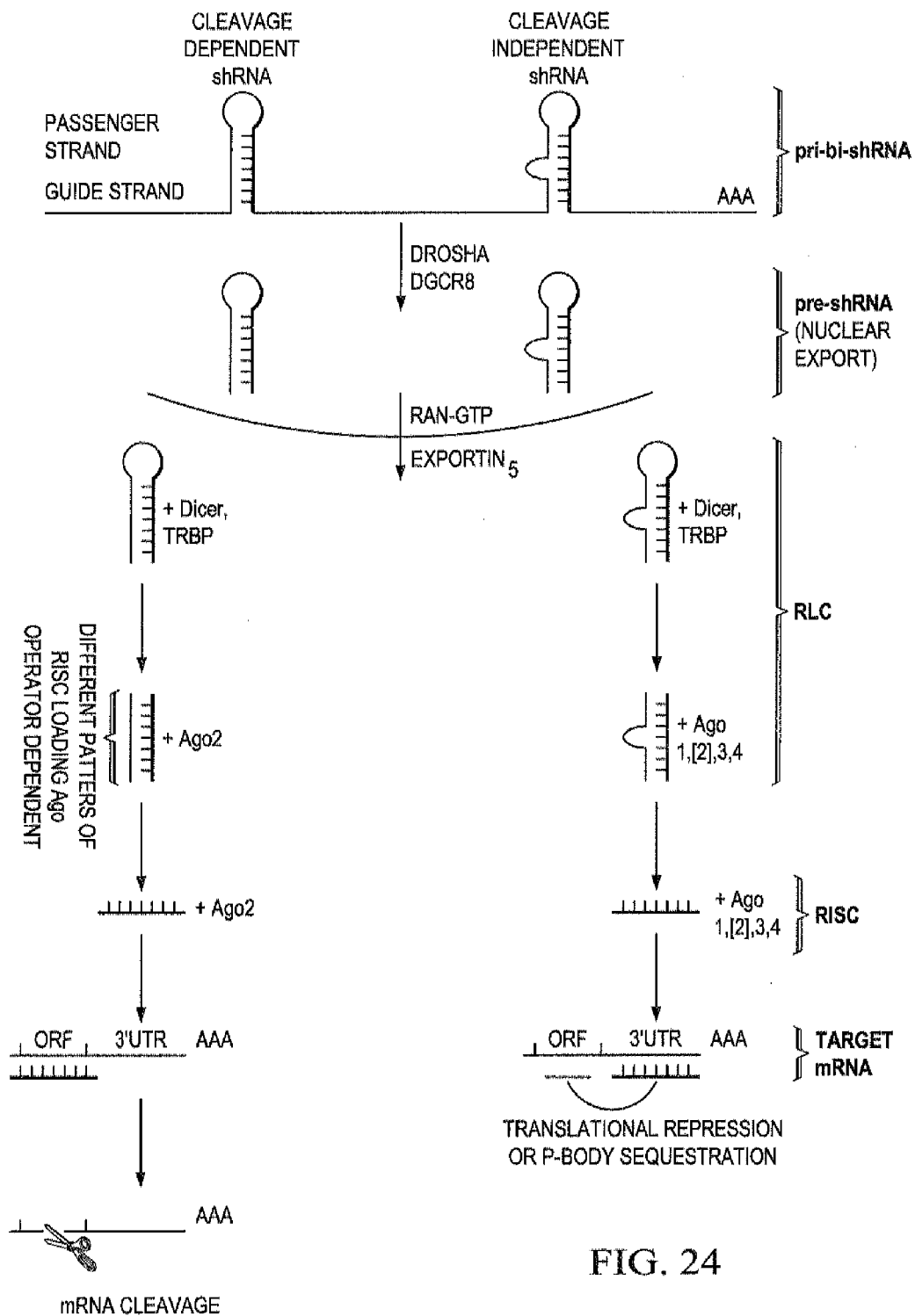

FIG. 24 shows simultaneous activating RNA Interference via multiple pathways. Schematic illustration of the proposed bifunctional shRNA molecules capable of simultaneous activating multiple RNA interference pathways. (Red stem passenger strand; blue stem is guide strand).

Figure 25:
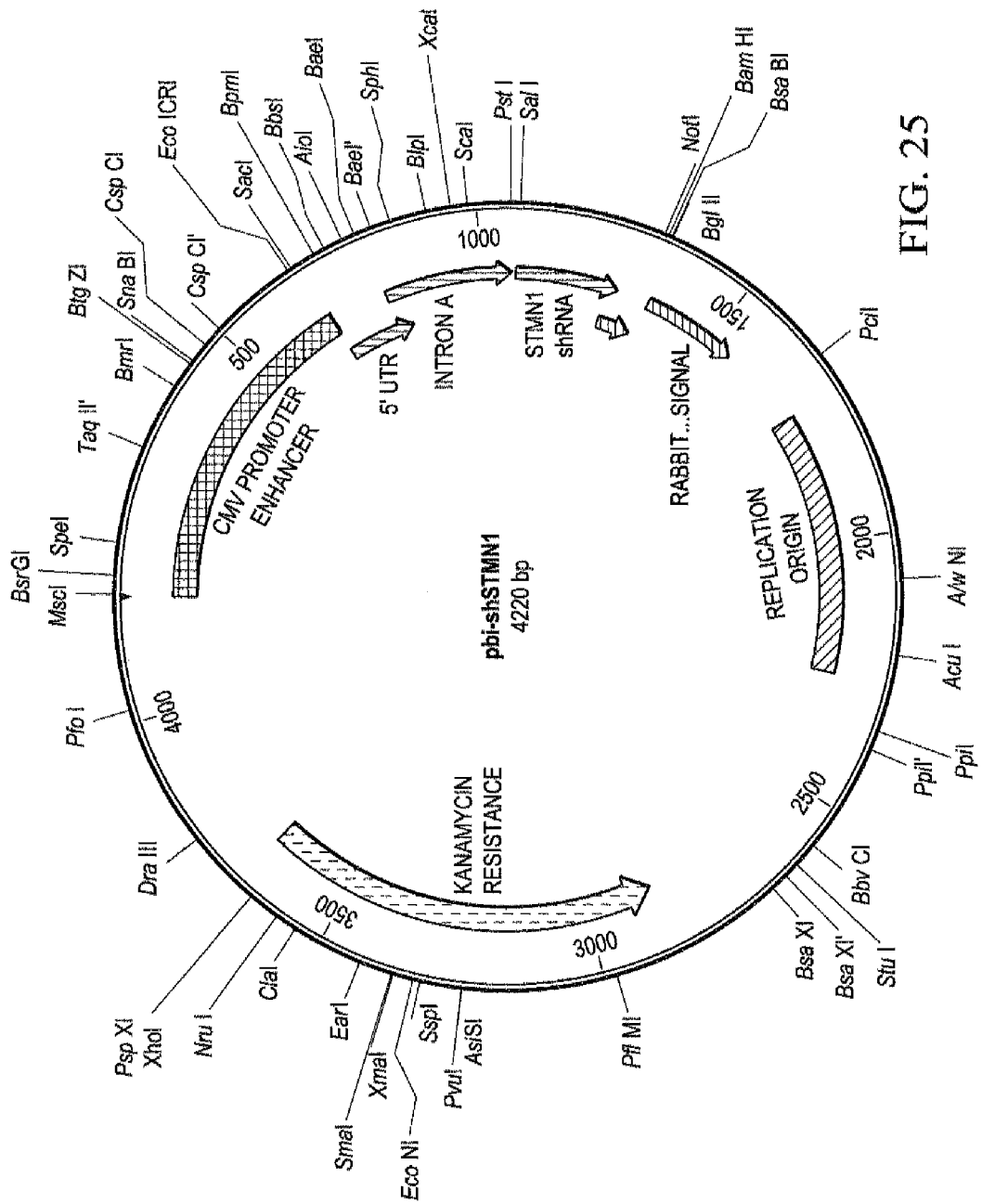

FIG. 25 is a schematic diagram of the expression of pbi-shRNA™ STMN1. pUMVC3 vector's mammalian expression unit contains enhanced CMV promoter with CMV IE 5' UTR and partial IE Intron A and rabbit beta-globin poly A site. The shRNA expression unit is inserted in the multiple cloning sites between the CMV IE Intron A and rabbit beta-globin poly A sites.

Figures 26, 27:
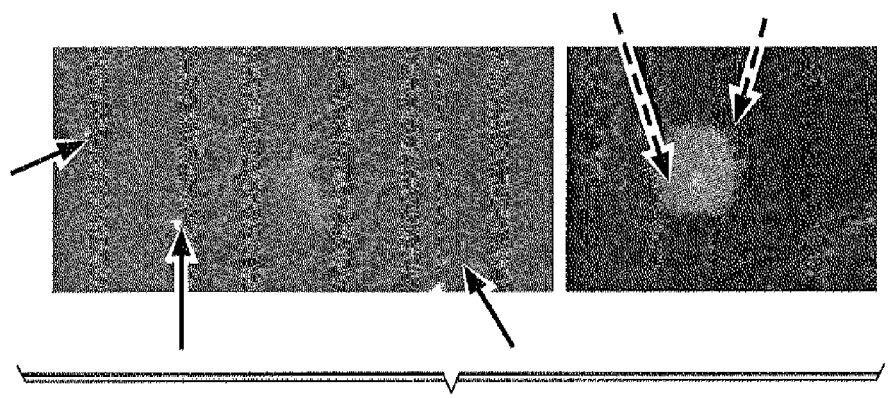

FIG. 26 shows a summary of kinases phosphorylating stathmin.

FIG. 27 shows wide-field, deconvolution fluorescence microscopy PANC1 cells. Probes Used/Emission Wavelength/(color): Liposomes Bodipy Cholesterol 523 (green); Plasmid DNA Rhodamine 594 (red); and Nuclei Stain DAPI 435 (blue). Left: 5 minutes showing surface BIV-L localization consistent with fusogenic mechanism. Right: 30 minutes

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Stathmin 1 (STMN1) belongs to the stathmin family of genes. It encodes a ubiquitous cytosolic phosphoprotein that functions as an intracellular relay integrating regulatory signals of the cellular environment. STMN1 is involved in the regulation of the microtubule filament system by destabilizing microtubules. It prevents assembly and promotes disassembly of microtubules. Overexpression of STMN1 is found in many cancers. This invention utilizes bi-functional shRNA design for advantageous formulation to knockdown the expression of STMN1 for the treatment of cancer.

STMN1, overexpressed in multiple human solid cancers, regulates G2M cell cycle transition via tubulin compartmentalization, microtubule catastrophe and microtubule depolymerization and also contributes to the cancer metastatic process. The present inventors identified the STMN1 protein to be a biorelevant gene target candidate vulnerable to attack in the otherwise robust rewired cancer molecular network (Letai 2008) and have confirmed STMN1 overexpression in 86% (30/35) of tumor specimens across multiple tumor histotypes at the Mary Crowley Cancer Research Centers (MCCRC).

Disclosed is the therapeutic use of the innovative RNA interference bi-shRNA platform to achieve post-transcriptional knockdown of STMN1.

RNA interference (RNAi), the Nobel prize winning discovery by Fire and Mello in 1998, has fostered an exponential number of studies and publications furthering the understanding of gene function and stimulating numerous phase I and II clinical trials. This naturally occurring gene-silencing mechanism by small RNAs, which includes endogenous microRNA (miRNA), is highly dependent on gene sequence; thus the mechanism can, in theory, be used to inhibit the expression of any targeted gene[s] with strong specificity. RNAi is not limited by the pharmacologic constraints inherent to the development of small molecules which creates an opportunity to access traditionally "undruggable" targets for disease treatment.

The central player of this mechanism is the RNA Induced Silencing Complex (RISC). The process starts with double-stranded small RNA (composed of a passenger strand and a guide strand) which is incorporated into the pre-RISC followed by the cleavage-dependent or cleavage-independent release of the passenger strand to form the guide strand containing RISC (10). The guide strand (anti-sense to mRNA) guides the RISC to recognize the target mRNA through sequence complementarity (full or extended partial). A key component of RISC is the family of Argonaute proteins (Ago), Ago 1, 2, 3 and 4 in mammalian systems, of which only Ago 2 has endonuclease activity so as to allow for cleavage of the target mRNA for further degradation (cleavage dependent pathway) (10, 12); all the Ago containing RISC can function through a cleavage-independent effector pathway resulting in translation repression and mRNA sequestration in p-body with subsequent degradation (13, 14). The cleavage-dependent effector process requires extensive homology between guide strand and both the passenger strand and target mRNA, particularly in the central region; the cleavage-independent effector process, on the other hand, only requires partial homology between guide strand and both the passenger strand and target mRNA.

The present invention takes advantage of both cleavage dependent and cleavage independent loading at the RISC complex, not downstream from the RISC complex. Thus, as used herein the phrase "cleavage dependent and cleavage independent" refers to the design of RNA(s) that are specifically targeted to RISC and the cleavage dependent and cleavage independent activities at the RISC complex, i.e. loading. It has been found herein and in the parent application for this case, that these "bifunctional shRNAs" have a higher inhibitory activity than the sum of targeting each individual part of the RISC complex. Thus, the higher inhibitory activity of the present invention.

RNA interference can be triggered either by synthetic double stranded small interfering RNA (siRNA) or by vector driven short hairpin RNA (shRNA). Both siRNA and vector driven shRNA have been demonstrated to be effective in in vitro and in vivo applications, each with their respective advantages. Most siRNA are structurally designed to promote efficient incorporation into the Ago2 containing RISC, the RNase III containing Dicer-substrate design improves the efficiency of siRNA at least 10-fold by initial association and processing at the pre-RISC (19). Vector driven shRNA utilizes the host microRNA biogenesis pathway, which appears to be more efficient (20, 21). siRNA is more readily chemically modified while shRNA expression can be modulated and regulated by specific promoters.

The present inventors developed the novel vector driven shRNA technology, the bi-functional shRNA (bi-shRNA), to further improve the efficiency of RNAi by harnessing both cleavage-dependent and cleavage-independent pathways of RISC loading in one pre-programed molecule. The vector driven bi-shRNA includes two stem-loop structures for each mRNA target sequence, one stem-loop shRNA has perfect complementarity at the stem and the second stem-loop shRNA contains mismatches on the passenger strand of the stem (thereby differing from prior art mismatched RNA that include the mismatch on the guide strand). Importantly, following incorporation into the RISC, the guide strands derived from each of the two structures are fully complementary to the mRNA target sequence but are associated with different Ago containing RISCs. The bi-shRNA design leads to more rapid onset of gene silencing, higher efficacy, and greater durability when compared with either siRNA or conventional shRNA. Currently personalized cancer therapy with target specific bi-shRNA is transitioned into the clinic in Phase I studies using a modified bilamellar invaginated liposome delivery vehicle. Key molecular methods involved in design, construction, and the implementation of bi-shRNA are provided below.

Briefly, a target gene is selected, and in certain embodiments, an initial step is to determine the objective of the study. Depending on that objective and the embodiments, several different vectors, promoters, or plasmid backbones and delivery systems can be used. It has been found useful to choose an expression vector with efficient transgene expression. The inventor found that an expression vector with powerful promoters, e.g., an extended CMV promoter containing IE 5'UTR and partial Intron A (pUMVC3), is more effective than those with a cloning site immediately adjacent to the CMV promoter. In certain embodiments it is beneficial to have a stretch of lead transcript before the stem-loop structures. In addition, if more than one vector usage is planned, an effective shuttle strategy should be worked out beforehand; modification by PCR amplification of the expressed cassette is not as efficient. The choice of promoter is also important; RNA polymerase III promoters are much stronger in expression but competitively saturate the endogenous miRNA maturation process at both the nuclear export and RISC loading steps resulting in lethal toxicity in vitro and in vivo with certain delivery vehicles. RNA polymerase II promoters, although less strong in expression, works efficiently and is much less toxic vis-à-vis competition for the endogenous miRNA pathway.

In certain embodiments a sequence that can act in more than one species is designed, particularly if multiple animal model systems are utilized. For most target genes, it is possible to find stretches of target nucleotides that are conserved between species. For finding a sequence that is both conserved and optimum for knockdown, one has to compare the homology-matched sequence with the selected target site sequence.

Public accessible computer programs using differing algorithms (e.g. Dharmacon RNAi design center (www.dharmacon.com) and IDT (www.idtdna.com) are readily available and can be used to locate appropriate target sites within the targeted gene. A search with most computer programs will often yield a preliminary first set of targets for further analysis. Some available publications offer do and do-not suggestions. A BLAST search for each target sequence is to be taken in order to analyze potential cross homology with other mRNAs within the species of interest.

Once the target site sequence is selected, the bi-shRNA design process can begin; the design process is presented below. The bi-shRNA stem-loop structure routinely used by the inventor employs the well-analyzed miR-30a backbone, although, any functional miRNA backbone can be used. The bi-shRNA consists of the two stem-loop structures on a miR-30a backbone located immediately adjacent to each other with a gap about 10 nucleotides long. A longer nucleotide gap can be used and multiple units of bi-sh RNA can be designed to string together in a single transcript targeting either a single gene at multiple sites or multiple different genes simultaneously.

To construct the expression unit to be placed in the multiple cloning sites of an expression vector, an assembly strategy using synthetic oligonucleotides sequentially linked together has been developed. Alternatively, one can also outsource the synthesis of the gene construct with the specified sequence to a biotechnology service company. For the oligonucleotide assembly process, overlapping DNA fragments were designed and synthesized. Because of redundant sequences in the two stem-loop structures, it is necessary to initially ligate the 5' fragments and 3' fragments. The 5' fragment and the 3' fragment can then be purified on gel and further ligated to the middle linking fragments. This assembly process is efficient and, with careful design, many fragments can be repetitively used for different bi-functional constructs.

For each target, it is the best to design and construct at least three bi-functional constructs to compare and from which to select a construct with high knockdown efficiency for further evaluation. Knockdown efficiency can be compared in vitro in tissue culture cells. The inventor has recognized that is generally difficult to compare the knockdown efficiency with endogenously expressed genes because in vitro transfection methods have widely different efficiencies; this is particularly so when the transfection efficiency is low as the knockdown is hard to assess due to background noise from untransfected cells. The present inventor has developed a more effective method in which both the bi-functional construct and transgene expression vector are co-transfected; this allows target gene expression knockdown to be effectively compared and quantified.

Efficacy and efficiency of target gene knockdown by bi-shRNA can be tested with a variety of in vitro and in vivo systems depending on the target and planned application. This in vitro assessment can be conducted following transfection of the bi-shRNA expression plasmids in a variety of cultured cells. The present inventor found that transfections by both electroporation and by liposome (e.g. Lipofectamine 2000) are highly effective, when the amount of plasmid DNA is carefully controlled using a control vector or universal random sequence. For Lipofectamine or a related agent, the present inventor found that the reverse transfection method, in general, is less toxic than the forward transfection method. Target gene knockdown can be assessed by either qRT-PCR for target gene mRNA or by Western and/or ELISA for target gene protein. These assays are well described in many publications. Two assay methods are presented in detail here: one detects the expression of mature shRNA by stem-loop RT-PCR, the other detects the target mRNA cleavage by 5' RNA-Ligand Mediated RACE (5' RLM-RACE). Both these methods were successfully used to assess the efficacy of bi-shRNA both in vitro and in vivo. Stem-loop RT-PCR is a sensitive method dependent on the specific probe primer used; in addition, one can specifically detect and quantify both the passenger strand and guide strand. For bi-shRNA, the method can differentially score both the fully complementary as well as the mismatched (partially complementary) passenger strand. The 5' RLM-RACE method requires ligation of an RNA oligomer onto the cleaved mRNA end, consequently, the method is rendered less efficient. Insofar as a number of rounds of amplifications are often required, a nested primer design is essential to ensure specificity.

Evaluable functionality of bi-shRNA relies on effective plasmid delivery into target cells. The inventors recognize that some in vitro transfection systems often do not translate to inherently more complex in vivo animal models. There are numerous delivery systems designed specifically for systemic applications in vivo. The present inventor has utilized the fusogenic, cationic DOTAP:cholesterol bilamellar invaginated vesicle lipoplex (BIV) for in vivo studies and has successfully translated it to the clinic. Currently modification strategies for more focused biodistribution, targeted delivery, and enhanced intracellular uptake are being developed. An effective lipoplex should use plasmids devoid of any contaminants from host E. coli. Although endo-free plasmid purification kit produced plasmids are generally used, GLP or GMP produced plasmids are more effective. Unfortunately, colanic acid and other non-endotoxin associated polysaccharides co-purify with DNA by anion exchange chromatography and by cesium chloride density gradient centrifugation. Therefore, endotoxin removal does not remove these contaminants, and HPLC cannot detect these contaminants. To correct this, the Superclean™ procedure has been developed to generate ultra-high quality plasmid DNA, cleansed of these contaminants, for in vivo and clinical applications. Liposome preparation involves highly specialized equipment; the present inventors routinely generate the DOTAP:cholesterol BIV in a GMP facility. Pre-made liposome may be obtained from a collaborator or purchased from a vendor. The process of preparing lipoplex with high quality liposome and plasmid DNA is described below. The lipoplex formulation can be achieved in most laboratory settings. Once the lipoplex is made, the formulation can be delivered systemically to experimental animals either through slow tail vein injection or with catheters. Target site vector expression can be analyzed using the PCR method for plasmid DNA and the stem-loop RT-PCR for mature bi-shRNA, respectively. bi-shRNA functionality can be assayed with the 5' RLM-RACE for target mRNA cleavage and with Western blot or IHC for target protein knockdown. These analyses can be performed at about 48 hours post treatment. For efficacy, repeated delivery into the experimental animal is often required; the dosing schedule needs to be experimentally determined and optimized.

The invention provides that target gene-specific shRNAs may be designed to enter into and interact with the cleavage-dependent RISC and cleavage-independent RISC pathways. As used herein, the term "bifunctional shRNA" generally means one or more RNA molecules, each of which include a double stranded sequence that resides within a stem portion of separate stem-loop structures, wherein a first RNA molecule is designed to be presented to a cleavage-dependent RISC pathway and a second RNA molecule is designed to be presented to a cleavage-independent RISC pathway. In certain embodiments, the bi-shRNA is all on a single strand.

More specifically, a first guide strand sequence is complementary, preferably 100% complementary, to at least a portion of an mRNA transcript encoded by a target gene. The invention provides that this guide strand (which is initially bonded to the passenger strand to form the double stranded stem) comprises a nucleic acid sequence that is capable of binding to the mRNA transcript of the target gene, and is presented to the cleavage-dependent RISC pathway. The invention provides that such binding of the guide strand sequence to the mRNA transcript, and presentation to the cleavage-dependent RISC pathway, causes degradation of the mRNA transcript.

In particular embodiments, it is provided that the second guide strand sequence is at least partially complementary to at least a portion of the mRNA transcript encoded by the target gene. More particularly, the second guide strand sequence may contain a first portion that is complementary, preferably 100% complementary, to the mRNA transcript encoded by the target gene, whereas a second portion of the guide strand sequence contains certain bases that are mismatched with the corresponding sequence of the target gene mRNA transcript.

As used herein, a "mismatched" base pair refers to two nitrogenous bases within a nucleic acid sequence that, when bound (or hybridized) to each other, do not follow Chargaffs rules of base pairing. Chargaffs rules provide that the purine adenine (A) within a first nucleic acid sequence will pair with the pyrimidine thymine (T) (or uridine (U)) within a second nucleic acid sequence. Furthermore, Chargaffs rules provide that the purine guanine (G) within a first nucleic acid sequence will pair with the pyrimidine cytosine (C) within a second nucleic acid sequence. Thus, a base pairing between two strands (nucleic acid sequences) that does not follow and comply with such rules would be deemed a "mismatched" base pair, e.g., a pairing between G and U, A and G, A and C, G and T, G and U, and so on. A guide strand within the double stranded sequence of the stem-loop structures shown therein, which contain one or more "mismatched" base pairs relative to the passenger strand, creates a bulge in the double stranded stem sequence.

As used herein the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "expression vector" as used herein in the specification and the claims includes nucleic acid molecules encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. The term "promoter" refers to any DNA sequence which, when associated with a structural gene in a host yeast cell, increases, for that structural gene, one or more of 1) transcription, 2) translation or 3) mRNA stability, compared to transcription, translation or mRNA stability (longer half-life of mRNA) in the absence of the promoter sequence, under appropriate growth conditions.

The term "oncogene" as used herein refers to genes that permit the formation and survival of malignant neoplastic cells (Bradshaw, T. K.: Mutagenesis 1, 91-97 (1986).

As used herein the term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

The term "hybridizing" refers to any process by which a strand of nucleic acid binds with a complementary strand through base pairing.

The term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein the term "bi-functional" refers to a shRNA having two mechanistic pathways of action, that of the siRNA and that of the miRNA. The term "traditional" shRNA refers to a DNA transcription derived RNA acting by the siRNA mechanism of action. The term "doublet" shRNA refers to two shRNAs, each acting against the expression of two different genes but in the "traditional" siRNA mode.

As used herein, the term "liposome" refers to a closed structure composed of lipid bilayers surrounding an internal aqueous space. The term "polycation" as used herein denotes a material having multiple cationic moieties, such as quaternary ammonium radicals, in the same molecule and includes the free bases as well as the pharmaceutically-acceptable salts thereof.

Accordingly, the bifunctional shRNAs may comprise shRNAs designed to enter into and interact with both cleavage-dependent RISC and cleavage-independent RISC. A higher level of gene "knock-down" is achieved using such bifunctional shRNAs compared to other currently-available RNAi methods and compositions, including siRNAs and conventional shRNAs (i.e., shRNA constructs designed to enter cleavage-dependent RISC or cleavage-independent RISC, but not both).

As used herein, gene "knock-down" refers to effective quantitative and durable inhibition of expression. Such gene "knock-down" may be manifested, and/or apparent, in the suppression of target gene mRNA translation, increased target cell apoptosis and/or cell kill.

As used herein, "target gene" refers to a nucleic acid sequence in a cell, wherein the expression of the sequence may be specifically and effectively modulated using the bifunctional shRNA. In certain embodiments, the target gene may be implicated in the growth (proliferation), maintenance (survival), and/or migratory (metastatic) behavior of an individual's cancer. The invention provides, however, that the target gene may be implicated in any other disease or medical condition, and is not limited to genes implicated in cancer. For example, the target gene may represent any sequence that an investigator or clinician wishes to silence (i.e., reduce the expression level of such target gene).

Vector sequence may comprise a promoter, which is operably linked (or connected), directly or indirectly, to a sequence encoding the bifunctional shRNAs. Such promoters may be selected based on the host cell and the effect sought. Non-limiting examples of suitable promoters include constitutive and inducible promoters, such as inducible RNA polymerase II (pol II)-based promoters. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case it will be appreciated that the T7 polymerase must also be present). The invention shall not be restricted to the use of any single promoter, especially since the invention may comprise two or more bifunctional-shRNAs (i.e., a combination of effectors), including but not limited to incorporated shRNA singlets. Each incorporated promoter may control one, or any combination of, the shRNA singlet components.

In certain embodiments, the promoter may be preferentially active in the targeted cells, e.g., it may be desirable to preferentially express the bifunctional shRNA molecules in tumor cells using a tumor cell-specific promoter. Introduction of such constructs into host cells may be effected under conditions whereby the two or more RNA molecules that are contained within the bifunctional shRNA precursor transcript initially reside within a single primary transcript, such that the separate RNA molecules (each comprising its own stem-loop structure) are subsequently excised from such precursor transcript by an endogenous ribonuclease. The invention further provides that splice donor and acceptor sequences may be strategically placed within the primary transcript sequence to promote splicesome-mediated nuclear processing. The resulting mature shRNAs may then induce degradation, and/or translation repression, of target gene mRNA transcripts produced in the cell. Alternatively, each precursor stem-loop structure may be produced as part of a separate transcript, in which case each shRNA-encoding sequence will preferably include its own promoter and transcription terminator sequences. Additionally, the bifunctional shRNA precursor transcript may reside within a single primary transcript, which, optionally, further comprises of one or more mRNA sequences that encode one or more functional mammalian proteins. For example, the one or more mRNA sequences may encode certain proteins that are known to bolster a patient's immune system, or otherwise provide some preventative and/or therapeutic effect that will operate in parallel with the bifunctional shRNA.

The stem-loop structures of the shRNA molecules described herein may be about 40 to 100 nucleotides long or, preferably, about 50 to 75 nucleotides long. The stem region may be about 19-45 nucleotides in length (or more), or more preferably about 20-30 nucleotides in length. The stem may comprise a perfectly complementary duplex (but for any 3' tail), however, bulges or interior loops may be present, and even preferred, on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. More particularly, the loop portion will preferably be 6-15 nucleotides in size.

As described herein, the stem regions of the bifunctional shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nim.nih.qov/BLAST).

Expression level of multiple target genes may be modulated using the methods and bifunctional shRNAs described herein. For example, the invention provides that a first set of bifunctional shRNAs may be designed to include a sequence (a guide strand) that is designed to reduce the expression level of a first target gene, whereas a second set of bifunctional shRNAs may be designed to include a sequence (a guide strand) that is designed to reduce the expression level of a second target gene. The different sets of bifunctional shRNAs may be expressed and reside within the same, or separate, preliminary transcripts. In certain embodiments, such multiplex approach, i.e., the use of the bifunctional shRNAs described herein to modulate the expression level of two or more target genes, may have an enhanced therapeutic effect on a patient. For example, if a patient is provided with the bifunctional shRNAs described herein to treat, prevent, or ameliorate the effects of cancer, it may be desirable to provide the patient with two or more types of bifunctional shRNAs, which are designed to reduce the expression level of multiple genes that are implicated in the patient's cancer.

In certain embodiments, the invention further provides that the bifunctional shRNA sequences may comprise stem sequences of naturally occurring miRNAs (e.g., miR-30, C. elegans let-7 and/or lin-4). While the presence of a miR-30 loop, for example, may be desirable, the invention provides that variations of that structure may be tolerated, wherein loops may be used that are greater than 72%, preferably greater than 79%, more preferably greater than 86%, and most preferably, greater than 93% identical to, for example, the miR-30 sequence (determined using well-known computer programs such as the BESTFIT program (Wisconsin Sequence Analysis Package, Version 8 for Unix, Genetics Computer Group, University Research Park, 575 Science Drive, Madison, Wis. 53711)).

The precursor sequences (or constructs) encoding the bifunctional shRNAs may be introduced into host cells using any of a variety of techniques and delivery vehicles well-known in the art. For example, infection with a viral vector comprising one or more constructs may be carried out, wherein such viral vectors preferably include replication defective retroviral vectors, adenoviral vectors, adeno-associated vectors, lentiviral vectors, or measle vectors. In addition, transfection with a plasmid comprising one or more constructs may be employed. Such plasmids may be present as naked DNA, or may be present in association with, for example, a liposome (e.g., an immunoliposome). Still further, the delivery vehicle may consist of immunolipoplexes, targeted nanoparticles, targeted liposomes, cyclodextrins, nanoparticles, aptamers, dendrimers, chitosan, or pegylated derivatives thereof. The nature of the delivery vehicle may vary depending on the target host cell.

In-vivo delivery of the bifunctional shRNA-encoding constructs may be carried out using any one of a variety of techniques, depending on the target tissue. Delivery may be, for example, achieved by direct injection, inhalation, intravenous injection or other physical methods (including via micro-projectiles to target visible and accessible regions of tissue (e.g., with naked DNA). Administration may further be achieved via syringe needles, trocars, canulas, catheters, etc., as appropriate.

In addition to the methods of using the bifunctional shRNAs described herein, provided for are shRNAs themselves. Accordingly, additional aspects include nucleic acid sequences, which may comprise a single contiguous sequence or multiple distinct sequences that, individually or collectively, encode two or more RNA molecules. According to such embodiments, a first RNA molecule will comprise a double stranded sequence that includes a guide strand sequence that is complementary to a portion of an mRNA transcript encoded by a target gene, whereas a second RNA molecule comprises a second double stranded sequence that includes a second guide strand sequence that is partially complementary to a portion of such mRNA transcript. Preferably, the second guide strand sequence of the second RNA molecule comprises one or more bases that are mismatched with a nucleic acid sequence of the mRNA transcript encoded by the target gene. According to further aspects, expression vectors are provided which comprise the nucleic acid sequences, and may be used to carry out the methods, and express the bifunctional shRNAs, described herein.

Still further, methods of using the nucleic acid sequences and bifunctional shRNAs are described herein to prevent, treat and/or ameliorate the effects of one or more medical conditions, including without limitation various types of cancer. For example, the invention provides that the bifunctional shRNAs described herein may be used to reduce the expression level of one or more target genes that are implicated in cancer cell growth, survival, and/or metastasis. For example, as demonstrated in the Examples below, the bifunctional shRNAs may be used to reduce the expression level of certain target genes that encode scaffold proteins, which have been found to be over-expressed in cancer cells. Non-limiting examples of such target genes include Stathmin-1, RACK-1, Annexin II, and others.

The bifunctional shRNAs may further be used, for example, to reduce the expression level of pro-inflammatory genes or anti-apoptosis genes where therapeutically desirable. For example, expression of BCL-2 or acid ceramidase has been found to render tumor cells resistant to chemotherapy.

STMN1 is a protein composed of 149 amino acids organized into four domains (I-IV) as defined by limited proteolysis (Charbaut, Curmi et al. 2001). The core region (amino acids 42-126) is the minimum fragment required for tubulin interaction with the additional requirement of either an N- or C-terminal extension (Cassimeris 2002). There are four phosphorylation domains, designated as Ser 16, 25, 38 and 63 (Beretta, Dobransky et al. 1993; Larsson, Marklund et al. 1997). Of the four phosphorylation sites, only Ser 16 is conserved throughout the STMN1 family. Domain I which contains three of the four phosphorylation sites (Ser 25, 38 and 63) is known to have a polyproline II helix in the vicinity of the Ser 38 phosphorylation site (Redeker, Lachkar et al. 2000; Wallon, Rappsilber et al. 2000). Analysis of the 5'-flanking sequence of the STMN1 gene reveals multiple transcription factor recognition sequences: two AP-2 sites, five GC boxes (consistent with Sp1 consensus sequences), and four E2F sites (Larsson, Marklund et al. 1997; Gavet, Ozon et al. 1998; Cassimeris 2002).

Modulation of STMN1 (Nemunaitis, Senzer et al. 2007) can result in mitotic arrest, thereby exhibiting a critical role in microtubule dynamics. Microtubules are protein polymers comprised of α/β tubulin heterodimers which contribute to and are essential for the structure and function of the cell. These functions include intracellular transport, cell motility, and polarity. Microtubules extending from the centrosomes are captured at their plus ends by the chromosomes thereby forming the mitotic spindle. Spindle dynamics can best be described as an alternating pattern of stabilization and destabilization. Stathmin mediated destabilization can result from either tubulin sequestration or "catastrophe". The latter results from microtubule depolymerization and is counterbalanced by "rescue" which is effected by polymerization. The transition between the two phases during the various portions of the cell cycle is regulated by microtubule-stabilizing and microtubule-destabilizing proteins (Mitchison and Kirschner 1984; Desai and Mitchison 1997; Mistry, Bank et al. 2005). The process of mitotic spindle formation is a coordinated, balanced interaction between the stabilizing activities of microtubule associated proteins (XMAP215, EB1), motor proteins (predominantly kinesin, e.g., Eg-5), and plus-end depolymerases including XKCM1, MCAK and STMN1 (Andersen 2000; Niethammer, Kronja et al. 2007). A tightly regulated sequenced pattern of STMN1 phosphorylation and de-phosphorylation is necessary for entry into prophase and, terminally, into cytokinesis, respectively (Cassimeris 2002).

During mitosis, microtubule dynamics favoring spindle formation proceeds via the inhibition of stathmin-tubulin binding. The binding of stathmin to two molecules of tubulin (T2S) is inhibited by sequential phosphorylation steps, which terminate depolymerization activity. Phosphorylation of one or two sites (Ser 25 or Ser 38) by CDK1 (p34cdc2) or MAPK is necessary but not sufficient for inhibition of stathmin-tubulin binding. Monophosphorylation and biphosphorylation of stathmin is prevalent during the S phase of the cell cycle, while triphosphorylation is abundant at the G2M boundary (Andersen 2000). All four residues are normally phosphorylated throughout the M phase. A final phosphorylation of Ser 16 and 63 is required for the overall inactivation of stathmin-tubulin binding (Andersen 2000; Honnappa, Jahnke et al. 2006). This may, in part, be a result of Aurora B kinase (Aur-B) which is localized to the interphase chromosome proximal to the centromere, inhibits MCAK activity, and has a consensus site on Ser 16 (Gadea and Ruderman 2006). Additionally, EGF can contribute to Ser 16 phosphorylation via Rac/Cdc42 and p65PAK-dependent activity as well as the cAMP-dependent kinase A and the Ca2+/calmodulin-dependent kinase isoforms CaMK IV/Gr and CaMKII (Daub, Gevaert et al. 2001; Wittmann, Bokoch et al. 2004). Next, it has been postulated but not yet convincingly demonstrated that during the metaphase to anaphase transition, stathmin effects poleward kinetochore spindle movement by increasing minus-end catastrophe frequency (Manna, Thrower et al. 2006). The functional relevance of this purportedly pH-dependent mechanism has been recently evaluated and brought into question by Steinmetz (Steinmetz 2007). However, it has now been shown that exogenous STMN1 does indeed affect metaphase-to-anaphase transition by its role in kinetochore-associated microtubule detachment during anaphase thereby resulting in chromosomal instability with over a 100-fold increase in micronucleus formation (Holmfeldt, Sellin et al.). In order to exit mitosis and allow for cytokinesis, the microtubules undergo depolymerization, which requires the dephosphorylation of stathmin reactivating its tubulin binding property. In K562 cells, study of the exit from mitosis suggest that stathmin is dephosphorylated by an okadaic acid-sensitive phosphatase(s) (see FIG. 27) (Mistry and Atweh 2001).

The decreased expression of p27 in a number of tumor types has been linked to prognosis including metastatic potential (Slingerland and Pagano 2000). Besides being a CDK inhibitor of Cyclin D1, p27 has been shown to play a role in cell motility (Baldassarre, Belletti et al. 2005). Baldassare recently showed that stathmin is a p27 binding partner and on the basis of his data postulates that p27 interferes with stathmin binding and sequestration of tubulin, consequently inhibiting cell motility and microtubule depolymerization. Furthermore, p27 is downregulated in transformed cells, and he showed that low p27 and high STMN1 correlate with the metastatic behavior of sarcoma cells in vivo (Baldassarre, Belletti et al. 2005). Similar results are seen in gastric cancer (Jeon, Han et al. 2010), colorectal cancer (Zheng, Liu et al. 2010), NSCLC (Singer, Malz et al. 2009), and glioblastoma (Liang, Choi et al. 2008).

Stathmin is highly expressed in a variety of assessed human malignancies including acute leukemia (Hanash, Strahler et al. 1988; Melhem, Zhu et al. 1991; Brattsand, Roos et al. 1993; Ghosh, Anderson et al. 1993; Luo, Mookerjee et al. 1994), lymphoma (Brattsand, Roos et al. 1993; Ghosh, Anderson et al. 1993; Nylander, Marklund et al. 1995), Wilms tumor (Takahashi, Yang et al. 2002), ovarian carcinoma (Balachandran, Welsh et al. 2003), prostate cancer (Mistry, Bank et al. 2005; Mistry and Atweh 2006), breast cancer (Brattsand 2000; Alli, Bash-Babula et al. 2002; Alli, Yang et al. 2007), head and neck cancer (Kouzu, Uzawa et al. 2006), hepatocellular carcinoma (Yuan, Jeng et al. 2006), osteosarcoma (Zhang, Gao et al. 2004), lung cancer (Nishio, Nakamura et al. 2001; Chen, Wang et al. 2003; Rosell, Scagliotti et al. 2003), and mesothelioma (Kim, Harvard et al. 2007). For example, using 2D PAGE, Chen (Chen, Wang et al. 2003) evaluated stathmin expression in 93 lung adenocarcinoma specimens compared to 10 uninvolved samples and found that stathmin expression was significantly elevated in the poorly differentiated versus moderately and well differentiated tumor cells. Protein overexpression correlated with Affymetrix mRNA expression. Furthermore, in 86 of these tumor specimens, a set of genes were found that correlated with stathmin mRNA, specifically, and were also found, not unexpectedly, to be predominantly associated with tubulin or the cytoskeleton (Chen, Wang et al. 2003).

A variety of target specific anti-stathmin effectors including ribozymes (Mistry, Benham et al. 2001) and siRNA (Zhang, Wang et al. 2006; Alli, Yang et al. 2007) have been used to silence stathmin in vitro as singlets (Mistry, Benham et al. 2001; Zhang, Wang et al. 2006; Alli, Yang et al. 2007) and in combination with chemotherapeutic agents where additive to synergistic interactions have been demonstrated, for example, with the taxanes (Mistry and Atweh 2006; Ngo, Peng et al. 2007; Wang, Dong et al. 2007). Both ribozyme and siRNA inhibition of stathmin mRNA result in an increase in G2M phase cell population, an inhibition of clonogenicity, and a marked increase in apoptosis (Iancu, Mistry et al. 2001; Zhang, Wang et al. 2006; Alli, Yang et al. 2007). The latter may be due to the effect of modulation of microtubule network mobility on the proportion of Bax/Bcl-2 and Bax/Bcl-xL heterodimers (Longuet, Serduc et al. 2004; Singer, Ehemann et al. 2007).

RNA Interference: The introduction of artificial double-stranded small interfering RNAs (siRNAs) into animal and plant cells can induce the degradation of targeted mRNA molecules with complementary sequence; the process is known as RNA interference (RNAi) (Sharp 2001; Hutvagner and Zamore 2002; Zamore 2002) (see U.S. Pat. No. 6,506,559). RNAi has emerged as a useful experimental tool with strong potential for therapeutic applications (Fire, Xu et al. 1998; Hammond, Bernstein et al. 2000; Elbashir, Harborth et al. 2001; Senzer, Rao et al. 2009; Wang Z 2011). However, in mammalian cells, induction of RNAi using shRNAs requires the transfection of RNA oligonucleotides, which can be inefficient with the duration of effective silencing limited by vehicle disassembly time and siRNA biologic half life. Despite these limitations, in a recent early results publication of a clinical phase I study, Davis and colleagues have convincingly demonstrated target specific silencing and site-specific cleavage with systemic delivery of a pegylated, transferrin decorated, cyclodextrin-based siRNA targeting the M2 subunit of ribonucleotide reductase (RRM2) (CALAA-01) (Davis, Zuckerman et al. 2010). Three reported patients with biopsy accessible melanoma, who were treated as per the dose-escalation Phase I study, received 18, 24, or 30 mg/m2 CALAA-01 by intravenous infusion on days 1, 3, 8, and 10 of a 21 day cycle. Voluntary biopsies were performed after the final dose of cycle 1 in each and compared to archived tumor, and at 1 month post cycle 1 (prior to initiation of cycle 2) and on the day of the final dose of cycle 2 in the patient treated at 30 mg/m2. RRM2 mRNA reduction was confirmed by qRT-PCR comparing post- and pre-cycle 2 tissue samples at 30 mg/m2. In the same patient, immunohistochemistry and Western blot pre- and post-cycle 1 showed a five-fold reduction in MMR2 protein. Supporting the proposed mechanism of action, 5'-RLM-RACE (5'-RNA-ligase-mediated rapid amplification of complementary DNA ends) confirmed the predicted cleavage site. This first-in-human demonstration of targeted tumor cell entry (using transmission electron microscopy) and mRNA and protein expression reduction along with predicted site-specific siRNA cleavage following systemic delivery brings added impetus to translational application of RNAi.

siRNA requires chemical modification to increase serum stability, cellular uptake and duration of action. Alnylam has employed chemically modified siRNA to treat a variety of diseases, including liver cancer. Chemically modified siRNA was formulated with a proprietary LNP lipoplex, which delivered more than 90% of lipoplex to the liver according to Alnylam's study reports. Two modified siRNAs targeting either the kinesin spindle protein or vascular endothelial growth factor were formulated together with proprietary LNP technology and systemically administered by IV infusion. This RNAi therapy was positioned to treat advanced solid tumors with liver involvement due to high delivery efficiency of LNP to the liver. However, for effective therapy of metastatic foci, it will be critically important to deliver RNAi effector molecules to other organs in addition to the liver. Thirty-one patients with multiple prior therapies, a majority of them with colorectal cancer, were administered ALN-VSP02 with doses ranging from 0.1 to 1.5 mg/kg. This treatment was generally well-tolerated and no dose-dependent changes in liver function tests were reported 46.6% of patients (7/15) had stable disease (SD) for at least 2 months at dose ≥0.7 mg/kg, compared with 8.3% (1 of 12) with SD at doses ≤0.4 mg/kg. Cleavage of VEGF mRNA was identified in two liver tumor biopsies and one extrahepatic tumor. Pharmacologically relevant concentrations (0.3-142 ng/g tissue) of both VEGF and KSP siRNAs were detected in tumor biopsies (Cervantes, Alsina et al. 2011). Phase I trial is completed with trial extension providing treatment to those patients responded to the treatment.

Alternatively, siRNA can be constructed as a short hairpin RNA (shRNA). shRNA consists of a stem-loop structure that can be transcribed in cells from RNA polymerase III (or, less frequently used, RNA polymerase II) promoter on a plasmid construct (Miyagishi and Taira 2002; Yu, DeRuiter et al. 2002). Constitutive expression of shRNA from a plasmid independently from the chromosome provides an advantage over synthetic siRNA. The shRNA expression units can be incorporated into a variety of plasmids and viral vectors for intracellular delivery and nuclear import. In addition, vector based shRNA expression can also be regulated or induced (Gossen and Bujard 1992; Gupta, Schoer et al. 2004; Dickins, Hemann et al. 2005). shRNAs, as opposed to synthetic siRNAs, are synthesized in the nucleus of cells, then processed and transported to the cytoplasm to be incorporated into the RNA-induced silencing complex (RISC) for activity (Cullen 2005). To be effective, shRNA has to be designed to utlize the endogenous cellular microRNA biogenesis machinery.

Bifunctional shRNA: As described above, RNA interference (RNAi) is a natural cellular regulatory process capable of inhibiting transcriptional, post-transcriptional and translational mechanisms thereby modulating gene expression. Using a miR30-scaffold, the present inventors developed a "bifunctional" RNAi strategy which demonstrated more effective silencing of target gene expression by concurrently inducing translational repression, and [GW182-mediated] sequestration in the p-body (as a holding reservoir or promoting decapping, deadenylation and mRNA degradation) (cleavage-independent) as well as post-transcriptional mRNA mRNA cleavage (cleavage dependent) (Rao D 2010).

Stathmin 1 (STMN1) was selected as a target from a series of differentially overexpressed mRNA and protein couplet signals in tumor/normal tissue specimens obtained from cancer patients (Nemunaitis, Senzer et al. 2007; Shen Y 2008).

The pbi-shRNA™ STMN1 vector was designed to mimic the framework of human pre-miRNA hsa-miR-30a by substituting the mature miRNA sequence with STMN1 specific siRNA sequence at the stem region of the stem-loop structure. Two modifications were made to further improve the efficiency of processing and maturation of shRNAs. First, the loop region of miR-30a was enlarged to 15 bases for more efficient Drosha processing from pri-miRNA to pre-miRNA. Second, two nucleotides in 3' juxtaposition to the STMN1 specific siRNA sequence were modified for improved efficient processing of the pre-miRNA to mature miRNA.

Figure 1:
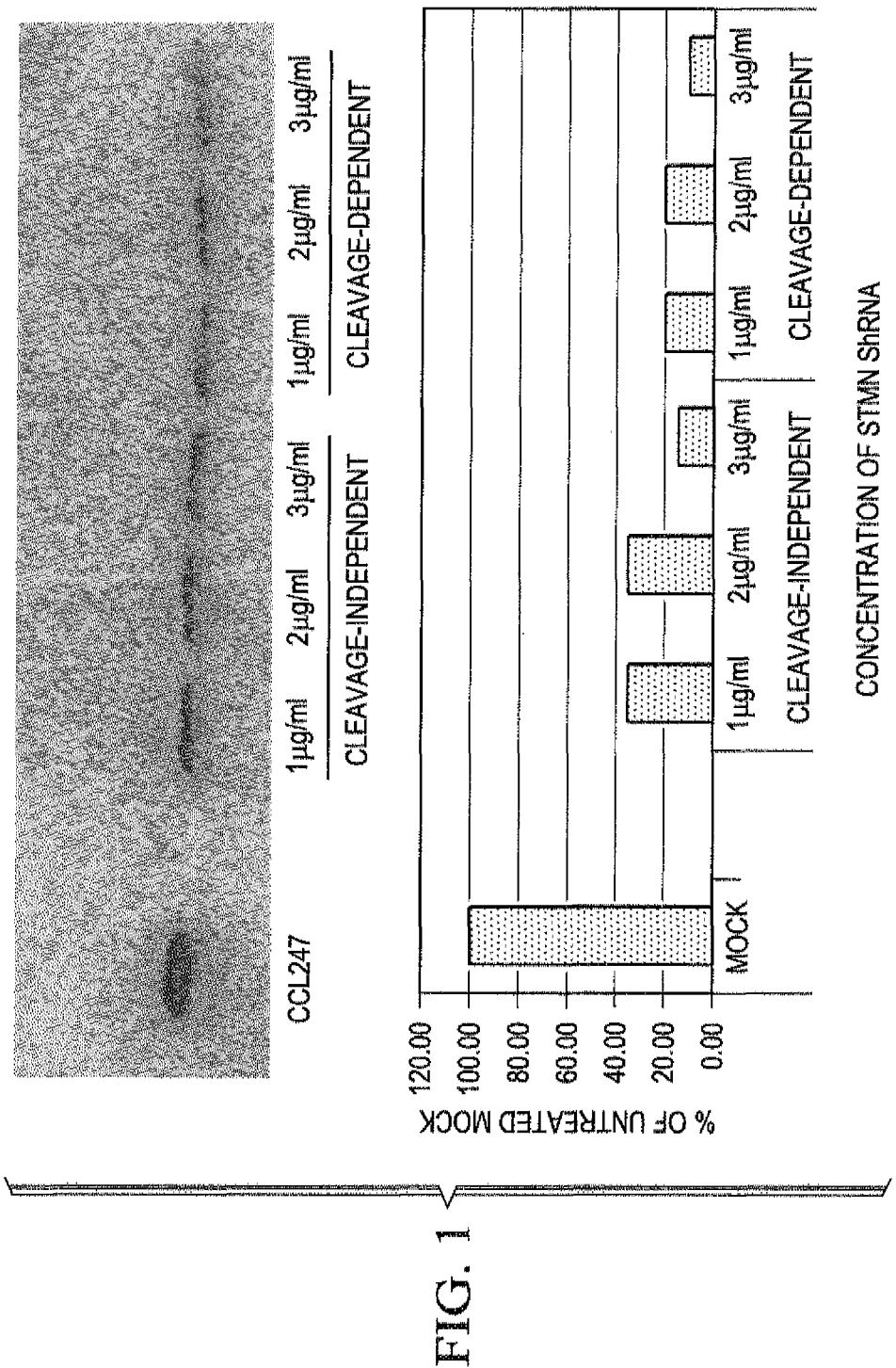
FIG. 1 illustrates that both cleavage-dependent and cleavage-independent components of the pbi-shRNA™ STMN1 are able to mediate STMN1 knockdown. Total CCL247 cell protein were harvested 48 hours post-transfection and analyzed for STMN1 protein expression by Western immunoblot analysis with STMN1 specific antibody. The STMN1 protein expression from transfected cells were compared to mock-transfected cells.

The expression unit for the bifunctional shRNA to Stathmin1 (pbi-shRNA™ STMN1) is inserted between the Sal I and Not I sites of expression vector pUMVC3 (FIG. 25) and is driven from an enhanced CMV IE promoter (A RNA polymerase II promoter). It contains two stem-loop structures in a miR-30 backbone, one with complete matching passenger and guide strands (cleavage-dependent; siRNA-like component), and the other with two base-pair mismatches between passenger and guide strands (cleavage-independent; miRNA-like component). The GC to AU switches are at positions 11 and 12 of the passenger strand which create mismatches at the central location similar to most miRNAs (FIG. 26).

pbi-shRNA™ STMN1 is able to Knockdown STMN1 Expression: The individual components of the pbi-shRNA™ STMN1 were tested for STMN1 knockdown. Colon cancer cell line CCL247 cells were transfected with three concentrations of expression vectors (1 ug/ml, 2 ug/ml or 3 ug/ml) expressing either cleavage-dependent shRNA (pGBI 1) or cleavage-independent shRNA (pGBI 3) for STMN1. All three concentrations of both constructs were able to substantially knockdown STMN1 expression in CCL247 cells within 48 hours (FIG. 1).

Figure 2A:
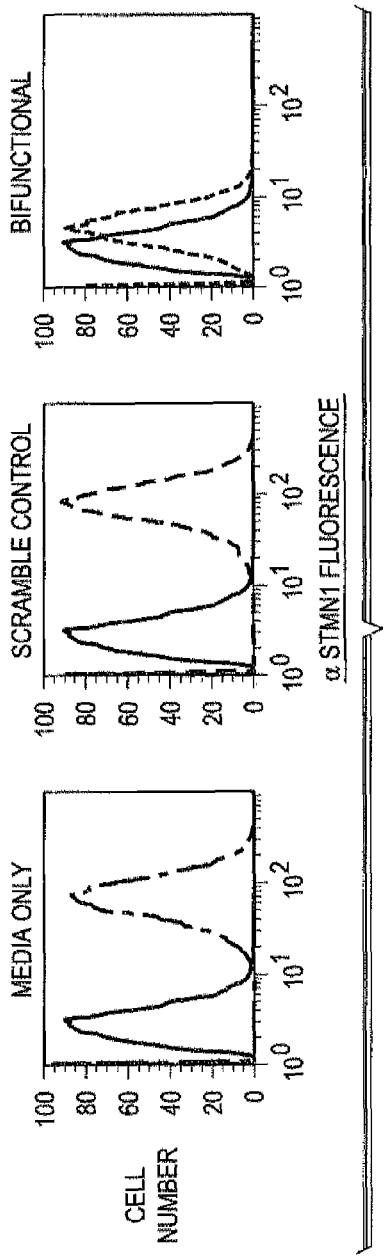
FIG. 2 shows that pbi-shRNA STMN1 effectively reduced STMN1 protein expression in CCL-247 cells. CCL-247 cells were transfected with 3.6×10-13 M of the bi-sh-STMN1. 24 hours after transfection, transfected cells were harvested for flow immunophenotyping analyses, using STMN specific primary antibody (a) or β-actin specific primary antibody (b). The antibody-reacted cells were analyzed by flow cytometry following incubation with a fluorescene (phycoerythrin) conjugated goat anti-mouse secondary antibody. Black lines: no primary antibody; Red lines: STMN1 expression in media only (STMN1 or non-transfected); Green lines: STMN1 expression in cells transfected with scramble shRNA control; Blue lines: STMN1 expression in cells transfected with pbi-shRNA™ STMN1. Shift in MFI in STMN1 expression (A). No shift in β-actin expression (B).
Figure 2B:
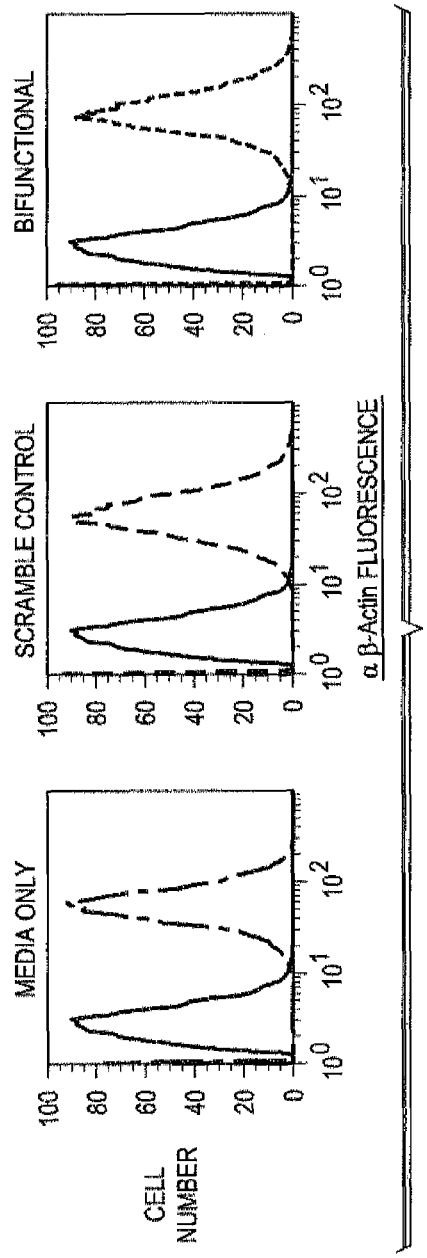

Following transfection of pbi-shRNA™ STMN1, CCL-247 cells were analyzed for STMN1 expression by flow immunophenotype analyses. Transfected cells demonstrated 93% reduction of STMN1 protein (shift in mean fluorescence intensity/MFI, FIG. 2b) compared to untransfected or scrambled controls, while β-actin expression was not changed (FIG. 2a).

Rats are a Bio-Relevant Species for Safety Evaluation of pbi-shRNA™ STMN1 LP: The sequence comparison at bi-shSTMN1 target site for human and for rat is as follows:

```
Human:
                              (SEQ ID NO: 1)
GGCACAAATGGCTGCCAAA (Ref. Seq. # NM_005563)

Rat:
                              (SEQ ID NO: 2)
GGCGCAAATGGCTGCCAAG (Ref. Seq. # NM_017166)
```

For the target site, there is 89.5% (17/19) nucleotide sequence homology between human and rat with two A to G mismatches at position 4 and 19 of passenger strand (or position 1 and 16 of guide strand). siRNA with single mismatch at each position of the guide strand was systematically examined and it was shown mismatches at position 1 or 16 of the guide strand do not adversely affect the knockdown efficiency of siRNA (Schwarz, Ding et al. 2006). Data present in this document with rat mRNA and rat cell lines further confirms and illustrates that the bifunctional shRNA to human STMN1 does knockdown rat STMN1 (Section 1.10).

STMN1 expression profile in human and rats are very similar. Provided are STMN1 tissue expression profiles for human and for rat (Tables 1-2). Data was compiled from NCBI's UniGene/EST database for human STMN1 (HS209983) and rat STMN1 (RN555). Each data point is number of Expressed Sequence Tags (ESTs) for the gene per one million total EST count in each tissue. The order of tissues is in descending order of STMN1 EST counts. Although the STMN1 tissue expression profile data compiled for rats were not as complete as for human, STMN1 is shown similarly expressed at medium level (compared with β-Actin) in major organs of rats as well as human. Furthermore, off-target analysis presented in Sections 1.9 and 1.10 shows that rats are bio-relevant species for safety evaluation of pbi-shRNA™ STMN1 LP.

Results of 2D DIGE and microarray are provided for STMN1 over-expression in 3 out of 3 melanoma patients tested at Mary Crowley Cancer Research Centers (Table 3). The STMN1 over-expression in melanoma of patients tested is at least 3.9 fold higher than normal skin. Nude rats with human melanoma cell lines over-expressing STMN1 xenograft provide bio-relevant tumor model (RE-PTL-135).

TABLE 1

EST/Million for Human Tissues

| Human | STMN1 | b-Actin |
|---|---|---|
| salivary gland | 1233 | 6067 |
| bladder | 1128 | 3783 |
| thymus | 1120 | 4582 |
| bone marrow | 732 | 3990 |
| skin | 666 | 4389 |
| uterus | 653 | 5825 |
| eye | 624 | 2269 |
| testis | 579 | 2326 |
| adrenal gland | 509 | 4018 |
| embryonic tissue | 509 | 4864 |
| ear | 489 | 1896 |
| heart | 454 | 2325 |
| bone | 445 | 2757 |
| umbilical cord | 436 | 15697 |
| blood | 435 | 7283 |
| nerve | 379 | 2338 |
| lymph | 360 | 8603 |
| brain | 340 | 4004 |
| pituitary gland | 298 | 896 |
| liver | 297 | 2466 |
| pharynx | 289 | 1614 |
| lung | 245 | 3696 |
| parathyroid | 242 | 290 |
| tonsil | 234 | 12146 |
| cervix | 226 | 6433 |
| mammary gland | 207 | 3177 |
| ascites | 199 | 6615 |
| ovary | 194 | 3741 |
| muscle | 166 | 804 |
| prostate | 157 | 2428 |
| intestine | 156 | 4806 |
| pancreas | 153 | 2466 |
| esophagus | 148 | 13655 |
| placenta | 144 | 2702 |
| stomach | 144 | 6314 |
| lymph node | 141 | 3133 |
| kidney | 131 | 3076 |
| connective tissue | 86 | 4278 |
| spleen | 74 | 6347 |
| mouth | 44 | 565 |
| trachea | 38 | 724 |
| thyroid | 20 | 6027 |
| adipose tissue | 0 | 4484 |
| larynx | 0 | 4083 |

TABLE 2

EST/Million for Rat Tissues

| Rat | STMN-1 | b-Actin |
|---|---|---|
| adrenal gland | 1012 | 2025 |
| eye | 888 | 3390 |
| dorsal root ganglion | 669 | 3152 |
| embryonic tissue | 464 | 3452 |
| pituitary gland | 353 | 1768 |
| heart | 324 | 649 |
| brain | 228 | 767 |
| spleen | 183 | 4039 |
| pancreas | 174 | 1686 |
| prostate | 158 | 3486 |
| connective tissue | 141 | 601 |
| placenta | 138 | 1565 |
| kidney | 133 | 1596 |
| thymus | 122 | 3428 |
| colon | 119 | 3945 |
| lung | 84 | 2632 |
| liver | 65 | 3642 |
| adipose tissue | 0 | 331 |
| ovary | 0 | 825 |
| pineal gland | 0 | 872 |
| small intestine | 0 | 1955 |
| testis | 0 | 246 |
| vibrissa | 0 | 4407 |
| muscle | 0 | 0 |
| nerve | 0 | 0 |

Table 3 shows 2D DIGE and Microarray of STMN1 overexpression in 3 out of 3 melanoma patients tested. STMN1 levels in tumor versus normal:

| Patient Number | Cancer Type | Fold ↑ in STMN1(mRNA) in tumor vs normal | Fold ↑ in STMN1 (Protein T/N ratio) in tumor vs normal |
|---|---|---|---|
| 1 | Melanoma | 21 | 7 |
| 2 | Melanoma | 3.9 | Not Done |
| 3 | Melanoma | 5.6 | 5.3 |

Normal = Normal tissue obtained from adjacent skin biopsy.

Detection of Product Effector Molecules (mature shRNAs) in the pbi-shRNA™ STMN1 transfected cells: Using an adapted stem-loop reverse transcription-polymerase chain reaction RT-PCR method (schematic illustration of the method is shown on FIG. 3) confirmed the presence of the predicted guide strand (FIG. 4a, black arrow). The guide strand sequence was able to be amplified from RNA isolated from cells transfected with both pbi-shRNA™ STMN1 and siRNA STMN1 (FIG. 4a, black arrow). An additional minor polymerase chain reaction (PCR) product was detected from the pbi-shRNA™ STMN1 transfected cells (FIG. 4a, red arrow) which was sequenced and shown to be a processing intermediate containing 11 bases of the miR30 stem.

Figure 4B:
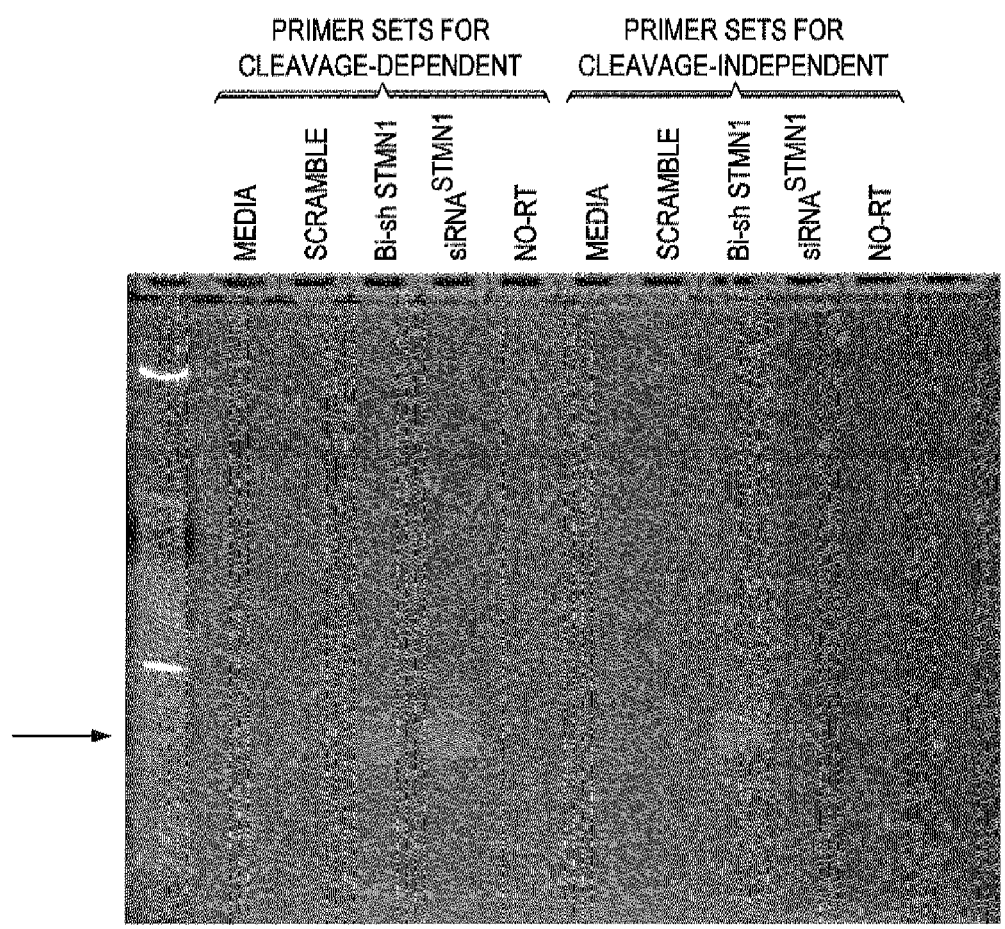
FIG. 4b shows a photo-image of agarose gel demonstrating the RT-PCR product of the passenger (sense) strand (black arrow). Total cellular RNA was first reverse-transcribed with passenger strand specific stem-loop RT primer and subsequently amplified with the passenger strand specific (either for the cleavage-dependent or cleavage-independent component) and stem-loop specific PCR primer set. PCR amplified product was run onto a 4% agarose gel and stained with ethidium bromide and visualized under UV light. Sequence of both PCR products were confirmed by Seq Wright.

Using primers specific for the matched and mismatched passenger strand, it was further confirmed that both matched and mismatched passenger strands were synthesized from the pbi-shRNA™ STMN1 transfected cells (FIG. 4b, black arrow). Both passenger strands were present in the pbi-shRNA™ STMN1 transfected cells, whereas only the fully matching passenger strand was detected from siRNA STMN1 transfected cells.

Figure 5:
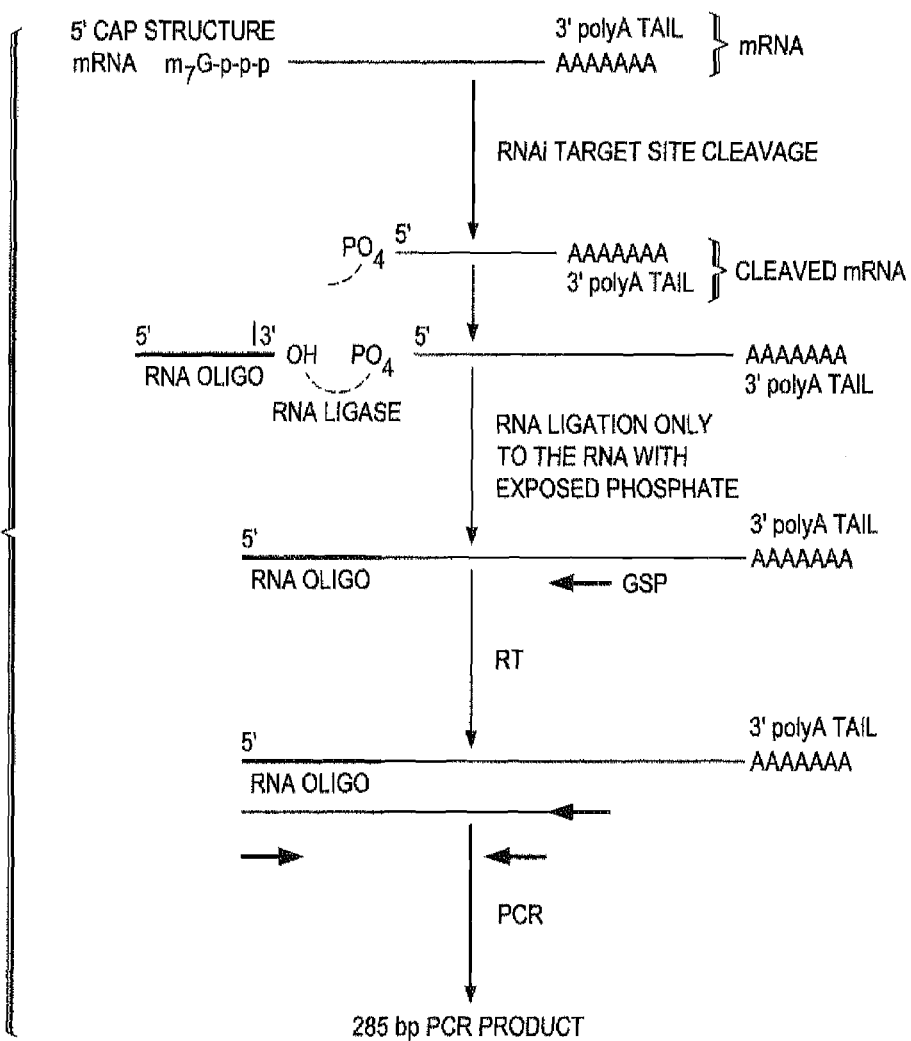
FIG. 5 shows a diagram illustrates RNA Ligase Mediated 5' Rapid Amplification of cDNA Ends (RLM-RACE) assay for RNAi mediated cleavage product. Schematic diagram using RACE method to detect target site-specific cleavage product. RNA oligo was ligated onto the 5' end of cleaved mRNA. cDNA was synthesized with a gene specific primer (GSP) and further amplified with the gene specific primer and primers specific for the RNA oligo. The primers specific for STMN1 mRNA, predicted the RLM-RACE product at 285 base pairs.
Figure 6:
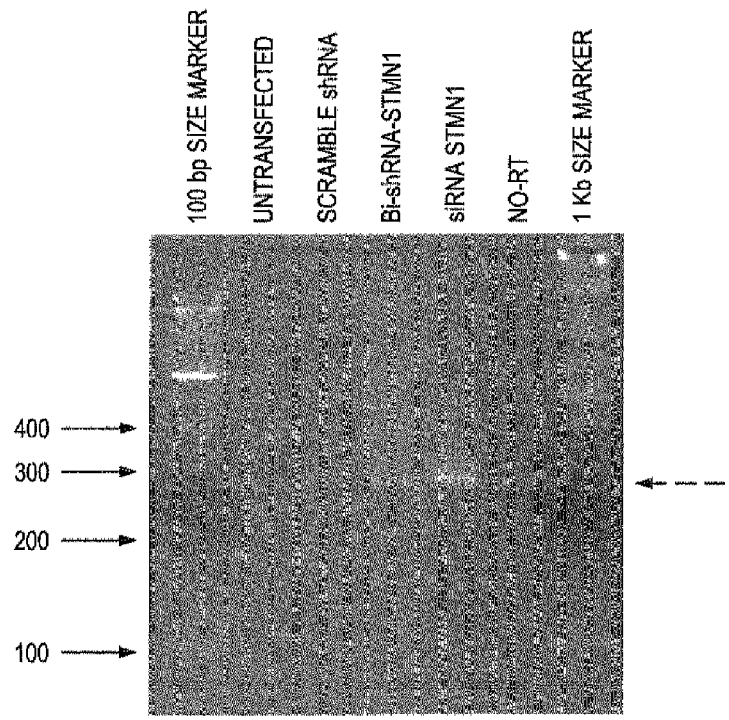
FIG. 6 shows that STMN1 mRNA target site cleavage is detected from the pbi-shRNA™ STMN1 transfected CCL-247 cells by RLM-RACE. Photo-image of agarose gel resolving RACE PCR products. RACE PCR product was detected in cells transfected with either pbi-shRNA™ STMN1 or siRNA STMN1. CCL-247 cells were transfected with 7.22× 10-13M of pbi-shRNA™ STMN1 (lane 4), or 30 nM of siRNA (lane 5); a 285 base pairs PCR product was detected (red arrow). Lane 1 is 100 bp size markers, lane 2 is RNA from un-transfected cells. Lane 3 is RNA from scrambled shRNA transfected cells. Lane 6 is PCR only control. Lane 7 is 1 kb size markers.

Validation of Target Site Cleavage: The modified 5' Rapid Amplification of cDNA Ends (5'RACE) method also known as RNA Ligase mediated RACE (RLM-RACE) was utilized to detect the site of siRNA component mediated target cleavage (schematic illustration of the method is shown on FIG. 5) (Soutschek, Akinc et al. 2004). Gene-specific primers were designed both for reverse transcription (RT) and for PCR. For PCR, also the gene specific nested primer strategy was used to reduce any non-specific background. The predicted RLM-RACE PCR product was detected in cells transfected with both pbi-shRNA™ STMN1 and siRNA STMN1, respectively (FIG. 6, red arrow). The PCR product was sequence confirmed to be at the middle of the target site sequence.

Figure 7:
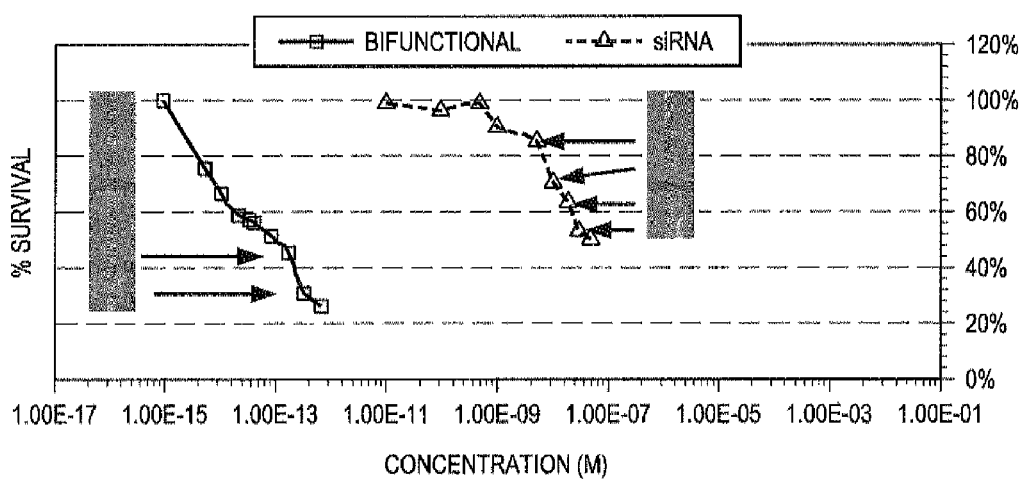
FIG. 7 shows a dose response curve for pbi-shRNA™ STMN1 (purple) and siRNA STMN1 (yellow) correlated with STMN mRNA cleavage (5' RACE assay). The x-axis is increasing dose of plasmid concentration from left to right. The y-axis is percent cell survival after 24 hours of treatment. Each data point represents the average of triplicate of samples with standard deviation. The concentration ranges for pbi-shRNA™ STMN1 and siRNA STMN1 varied from $1.44 \times 10^{-12}$M to $5.63 \times 10^{-15}$M and from $5 \times 10^{-7}$M to $1 \times 10^{-10}$M, respectively. Electropherogram inserts show deleted 5' RACE product.

Cancer Cell Growth Inhibition by pbi-shRNA™ STMN1: To compare the functional effectiveness of pbi-shRNA™ STMN1 to siRNA STMN1, CCL-247 growth inhibition was assessed over a concentration range of both moieties allowing for generation of respective dose response curves. The pbi-shRNA™ STMN1 resulted in significantly greater cell kill than siRNA STMN1 (p=0.004) (FIG. 7); IC50 of the former at $2.25 \times 10^{-14}$M more than 5 logs higher than the later $1 \times 10^{-8}$M. The target specific cleavage product, as demonstrated by 5'-RACE, was detected at essentially all siRNA STMN1 concentrations, but only detected at the higher dose of pbi-shRNA™ STMN1 thereby demonstrating the additional functional contribution of the non-cleavage dependent component mechanism of the latter (FIG. 7).

The pbi-shRNA™ STMN1 is more effective than siRNA STMN1, and pshRNA STMN1 with single component; STMN1 mRNA Knockdown Kinetics comparison: Data are shown that each component of the bi-functional design is able to knockdown the expression of STMN1, and further data are presented that pbi-shRNA™ STMN1 has strong advantage over the single component constructs only with single component of the bi-functional design. Two additional vectors were constructed in the same vector backbone and miR30 scaffold to compare cleavage dependent and independent activity to the bifunctional construct (FIG. 8). By 48 hours post transfection, pGBI-1 (cleavage-dependent component only) rapidly induced STMN1 mRNA knockdown reached steady-state and was lower by 72 hours. pbi-shRNA™ STMN1 (with both cleavage-dependent and -independent motifs) steadily reduced STMN1 mRNA through 72 hours. pGBI-3 (cleavage-independent component only) is designed to load on to cleavage-independent RISC/Ago complexes and act through translation inhibition and mRNA sequestration in the P-body. Following treatment with pGBI-3, STMN1 mRNA was more abundant at 24 and 48 hours (presumbably mRNA sequestration) compared to the un-treated cells and started to decline after 72 hours post-transfection in agreement with postulated mechanisms but well below activity of pbi-shRNA™ STMN1.

Figure 9:
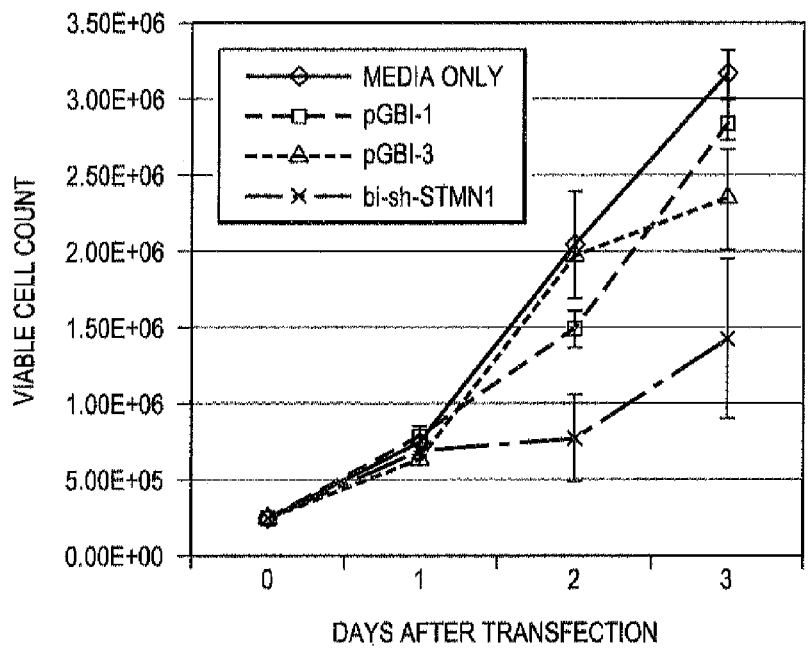
FIG. 9 shows the result of CCL-247 cells treated with $2.26 \times 10^{-14}$M of constructs.
Figure 10:
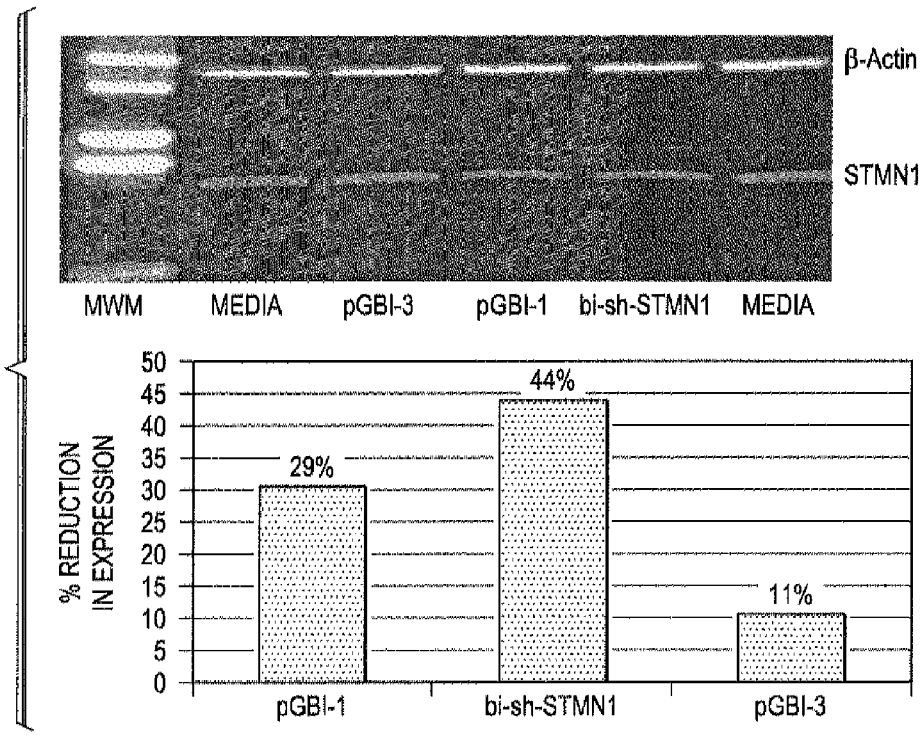
FIG. 10 shows comparison of STMN1 protein knockdown in CCL-247 cells 48 hours after treatment with $2.26 \times 10^{-14}$ M of constructs. The specificity of the anti STMN1 antibody and anti β-actin antibody was confirmed by western immunoblot analysis. Percent reduction in STMN1 expression was compared to media control and normalized to β-Actin expression level.

Growth inhibition comparison: To further validate the growth inhibitory potential of the pbi-shRNA™ STMN1 (pGBI-2) in comparison to each of its individual cleavage-dependent (pGBI-1) and cleavage-independent components (pGBI-3), reverse transfection of CCL-247 cells was performed at three different concentrations for each construct and cancer cell growth inhibition was monitored for up to three days in culture. Notably, pbi-shRNA™ STMN1 exposure at the lowest concentration ($2.26 \times 10^{-14}$ M) demonstrated a significant difference in lethality compared to the individual cleavage dependent (pGBI-1) and independent (pGBI-3) components over the three day period (p>0.001, pbi-shRNA™ STMN1 vs. pGBI-1; p>0.001, pbi-shRNA™ STMN1 vs. pGBI-3) (FIG. 9). Western immunoblot studies from 48 hr samples further correlated the knockdown advantage by pbi-shRNA™ STMN1 (FIG. 10).

Figure 11A:
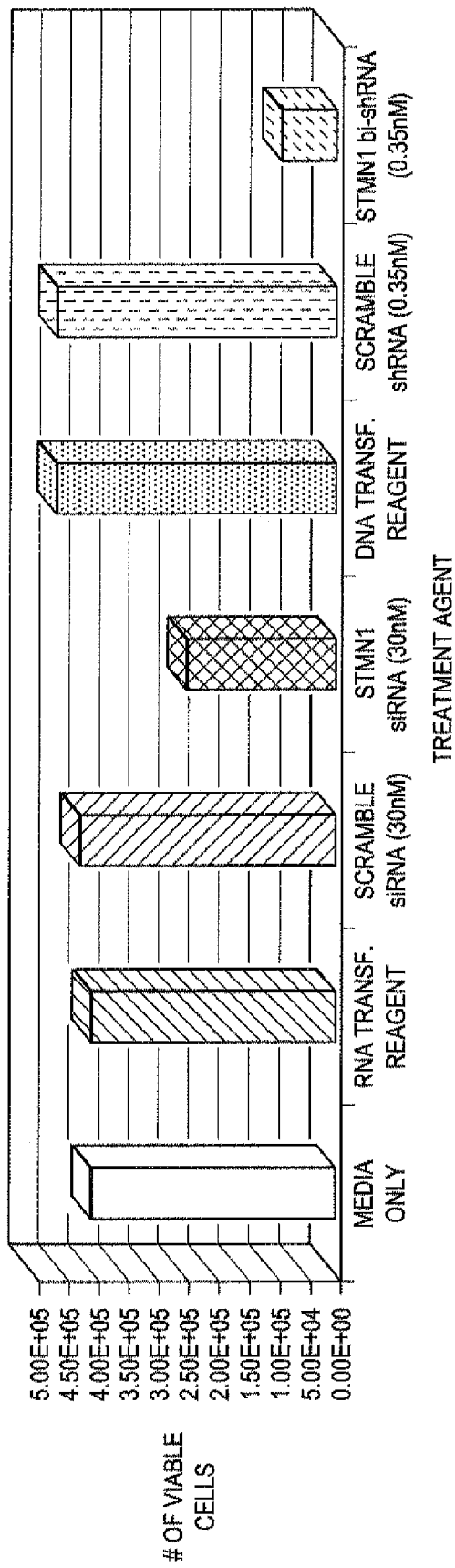
FIG. 11a shows that treating melanoma cell line MDA-MB-231 cells with pbi-shRNA™ STMN1 resulted in inhibition of cancer cell growth.
Figure 11B:
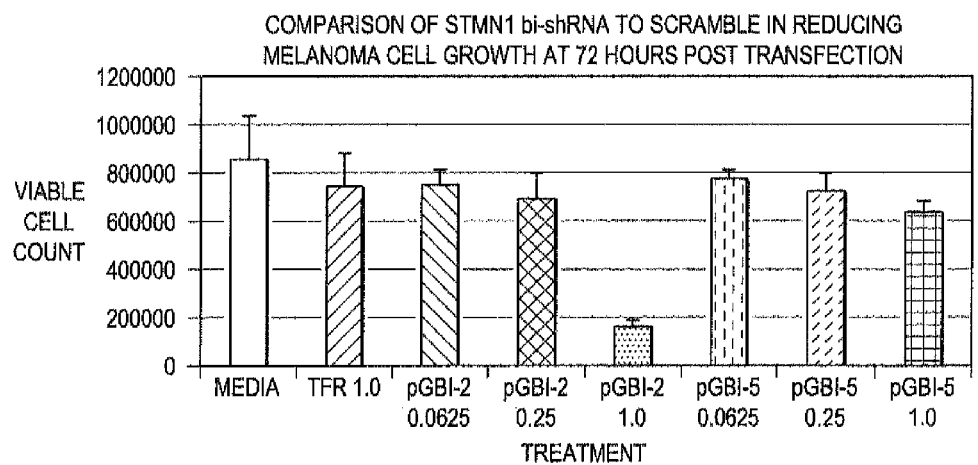
FIG. 11b shows that treating melanoma cell line SK-MEL-28 cells with pbi-shRNA™ STMN1 resulted in inhibition of cancer cell growth. SK-MEL-28 cells were transfected with 1 ug/ml, 0.25 ug/ml, or 0.0625 ug/ml of either the pbi-shRNA™ STMN1 (dark purple bar, light turquoise bar and yellow bar, respectively) or scrambled shRNA vector (light purple bar, dark blue bar and orange bar, respectively). At 72 hours post transfection, viable cells were counted for each culture and compared with media only (blue bar) and transfection reagent only (purple bar).

The pbi-shRNA™ STMN1 can also effectively result in growth arrest of melanoma (SK-MEL-28) and breast cancer (MDA-MB-231) cells in culture: The pbi-shRNA™ STMN1 construct was further tested for its effectiveness in inducing cancer cell growth arrest with breast cancer cell line (MDA- MB-231) or with melanoma cell line (SK-MEL-28). With 1 ug/ml of the pbi-shRNA™ STMN1, MDA-MB-231 (FIG. 11a) and SK-MEL-28 (FIG. 11b) cell growth was effectively inhibited.

Figure 12:
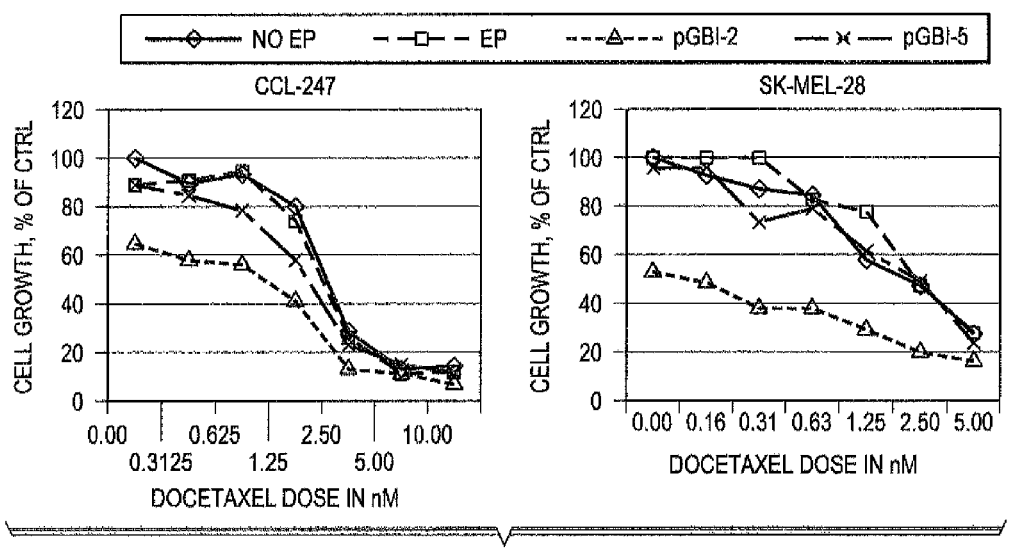
FIG. 12 shows additive anti-tumor response to stathmin (STMN) knockdown and docetaxel. Representative findings are shown for the combined antitumor activity of nucleofection of pbi-shRNA™ STMN1 and docetaxel in the colorectal line CCL-247 (left panel) and the melanoma line SK-MEL-28 (right panel) by BrdU analysis at 48 hours post-treatment. EP: electroporation only; pGBI-2: pbi-shRNA™ STMN1 vector; pGBI-5: scrambled control vector. pGBI-2 significantly reduced DOC IC50 whereas pGBI-5 did not for both cell lines (One way ANOVA). Value represents mean of three separate studies with triplicate determinations.

Thus using a combined RNAi mechanism approach, as exemplified by the "bifunctional" shRNAs formulation described herein, an enhanced therapeutic RNAi effect to STMN1 knockdown compared to other RNAi's can be demonstrated. Similar activity over standard shRNAi to the same sequence involving a different target (PDX-1, a novel gene with oncogenic properties involved in pancreatic cancer) has also been shown to demonstrate marked advantage in knockdown of PDX-1 in correlation with tumor cell response in vitro and survival advantage in vivo (Liu, Rao et al. 2011) (BB-IND 14912).

pbi-shRNA™ STMN1 reduces IC50 of Docetaxel: Having demonstrated the effector mechanism and functional efficacy of the pbi-shRNA™ STMN1 vector, anticancer activity in vitro was further explored and an effective cell kill in several cancer cell lines (colon, breast, melanoma) was successfully shown. Both ribozyme and siRNA inhibition of stathmin mRNA produce additive to synergistic interactions with the taxanes (Mistry and Atweh 2006; Ngo, Peng et al. 2007; Wang, Dong et al. 2007). It was proceeded to examine the combined treatment outcome by pbi-shRNA™ STMN1 and anti-tubulin agent docetaxel (DOC) in both CCL-247 and SK-MEL-28 cells. The impact of pretreatment with pbi-shRNA™ STMN1 (0.5 ug/105 cells) was most profound at 24 h, where DOC IC50 was reduced from 3.4 nM to 0.6 nM in CCL-247 cultures. At 48 h (FIG. 12 Left Panel) and 72 h when a steady state of DOC-mediated anti-tumor effect was observed, pbi-shRNA™ STMN1 reduced DOC IC50 by approximately 3-fold (0.6+0.4 vs. 1.8+0.2 nM; p<0.08, n=3; One way ANOVA). At the DOC IC50 dose, co-treatment with pbi-shRNA™ STMN1 reduced cell growth by another 50%. Similar findings were observed with SK-MEL-28 which appeared to be more sensitive to the co-treatment. DOC IC50 was reduced from 2.25 nM to 0.16 nM at 48 h (FIG. 12 right panel).

pbi-shRNA™ STMN1 BIV Lipoplex Nanoparticle Delivery System: A successful gene-based systemic therapeutic approach requires a delivery platform that is without significant clinical adverse effects, effective in maintaining the functional integrity of its payload, and target selective/specific for both primary and metastatic tumor foci. The liposomal delivery system to be used in this proposal incorporates 1,2-dioleoyl-3-trimethyl-ammoniopropane (DOTAP) and cholesterol (Templeton, Lasic et al. 1997). This manually extruded formulation forms bilamellar invaginated vesicles (liposomal BIVs) which encapsulate nucleic acids to form BIV complexes. BIV complexes are flexible (Templeton, Lasic et al. 1997) and have been shown to penetrate numerous in vivo barriers allowing complete and homogenous penetration across the interstitial pressure gradient of large tumors and across the tight endothelial cell barrier in normal mice (Ramesh, Saeki et al. 2001), navigating across extremely tight posterior-blood retinal barrier in adult mouse eyes, and through several tight layers of smooth muscle cells in the arteries of pigs (Templeton, Alspaugh et al. 1999). Indeed, it is the flexibility of the 200 to 450 nm BIV complexes that allows them to penetrate across these barriers and are responsible for the highest levels of gene expression documented in all tissues and organs post-intravenous (IV) injections in mice. Furthermore, the increased half-life of 5 hours is, in part, contributed to the increased size above 100 nm making it harder for rapid RES-mediated clearance to occur. In addition, the liposomal BIV complexes are fusogenic, thereby bypassing endocytosis mediated DNA cell entry which could otherwise lead to nucleic acid degradation (Simberg D 2005) and TLR mediated off-target effects. More recently, in vitro imaging studies comparing pbi-shRNA™ STMN1 BIV transfection of PANC-1 cells were performed. The present inventors followed plasmid DNA fluorescence labeling procedures described by Akita et al (Godbey, Wu et al. 1999) using the commercially available Mirus Label IT technology. Plasmid DNA was covalently labeled either with CX-Rhodamine or Qdot705 (Godbey, Wu et al. 1999). The quantum dot, Qdot705-streptavidin, was attached to plasmid DNA covalently labeled with biotin using Label IT Biotin (Godbey, Wu et al. 1999). Plasmid DNAs were encapsulated in BIV-L prepared with TopFluor Cholesterol, Bodipy Cholesterol. Transfections were imaged on a wide-field, deconvolution fluorescence microscope in 96-well format for fixed cell imaging and in chamber slides for live cell imaging. Fixed cells were also DAPI stained. The data showed BIV complexes at the PANC-1 cell surface within 5 min post-transfection. The liposome stayed at the cell surface as expected for the fusogenic delivery system, and rhodamine labeled plasmid DNA was delivered to the nucleus within 30 min post-transfection. Images at 3 h post-transfection resembled those shown at 30 min (FIG. 27). This liposomal delivery system has been used successfully in a clinical trial (BB-IND 13744 and Hinderling, Karara et al. 2007). For instance patients with end stage lung cancer have been given multiple IV infusions of DOTAP/cholesterol 3p FUS1 gene therapy without clinically significant toxicity (Hinderling, Karara et al. 2007), and a unique DOTAP/cholesterol GNE gene has been delivered via intramuscular and intravenous infusion to a patient with hereditary inclusion body myopathy (HIBM2), a rare autosomal recessive neuromuscular disorder (Jay 2008; Phadke, Jay et al. 2009; Nemunaitis 2011).

Lipoplex Related "Off-Target" Effects: Although free plasmid DNA has shown limited potential for toxicity, DNA delivered as a lipoplex complex elicits dose-dependent toxicity and is expected to be more likely than the RNAi effector per se to contribute to therapy induced side effects at the doses used in this study (Nguyen, Atobe et al. 2007). Using the same bilamellar invaginated vesicle (cationic cholesterol:DOTAP) lipoplex (BIV-LP) that can be used, Roth and colleagues (BB-IND 10718) have treated 31 cancer patients with multiple IV injections of BIV-LP encapsulated TUSC2/FUS1 replacement gene expressing plasmid DNA at 6 dose levels, from 0.01 to 0.09 mg/kg (Lu 2007). Toxicity was limited to grade 2 fever among the 27 premedicated patients with 2 episodes of transient grade 3 hypophosphatemia resulting in a MTD of 0.06 mg/kg (Lu 2007). Transgene expression of delivered TUSC2/FUS1 lipoplex was demonstrated in tumor. A patient with hereditary inclusion body myopathy (HIBM) has also been treated at Mary Crowley Cancer Research Centers (MCCRC) with this BIV-LP encapsulating the GNE gene expressing plasmid DNA of identical backbone sequences as bi-shSTMN1 via multiple intramuscular (n=4) and intravenous (n=7) doses for 2 years through 7 mg (0.088 mg/kg) and with premedication has experienced only limited grades 1 and 2 toxicities (Nemunaitis G 2010). The cohort 1 lipoplex dose in the can be 0.01 mg/kg, approximately 11% of the maximum doses thus far used in the Roth and MCCRC studies showing these safety profiles.

Off-Target Effects: There are three potential types of off-target effects: 1) sequence-dependent/RISC mediated, 2) sequence-independent/RISC mediated, and 3) sequence-independent/innate immune mediated (Vaishnaw, Gollob et al.). To establish sequence dependent/RISC off-target biorelevance, using bioinformatics methodology, the potential off-targets for rats and for humans were predicted by BLAST homology search with STMN1 target site sequence against Ref. Seq. databases for rat and human, respectively. The Search results are shown in Appendix 1 (BLAST Search Results). The search was done using blast-n algorithm with focus on plus strand sequences with homology to the seed sequence region (position 2-8 of the guide strand, or position 12-18 of the plus strand as shown) (Jackson, Burchard et al. 2006). The rat database search resulted in more potential off-targets than human (21 found in addition to STMN1 for rat vs. 8 found for human) with at least two shared common potential off-targets.

To establish rat as bio-relevant model for on-target and off-target side effects, the bi-shRNA™ STMN1 LP activity in rat cancer cells was assessed, and the efficiency of rat STMN1 knockdown by bi-shSTMN1 was evaluated. In order to avoid ineffective transfection efficiencies that could be encountered with rat cancer cells, the rat STMN1 knockdown efficiency was first evaluated in CCL-247 cells by co-transfection of a rat STMN1 expression vector and bi-shRNA™ STMN1. A truncated version of rat STMN1 with 35 amino acids deletion at the N-terminus was constructed to differentiate the rat transgene from the endogenous human STMN1.

Figure 13:
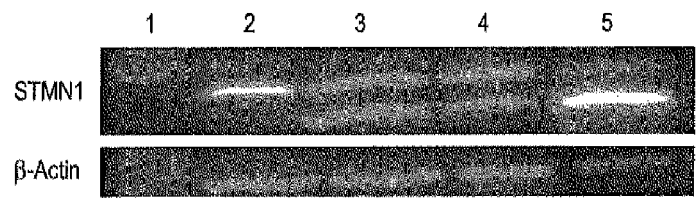
FIG. 13 shows expression of truncated version of rat STMN1 in CCL-247 cells. Rat STMN1 expression plasmid with 35 amino acids deletion at the N-terminus was tranfected into CCL-247 cells by electroporation. Western immunoblots were performed with equal amount of cell extract (30 ug total protein) at 72 hours post electroporation. Western immunoblots to detect STMN1 (upper band for endogenous human STMN1; lower band for truncated rat STMN1) and β-actin were done with mouse monoclonal antibodies for human STMN1 and human β-actin, respectively. Image capture and analysis was performed on the G-Box system (Syngene).

To determine the optimum concentration of plasmid DNA for electroporation, the truncated version of rat STMN1 was transfected into CCL-247 by electroporation. Expression of truncated rat STMN1 was detected by Western immunoblot at 72 hours post electroporation (FIG. 13, lower STMN1 band in lanes 3, 4 and 5). Both 25 ug and 50 ug (FIG. 13, lanes 3 and 4) samples effectively generated the truncated version of rat STMN1. 75 ug (FIG. 13, lane 5) generated robust amount of truncated rat STMN1, however the expression of other endogenous cell protein appeared to be affected by the transgene expression. Interestingly, the expression of the truncated rat STMN1 reduced endogenous human STMN1 expression.

Based on the data presented in FIG. 13, the present inventors established the transgene electroporation condition for the knockdown experiment in CCL-247 cells. A total of 50 ug of rat STMN expression plasmid and pbi-shRNA™ STMN1 plasmid DNA was used for each electroporation for which the expression of β-actin was not affected. Dose-dependent knockdown of rat STMN1 by pbi-shRNA™ STMN1 was effectively demonstrated with co-transfection of truncated rat STMN1 and pbi-shRNA™ STMN1 (FIG. 14, lanes 6, 7 and 8) in a dose responsive manner.

To demonstrate biorelevance of human pbi-shRNA™ STMN1 activity in rat models, 10 rat cancer cell lines were first screened for the STMN1 expression alongside human CCL-247 cells before knockdown experiments. All rat cell lines expressed significantly lower levels of STMN1 protein, relative to CCL-247 cells (Table 4). The tumor types that each cell line is derived from is listed below:

TABLE 4

Expression level of STMN1 in Rat cell lines, relative to CCL-247.

| Cell Line | Tissue Type | Relative STMN1 Protein Expression (Compared with CCL-247 after Normalized to β-Actin) |
|---|---|---|
| CCL-247 | Human Colorectal | 1.00 |
| AT3B-1 | Rat Prostate | 0.11 |
| MAT-Ly-Lu-B2 | Rat Prostate | 0.19 |
| RIN-M5F | Rat Insulinoma | 0.06 |
| MAT-B3 | Rat Adenocarcinoma | 0.11 |
| F98 | Rat Brain Glioma | 0.24 |
| RBA | Rat Mammary Adenocarcinoma | 0.12 |
| N1-S1 | Rat Liver Hepatoma | 0.23 |

TABLE 4-continued

Expression level of STMN1 in Rat cell lines, relative to CCL-247.

| Cell Line | Tissue Type | Relative STMN1 Protein Expression (Compared with CCL-247 after Normalized to β-Actin) |
|---|---|---|
| LA7 | Rat Mammary | 0.29 |
| FAT7 | Rat Nasal Squamous Carcinoma | 0.09 |
| XsSBR | Rat Small Intestine Adenocarcinoma | 0.09 |

Experiments to knockdown the STMN1 expression were performed by transfecting pbi-shRNA™ STMN1 into seven of the ten rat cancer cell lines. Three rat cancer cell lines that expressed a moderate level of STMN1 demonstrated significant STMN1 knockdown following pbi-shRNA™ STMN1 transfection (FIGS. 15 and 16; F98, RBA, and N1-S1 at 48%, 55% and 22%, respectively). The wide range of STMN1 knockdown is presumably due to varied transfection efficiency of each respective cell lines examined. However, in relation to percent knockdown relative to control CCL 247 percent knockdown, pbi-shRNA™ STMN1 was very effective on rat cells (F98—111%, RBA—128%, and N1-S1—51%), thereby further supporting relevance of the rat model to pbi-shRNA™ STMN1 (Table 5).

| Cells | Treatment | STMN Expression* Normalized to β-Actin | % STMN Knockdown Relative to Media | % STMN Knockdown Relative to CCL 247% |
|---|---|---|---|---|
| CCL 247 | Media | 2.48 | | |
| | pbi-shRNA ™ STMN1 | 1.41 | 43% | |
| F98 | Media | 0.60 | | |
| | pbi-shRNA ™ STMN1 | 0.31 | 48% | 111% |
| RBA | Media | 0.31 | | |
| | pbi-shRNA ™ STMN1 | 0.14 | 55% | 128% |
| N1-S1 | Media | 0.58 | | |
| | pbi-shRNA ™ STMN1 | 0.46 | 22% | 51% |

Table 5 showing Summary of the Semi-Quantitative Analysis of STMN1 knockdown.
*CCL247 STMN1 expression normalized to β-Actin was 2.48 to media and 1.41 to pbi-shRNA ™ STMN1.

Based on these data and establishing a biorelevant model, results from several studies assessing the safety and toxicity of pbi-shSTMN1 LP administration are submitted. Study RE-PTL-106 evaluated safety and toxicity of a single intravenous injection at one of three doses: 1.5, 15 and 150 ug (HED 0.0016 mg/kg, 0.016 mg/kg, and 0.16 mg/kg, respectively). Study RE-PTL-127 evaluated safety and toxicity of a single subcutaneous injection at a dose of 100 ug. Studies RE-PTL-133, RE-PTL-134, and RE-PTL-135 evaluated safety and toxicity of multiple intratumoral injections (six over a three week time period) at a high dose of 50 ug/animal and a low dose of 10 ug/animal.

For RE-PTL-106, a NOAEL (no observed adverse effect level) was documented at 1.5 and 15 ug (HED 0.0016 mg/kg and 0.016 mg/kg). Of 60 (30 male and 30 female) rats receiving 150 ug (HED 0.16 mg/kg), 10 (5 males/5 females) demonstrated lethargy and hunched posture on day of injection only (and hematuria in one female), five additional females demonstrated lethargy and squinted eyes on day of injection only and one female died but could not be necropsied due to rigor mortis without toxicity in the other animals. No signs of toxicity were demonstrated after 24 hrs.

For RE-PTL-127 a total of 270 Sprague Dawley rats were treated with SC delivery for toxicology assessment of pbi-shSTMN1 LP at 100 ug, empty liposomes and D5W (n=90). Overall the regimen was well tolerated and the only changes related to the injection site at gross pathology including thickening of the tissue and pale areas. These changes were thought to be related to the liposome rather than the pbi-shSTMN1 LP agent as they were also observed in the empty liposome group. An additional 210 Sprague Dawley rats were treated for biodistribution assessment (RE-PTL-125) and no clinically relevant toxic effect was observed to affect survival.

For RE-PTL-133, RE-PTL-134 and RE-PTL-135, no overt toxicity was observed after multiple intratumoral injections into colon cancer, breast adenocarcinoma and melanoma xenograft tumors.

With specific reference to sequence-dependent/RISC mediated off-target side effects, it is noted that since the time of protocol design a number of siRNA therapeutics have entered the clinic (Vaishnaw, Gollob et al.). Since the report, at least three more siRNA related therapeutic agents were approved for Phase I trial. The global RNA interference pipelines as shown summarized in Table 6 by Vaishnaw et al. below citing almost 1500 patients and healthy volunteers have been treated in RNAi programs globally including seven translational clinical therapeutic programs using systemic delivery, i.e., ALN-RSV (n=354) (Alnylam Pharmaceuticals, Inc.), QPI-1002 (n=56) (Quark Pharmaceuticals, Inc.), CALAA-01 (n=36) (Calando Pharmaceuticals), and ApoB SNALP. (n=23) (Tekmira Pharmaceuticals) (Vaishnaw, Gollob et al.) with safety data available on 1284 patients. In one of these studies, ALN-VSP02 (Alnylam), with two siRNAs targeting vascular endothelial growth factor (VEGF)-A and kinesis spindle protein (KSP), was administered IV every 2 weeks with 28 patients thus far treated at 0.1, 0.2, 0.4, 0.7, 1.0 and 1.25 mg/kg (Gollob J 2010). One patient at 0.7 mg/kg with extensive pancreatic neuroendocrine tumor with near complete replacement in both lobes of the liver died of hepatic failure following the second dose (possibly related) and a second patient at 1.25 mg/kg experienced grade 3 thrombocytopenia which resolved within 5 days (related). The MTD has not yet been reached and dose escalation continues. Encouragingly, a ≥40% decline in DCE-MRI Ktrans in 8 of 12 patients was recorded. Clinical responses (SD for ≥2 months) were seen at 0.4 (1 of 6), 0.7 (2 of 7) and 1.0 (2 of 3) mg/kg. Although siRNA intrinsically differs from plasmid DNA expressing bi-shSTMN1, the sequence-dependent off-target side effect(s) should be similar and, very possibly, less considering that in a recent comparison of siRNA versus shRNA seed region based off-target activity, a significantly narrower spectrum of gene expression changes were seen with the shRNA (Klinghoffer, Magnus et al.; Rao, Senzer et al. 2009). The fact that ALN-VSP02 with two siRNA sequences was observed to be well tolerated at even higher dose levels than will be used in this study is encouraging that sequence-dependent off target side effects of bi-shSTMN1 can be tolerated (Alnylam 2010). Furthermore, in a second study of multiple dose IV siRNA targeting ribonucleotide reductase (RRM2) in patients using a cyclodextrin-based polymer delivery system (Davis, Zuckerman et al. 2010), specific gene inhibition was demonstrated in three different dosing cohorts and no significant sequence dependent off target adverse events were observed.

TABLE 6

The Global RNAi Pipeline (Vaishnaw, Gollob et al.).
Table 2: The global RNA interference pipeline*

| Sponsor | Program (clinical stage) | Status | Target | Indication | Number enrolled |
|---|---|---|---|---|---|
| Alnylam/Cubist/Kyowa Kirin | ALN-RSV (phase IIb) | Ongoing | RSV nucleocapsid | Adult RSV infection | 354 |
| Pfizer/Quark | PF-04523655 (phase II) | Ongoing | RTP801 | (1)AMD, diabetic macular edema | 244† |
| Quark | QPI1002 (phase II) | Ongoing | p53 | (1)Acute kidney injury, delayed graft function | 56† |
| Zabecor | Excellair (phase II) | Ongoing | Syk kinase | Asthma | ? |
| Alnylam | ALN-VSP (phase I) | Ongoing | VEGF, KSP | Primary and secondary liver cancer | 55† |
| Calando | CALAA-01 (phase I) | Ongoing | RRM2 | Cancer | 36† |
| Silence | Atu-027 (phase I) | Ongoing | PKN3 | Cancer (GI, lung other) | 33† |
| Sylentis | SYL040012 (phase I) | Ongoing | β2 adrenergic receptor | Glaucoma | ? |
| Alnylam | ALN-TTR (phase I) | Ongoing | ITR | TTR amyloidosis | Enrollment begins H1, 2010 |
| Opko | Bevasiranib (phase III) | Terminated | VEGF-A | AMD | 522 |
| Allergan/SiRNA | AGN211745 (phase II) | Terminated | VEGFRI | AMD | 164 |
| Tekmira | ApoB SNALP (phase I) | Completed | ApoB | Hypercholesterolemia | 23 |
| Transderm | TD101 (phase I completed) | Completed | Mutant K6a | Pachyonychia congenita | 1 |
| Univ. Duisberg-Essen‡ | Bcr-abl (phase I completed) | Unknown | Bcr-abl oncogene | CML | 1 |

AMD = age-related macular degeneration; CML = chronic myeloid leukemia; GI = gastrointestinal; KSP = kinesin spindle protein; PKN = protein kinase N3; RRM2 = ribonucleotide reductase M2; RSV = respiratory syncytial virus; RTP =; TTR = transthyretin; VEGF = vascular endothelial growth factor; VEGFRI = vascular endothelial growth factor receptor I.

*All data from corporate websites, press releases and http://www.clinicaltrials.gov †Enrollment ongoing ‡From Koldehoff et al., 2007

Insofar as bi-shSTMN1 follows the miRNA biogenic pathway, attention is appropriately directed to sequence-independent/RISC mediated AE. As recently noted and reconfirmed, shRNA off-target effects are less related to sequence- or target-specificity than to shRNA doses (Grimm, Streetz et al. 2006). Exportin-5 (Xpo-5) and Ago-2 saturation may result in non-Slicer RISC entry potentially increasing "off-target side effects." Whether through saturation of Xpo-5 or RISC complex loading, the use of shRNA with pol II promoters (as is the case with bi-shSTMN1) allows for safe therapeutic delivery in vivo (Giering, Grimm et al. 2008; Grimm, Wang et al. 2010). In addition, given the enhanced potency of bi-shSTMN1 versus siSTMN1 (5-log difference in IC50), a lower required effective dose is likely to broaden the therapeutic window.

Addressing sequence-independent/innate immune mediated side effects, as previously mentioned, the fusogenic BIV-LP carrier will bypass endosomal/lysosomal compartments thereby eliminating plasmid unmethylated CpG mediated TLR 9 activation. Although TANK-binding kinase-1 (TBK-1) remains a potential pathway for DNA initiated innate immune signaling activation (Ishii et al, 2008), this has not translated into clinically evident AE with BIV-LP encapsulated TUSC2/FUS1 or GNE.

In vivo animal summary: A total of seven efficacy studies were performed. Study RE-PTL-105, was performed to determine the effect of a single intratumoral (IT) injection of the bifunctional shRNA-STMN1 (pbi-shRNA™ STMN1) BIV (bilamellar invaginated vesicle) lipoplex (LP) at 10 ug, 40 ug or 100 ug doses in vivo using a mouse model of CCL-247 tumor xenograft. Next, multiple injections (n=6) at 2 doses (50 ug and 100 ug) were explored in 3 studies (RE-PTL-107, RE-PTL-120 and RE-PTL-109) with CCL-247 cells and primary tumor grafts of human melanoma and osteosarcoma, using the same delivery vehicle (DOTAP: Cholesterol). Dosages tested were consistent with others for assessing in vivo tumor growth inhibitory activity (Ramesh, Saeki et al. 2001; Ito, Ji et al. 2004). To determine dose-dependent anti-tumor activity of the pbi-shRNA™ STMN1 LP, RE-PTL-115 utilized 5 doses: 0.01 ug, 0.1 ug, 1.0 ug, 10 ug, and 50 ug. Further, animal study RE-PTL-114 was performed to demonstrate target gene knockdown in vivo using mouse model of CCL-247 tumor xenograft using pbi-shRNA™ STMN1 LP at doses of 1 or 10 ug.

Survival was investigated using three xenograft models, human colorectal carcinoma cell line HCT-116 (also known as CCL-247), human breast adenocarcinoma cell line MDA-MB-231, and human melanoma cell line A2058, to evaluate the longer term safety any adverse effects of pbi-shRNA™ STMN1 LP and pGBI5-LP (scramble control) in female Harlan rnu/rnu nude rats at high and low dose intratumoral administration of six doses over three weeks (Charles River Discovery Services, Piedmont Research Center) in studies RE-PTL-133, RE-PTL-134 and RE-PTL-135, respectively.

A temporal biodistribution profile of pbi-shRNA STMN1 was established in RE-PTL-125 to assess immune function in a biorelevant rat model (Sprague Dawley) over three months after a single subcutaneous injection (Charles River Laboratories, Preclinical Services, Ohio (PCS-OH)).

Two toxicity studies were also conducted. Study RE-PTL-106 examined the toxicity profile of the pbi-shRNA™ STMN1 LP when administered to immune-competent rats at 3 doses (1.5, 15 and 150 ug) equivalent to doses of 0.4, 4 and 40 ug doses respectively in immune-competent mice. Study RE-PTL-127 examined potential toxicity of pbi-shRNA™ STMN1 LP after a single subcutaneous injection in a biorelevant rat model (Sprague Dawley) (Charles River Laboratories, Preclinical Services, Ohio (PCS-OH)).

Efficacy studies: To evaluate the efficacy of pbi-shRNA™ STMN1 LP in vivo, studies were performed using 3 mouse tumor xenograft models.

The first model used colorectal cancer cell line, CCL-247 cells to mirror in vitro determinations for induction of tumor xenografts in immune-compromised (athymic nude) mice. Eight (8) to 10×106 CCL-247 cells were injected subcutaneously in the dorsal flank of athymic nude mice under anesthesia to establish tumor xenografts. IT treatment was initiated when the average tumor volume for each group of mice was approximately 100 mm3. Tumors sizes were measured using vernier calipers and measuring the two perpendicular diameters of the tumor. Mean tumor diameter was calculated using the formula $\sqrt{(D1 \times D2)}$ where D1 and D2 are the two perpendicular diameters. Tumor volumes were calculated with the formula: $(L \times W2) \times 0.5$, where L is length and W is width of the tumor. This mouse model was used for studies RE-PTL-105, RE-PTL-107, RE-PTL-114 and RE-PTL-115.

Additionally, mouse tumor model xenografts were established by grafting fresh human cancers from tumor biopsy specimens of patients diagnosed with cancer into immune-compromised mice. These tumors are referred to as "tumor-grafts" to differentiate them from "tumor xenografts" established using tumor cell lines grown in vitro. These tumor models were established in the Human Tumor Xenograft Bank (HTXB) at Van Andel Research Institute (VARI). Treatment for the tumorgrafts was initiated when they reached a size of approximately 260 mm3 (osteosarcoma model) or approximately 160 mm3 (melanoma model). Tumor sizes were measured using vernier calipers and tumor volume was calculated using an equation for an oblate spheroid: (½× length×width×depth). This mouse model was used for study RE-PTL-109 (osteosarcoma model) and RE-PTL-120 (melanoma model).

Animal studies were performed after obtaining IACUC approval of the respective institutions (RE-PTL-105, Baylor Sammons Cancer Center, Dallas, Tex.; RE-PTL-107, RE-PTL-114, RE-PTL-115, RE-PTL-106, University of North Texas, Health Science Center, Fort Worth, Tex.; RE-PTL-109, and RE-PTL-120 Van Andel Research Institute, Grand Rapids, Mich.).

All post-treatment tumor measurements were normalized to pre-treatment values for individual tumors to enhance intergroup comparative analyses. Percent (%) tumor growth reduction was determined by comparing mean tumor values of the treated group with those of the mock (D5W)-treated cohort by two tailed student t-test analyses or by One-way or repeated Measures ANOVA.

Study 1 (RE-PTL-105): In the study RE-PTL-105, fifty mice bearing CCL-247 tumor xenografts were injected (5 mice per cohort) once with the pbi-shRNA™ STMN1 LP at one of 3 doses (10 ug, 40 ug and 100 ug) or with a control which included a scrambled shRNA/lipoplex (LP), empty liposomes or diluent (D5W) only. Additionally, tumor xenografts for 2 cohorts (5 mice each) were treated 5 times (multiple injection) IT with 40 ug of pbi-shRNA™ STMN1 LP or scrambled LP on consecutive days. Gross pathology was performed on the day of sacrifice (Day 16). All mice were monitored and tumor measured for 2 weeks after treatment. Gross pathology was performed on the day of sacrifice (Day 16). All post-treatment tumor measurements were normalized to pre-treatment values for individual tumors to enhance intergroup comparative analyses. Percent (%) tumor growth reduction was determined by comparing mean tumor values of the treated group with those of the mock (D5W)-treated cohort by two tailed student t-test analyses.

Results: Initial in vivo efficacy assessments were performed following a single intratumoral injection of the lipoplexed pbi-shRNA™ STMN1 on previously established CCL-247 xenografts (FIG. 17). It was observed significant reductions of CCL-247 xenograft growth of 44% at days 7 and 55% at day 8 after a single injection (p<0.05, n=5) at 10 ug of pbi-shRNA™ STMN1 LP compared with untreated tumors. Control expression plasmid lipoplex (scrambled LP) did not alter xenograft growth significantly (FIG. 17). Thus a single intratumoral treatment of 10 ug of pbi-shRNA™ STMN1 LP was effective to achieve tumor-inhibition reduction for >7 days. Treatment with either 40 ug (single or multiple) or 100 ug pbi-shRNA™ STMN1 LP did not result in statistically significant growth reduction.

Histopathology: Hematoxylin and eosin (H&E) staining was performed on FFPE tumor tissues from all the mice (Propath Labs, Dallas). Microscopic examination demonstrated extensive central necrosis in 49/50 tumor samples. Tumor cells were large and had hyperchromatic nuclei with numerous mitoses. Tumor cells were arranged in an epithelial pattern but did not show definitive differentiation. There were no tumor cells identified on one slide derived from a mouse tumor xenograft treated 5 times with 40 ug scrambled control lipoplex. The slide primarily consisted of "necrotic debris with a small amount of fibrous tissue".

Study 2 (RE-PTL-107): In the study RE-PTL-107, forty eight mice bearing CCL-247 tumor xenografts (8 mice per cohort) were injected with either pbi-shRNA™ STMN1 LP at 1 of 2 doses (50 ug and 100 ug), the scrambled LP at 1 of 2 doses (50 ug and 100 ug) or empty liposomes or diluent (D5W) only. Injections were performed once a day for 6 consecutive days for all groups. All mice were monitored and tumors measured until the tumor size in the diluent treated group was ≥2 cm3. Additional eight mice were injected only once intratumorally with 50 ug of GFP-lipoplex (n=8) or with diluent D5W (n=4). In order to determine transfection efficiency, these 2 groups of mice were sacrificed 48 hours after the single IT injection. Tumor and major internal organs were collected. Half of the tissue was snap frozen in crushed dry ice and the other half was fixed in 10% buffered formalin for further molecular analysis. Preliminary studies examining biodistribution of plasmid DNA was performed using the frozen tissues.

Results: Six consecutive IT injections of all agents were well tolerated. No treatment related deaths were observed. No treatment related body weight loss was observed in mice.

At 14 days after the last injection (Day 20), treatment with pbi-shRNA™ STMN1 LP reduced the growth of CCL-247 tumor xenografts by 29-33% (Table 7) as compared to D5W treated animals. However, there did not appear to be a dose dependent effect between 50 and 100 ug of pbi-shRNA™ STMN1 LP. Growth inhibition was also observed in mice treated with scrambled LP (Table 7). All treatments showed a loss of long-term activity after Day 20 (FIG. 18).

TABLE 7

(RE-PTL-107) CCL-247 tumor xenograft growth reduction after treatments compared to D5W control.

| Treatment | Tumor Size (mm³) | | CCL-247 tumor reduction |
| --- | --- | --- | --- |
| | Before treatment | Post-treatment (day 20) | compared to D5W treated group on day 20 |
| pbi-shRNA ™ STMN1 LP (50 ug) | 95 ± 21 | 518 ± 260 | 29% |
| pbi-shRNA ™ STMN1 LP (100 ug) | 96 ± 17 | 490 ± 168 | 33% |
| Scrambled control (50 ug) | 95 ± 22 | 359 ± 182 | 51% |
| Scrambled control (100 ug) | 96 ± 17 | 415 ± 190 | 43% |
| empty liposome | 94 ± 25 | 795 ± 244 | −9.20% |
| D5W | 94 ± 23 | 728 ± 321 | reference |

None of the CCL-247 tumor xenograft sizes of mice treated with of pbi-shRNA™ STMN1 LP were significantly different from those treated with either scrambled LP, empty liposomes or D5W diluent control by repeated measures ANOVA (FIG. 18).

Histopathology: H&E staining was performed on formalin fixed paraffin embedded (FFPE) tumor tissues from all the mice (Antech Diagnostics, Irvine, Calif.). Microscopic analysis of FFPE samples did not demonstrate treatment related lesions in the internal organs examined (liver, kidneys, heart, quadriceps muscle and brain). All spleens, irrespective of amount or type of treatment, demonstrated mild lymphocytic hyperplasia. All the tumors demonstrated varying degree of necrosis that ranged from ~20% to ~80%, with no remarkable differences across treatment groups. Perilesional lymphocytic infiltrate was also observed in a few tumors. Tumor metastasis was seen in lungs of 5 mice from all treatment groups (1 mouse treated with pbi-shRNA™ STMN1 LP (100 ug), 1 mouse treated with scrambled LP (50 ug), 1 mouse treated with empty liposomes and 2 mice in D5W treated group). There was a certain degree of bronchiolitis and inflammation observed in lungs from mice across all treated groups.

Immunohistochemical detection of GFP expression: H&E staining of FFPE tumor tissues showed no tumor sections in 2/8 tumors treated with GFP-lipoplex. Moreover, examination of the tissue sections under the microscope showed tissue sections that were folded.

IHC staining for GFP expression was performed on 4 of the 8 tumors treated with GFP-lipoplex and 2 of the untreated tumors. All the tumors sections demonstrated diffuse, non-specific staining with the anti-GFP antibody at a dilution of 1:500. Analysis of transfection efficiency by GFP protein expression yielded inconclusive results as a result of poor quality of tumor tissue sections and background staining observed using untreated tumors sections and with isotype control antibody.

Use of low passage tumorgrafts: Primary and early passaged xenografts tend to recapitulate phenotypic features of the originating patient's tumor, and likely constitute more appropriate in vivo models for assessing preclinical efficacy of experimental treatment approaches (Perego, Tortoreto et al.).

The treatment outcome by pbi-shRNA™ STMN1 LP was examined in low passage primary xenografts of human melanoma and osteosarcoma. At the VARI Human Tumor Xenograft Bank, tumor models were established by engrafting surgically excised, pathologically defined tumor biopsies into immune-compromised nude mice, referred to as "tumorgrafts" to differentiate them from tumor xenografts of pre-established tumor lines maintained in vitro. These tumorgrafts were subsequently cryopreserved and profiled molecularly by Human Genome U133 Plus 2.0 Array (Affymetrix) and analyzed by Xenobase-BioIntegration Solutions (XB-BIS), a bioinformatics package developed at VARI to manage and analyze data across molecular, cellular, preclinical, and clinical platforms (www.xbtransmed.com). STMN1 expression in human tumors at HTXB was quantified according to hybridization signal intensities with both STMN1 probes on the U133 Plus 2.0 Array.

Treatment for the tumorgrafts was initiated when they reached a size of approximately 260 mm3 (osteosarcoma model) or approximately 160 mm$^3$ (melanoma model). Study mice (athymic nude mice) were transplanted with osteosarcoma tumorgrafts (PTSH-0005) or melanoma tumorgrafts (PTSH-0021) from a founder mouse at VARI according to the institution's procedures (i.e. approximately 10-30 mm3 sized tumorgraft pieces were transplanted into study mice). After tumorgraft transplantation, the recipient study mice were randomly assigned to various groups in the study. In order to account for the differences in the time taken by each tumorgraft to reach the size for treatment initiation mice were enrolled in the study on a continuous basis to receive the various treatments.

Study 3 (RE-PTL-120): pbi-shRNA™ STMN1 LP (10 ug) significantly reduced tumor growth from day 20 (41%, p≤0.05, n=7) to Day 34 (53%, p<0.05) after first injection. An increased dose of 50 ug attained stronger growth inhibition (70% reduction as compared with mock-treated tumors, p≤0.05 on Day 26; n=8) that was extended to Day 46 (FIG. 19). By comparison, similar treatments at 1 ug produced measurable tumor size reductions that did not differ significantly from mock-treated tumors (33% at Day 34 after first injection), nor did treatments by "empty liposome" without an expression plasmid load (23% at Day 34 after first injection). Tumor weight determinations confirmed that only treatment with 50 ug pbi-shRNA™ STMN1 LP significantly reduced tumor mass (0.46±0.07 g, p=0.02) as compared to D5W controls (0.85±0.11 g) on the day of necropsy (Day 46 after the first injection). Significantly reduced tumor mass was not observed after treatments with 1 or 10 ug pbi-shRNA™ STMN1 LP (0.56±0.13 g and 0.55±0.06 g respectively).

Results: Treatment with 10 ug significantly reduced tumor growth from Day 20 (41%, p≤0.05, n=7) to Day 34 (53%, p<0.05), whereas similar treatments at 1 ug did not differ significantly from mock-treated tumors (33% at Day 34), nor did treatments by "empty liposome" without an expression plasmid load (23% at Day 34) (FIG. 19). Melanoma tumor growth was markedly inhibited over the course of treatment with 50 ug pbi-sh STMN1 LP. Interestingly during the treatment, the cancer tumor size actually demonstrated stable size to evidence of progressive decrease in size. However, once dosing was discontinued the tumor growth appeared to recover at a much slower rate than controls and lasted longer than 20 days. On Day 26 (Day 46) after the last injection, there was 70% reduction as compared with mock-treated tumors (p<0.05; n=8 per group).

Study 4 (RE-PTL-109): Study RE-PTL-109 was performed using six IT injections of 2 doses of pbi-shRNA™ STMN1 LP using tumorgrafts that were established from a primary human osteosarcoma tumor as opposed to in vitro cultured cell lines such as CCL-247 cells. This is the one of two collaborative studies performed in conjunction with the Human Tumor Xenograft Bank (HTXB) at Van Andel Research Institute (VARI). Such heterotransplanted tumors have been demonstrated to be clinically relevant since they resemble the originating tumor in terms of pathology, tumor marker expression, interaction of tumor and stromal cells and signal transduction pathways (Fu, Herrera et al. 1992; Lopez-Barcons 2009; Revheim, Seierstad et al. 2009). The osteosarcoma tumorgraft model chosen for the efficacy study had intermediate levels of stathmin 1 (STMN1) expression when compared to the STMN1 expression of multiple tumorgraft models profiled at VARI.

Thirty-two (32) mice received either pbi-shRNA™ STMN1 LP at 1 of 2 doses (50 ug and 100 ug) or scrambled LP at 1 of 2 doses (50 ug and 100 ug) (8 mice per group). Seven mice were injected with D5W (diluent) and 5 mice received empty liposomes. Injections were administered once a day for 6 consecutive days. An additional eight mice with osteosarcoma tumorgrafts were injected only once intratumorally with 50 ug of GFP-lipoplex and 5 mice received diluent (D5W). In order to determine transfection efficiency, these 2 groups of mice were sacrificed at 48 hours after the single IT injection. All mice were monitored and tumors were measured using digital vernier calipers until the tumors reached the maximum size allowed by IACUC (≥2 cm3). At necropsy, tumor and internal organs (liver, lungs, spleen, kidneys, heart, brain, diaphragm, and quadriceps muscle adjacent to the IT injection site) were collected. A major part of each tissue was snap frozen in dry ice and a small tissue piece immersed in 10% buffered formalin. Preliminary studies examining biodistribution of plasmid DNA was performed using the frozen tissues.

The time point at which mice were sacrificed varied and was according to one of the following criteria: 1) when the tumor size remained less than or equal to the pre-treatment tumor value for over 2 weeks, 2) when the tumor reached the maximum allowable tumor size approximately 2 cm3, in the absence of any other signs of distress (i.e. tumor necrosis, 20% weight loss in one week, abnormal behavior), according to IACUC regulations at VARI, MI, and 3) at 2 weeks after receiving the last injection due to misinterpretation of protocol. As a result, there were not sufficient mice available after day 16 to perform statistical analysis.

Results: IT injection of all agents was well tolerated. No treatment related deaths were observed. No treatment related body weight loss was observed in mice after treatment.

Prolonged survival in mice was significant at the 50 ug (mean 54 days) and 100 ug doses (mean 46 days) of the pbi-shRNA™ STMN1 LP compared to D5W (mean 19 days) at a p value of 0.009, and 0.027 respectively. However, consistent with known pharmacotoxicity of lipoplex particles (Omidi, Hollins et al. 2003; Akhtar and Benter 2007), scrambled LP at doses of 50 ug (mean 33 days) and 100 ug (mean 43 days) survival also achieved statistical significance in survival over D5W.

Six (6) intratumoral injections of 50 ug and 100 ug of pbi-shRNA™ STMN1 LP essentially abrogated low passage osteosarcoma tumorgrafts which were significantly reduced (p<0.05, n=8) as compared to diluent treated tumorgrafts until Day 22 (50 ug) or Day 20 (100 ug) (FIG. 20). The last evaluable statistical time-point was Day 22 after the first injection in accordance to the maximum tumor size of the control cohort before termination of study, as outlined in study protocol.

Osteosarcoma tumor reductions translated into significantly extended survival for both 50 ug-treated (mean survival of 54 days; p=0.009) and 100 ug-treated cohorts (mean survival of 46 days; p=0.027).

Histopathology of Osteosarcoma tumor graft tissues: Histopathological analysis on tumor tissues from all treatment groups demonstrated multiple tumor nodules with chondroid differentiation. There were many cells with atypical nuclei and scattered mitotic figures. Overall, residual tumorgrafts after pbi-shRNA™ STMN1 LP-treatment (in either 50 or 100 ug cohorts) displayed reduced viability (mean value of 50%)

as compared to tumorgrafts treated with the scrambled control (mean viability of 75%) and untreated tumors (mean viability of ~95%).

Histopathology of Organ Tissue: There were no distinguishing, treatment-related histopathological indications in any of the major mouse organ tissues examined. The most common change that was seen was atelectasis of the lungs, which varied in severity. However, this is a very common finding in lungs that were not perfused. Extramedullary hematopoiesis in liver, hydronephrosis in one animal, accumulations of lymphocytes and some hemorrhage that was noted, were all incidental findings according to the pathologist at IDEXX. No change was seen that would indicate any consistent treatment-associated effect. Metastasis of tumor to distant organs was not observed.

Immunohistochemical detection of GFP expression: Analysis of transfection efficiency by GFP protein expression yielded inconclusive results as a result of background staining observed using untreated tumors sections and with isotype control antibody.

Study 5 (RE-PTL-115): Study (RE-PTL-115) assessed the efficacy of pbi-shRNA™ STMN1 LP when administered intratumorally in a mouse model of CCL-247 tumor xenograft, at 5 different doses. To determine feasibility of optimizing anti-tumor efficacy through repeat injections, CCL-247-xenografted mice (n=48) were treated with 3 daily doses of pbi-shRNA™ STMN1 LP after tumors reached a size of approximately 100 mm3. These mice received either the pbi-shRNA™ STMN1 LP at 1 of 5 doses (0.01 ug, 0.1 ug, 1 ug, 10 ug, and 50 ug) or diluent D5W (water+5% dextrose) only. After the last IT injection, mice were sacrificed when the tumor volume was ≥2 cm3, or at the first signs of distress. Tumor and major internal organs were collected for further analysis.

Results: Multiple IT injection of all agents was well tolerated. No treatment related deaths were observed.

To determine feasibility of optimizing anti-tumor efficacy through repeat injections, CCL-247-xenografted mice were treated with 3 daily doses of pbi-shRNA™ STMN1 LP after tumors reached a size of >100 mm3. Dose dependent growth reductions were observed within the dose range of 0.01-10 ug (0% to 57% reductions at day 15 compared with mock-treatment; linear regression analysis, R2=0.86, linear regression analysis; FIG. 21a). However, only 10 ug and the 50 ug treatments consistently attained significant growth reductions (57% and 48% reduction at day 15, respectively; p<0.05, n=8).

Compared with the earlier study where animals received only a single injection of the same dose, significant growth reductions were extended to 26 days after first injection in the 10 ug treatment arm (40% reduction, p<0.05, n=8), indicating that repeat treatment prolonged antitumor activity (FIG. 21b) as compared with animals that received a single intratumoral injection (RE-PTL-105, RE-PTL-107 and RE-PTL-115). Enhanced growth reduction was confirmed by tumor weight measurements on day 26 after the first injection, with significantly reduced tumor weight in animals treated with 50 ug (0.65±0.17 g, p=0.03) and 10 ug (0.67±0.13, p=0.04) of pbi-shRNA™ STMN1 LP as compared to D5W controls (1.00±0.07 g). Since repeated treatments with 50 ug did not achieve proportionately higher tumor reduction, the benefit of repeat injections likely stem from introduction of pbi-shRNA™ STMN1 to previously untransfected tumor cells.

Study 6 (RE-PTL-114): Study RE-PTL-114 examined target gene knockdown by pbi-shRNA™ STMN1 LP when administered intratumorally in a mouse model of CCL-247 tumor xenograft. In this study, seventy-five (75) mice received a single injection each day for 6 consecutive days. Sixty (60) mice received either the pbi-shRNA™ STMN1 LP or the scrambled LP at 1 of 2 doses (1 ug and 10 ug). Fifteen (15) mice were injected with diluent D5W (water+5% dextrose) only. After the last IT injection, mice were sacrificed at 24, 48 or 72 hours (i.e. 5 mice per time point per group). Tumor and major internal organs were collected for molecular analysis.

Results: Western blot analysis using CCL-247 tumor xenografts demonstrated STMN1 protein knockdown only in mice treated with 10 ug pbi-shRNA™ STMN1 LP and not in CCL-247 tumor xenografts treated with scrambled LP or diluent (D5W) (FIG. 22).

To confirm the in vivo molecular impact of pbi-shRNA™ STMN1 LP treatment, TMN1 expression was examined in harvested control and treated CCL-247 xenografts by immunoblot analysis. Assessments of CCL-247 tumor xenografts that were excised at 24 hours post-injection with 10 ug of pbi-shRNA™ STMN1 LP demonstrated significantly reduced STMN1 (44% median reduction at 24 hour; 3/3 tumors tested), based on densitometric values normalized to β-actin expression and compared with untreated CCL-247 cells (Exemplified in FIG. 22). In contrast, STMN1 expression was not reduced in D5W-treated cohorts at the same time points. Mean STMN1 reduction in scrambled LP-treated tumors were 0% in 24 hour harvested cohorts.

Survival assessments: Xenograft model assessments were also conducted to rule out long term adverse effect of survival with pbi-shRNA™ STMN1 LP using three cell lines for human colorectal carcinoma, human breast adenocarcinoma and human melanoma in nude rats (Charles River Discovery Services, Piedmont Research Center). The xenograft tumors were established by injecting tumor cells into the right flank of each test animal. Each study contained six test groups of 20 animals that received 114 ul/animal of one of the following, pbi-shRNA™ STMN1-LP at either 0.44 or 0.088 mg/ml, pGBI5-LP at either 0.44 or 0.088 mg/ml, 5% dextrose in de-ionized water (D5W) or empty liposomes at 10 mg/ml. IT injections were given on Days 1, 5, 9, 13, 17, and 21 for all groups in all studies except the third study, RE-PTL-135, which terminated before the final dose day, Day 21.

Studies RE-PTL-133, RE-PTL-134 and RE-PTL-135, were carried out until Day 43, Day 36 and Day 20, respectively. The study endpoints differ based on the growth rate of the tumor model used and the burden growing tumors placed on the test animals. These cell lines were relatively fast growing and the study duration was determined based on the growth rate.

Tumors were measured twice-weekly using calipers. Animals were euthanized at the end of study or when their tumors reached a specified endpoint volume, whichever was achieved first. The time-to-endpoing (TTE) was calculated for each rat. Animals that did not reach the endpoint time were assigned a TTE value equal to the last day of the study. Treatment outcome was determined by tumor growth delay (TGD), defined as the increase in the median time to endpoint (TTE) in a treatment group compared to the D5W control group. Regression response was also considered as a part of treatment efficacy during the study. Complete regression, where the tumor volume was less than 13.5 mm$^3$ for three consecutive measurements, was classified as a tumor-free survivor (TFS).

The two-tailed logrank test was used to determine the statistical significance of the difference between the overall survival of a treatment group versus the D5W control group.

Study 1 (RE-PTL-133): Human colorectal carcinoma cell line HCT-116 (also known as CCL-247) was used to evaluate the safety effect of pbi-shRNA™ STMN1 LP and pGBI5-LP (scramble control) in female Harlan rnu/rnu nude rats (Charles River Discovery Services, Piedmont Research Center) in Study RE-PTL-133. Xenograft tumors were initiated by injecting 5×106 HCT-116 tumor cells into the right flank of the test rats. The study included six test groups (n=20) that received 114 ul/animal of one of the following, pbi-shRNA™ STMN1-LP at either 0.44 or 0.088 mg/ml, pGBI5-LP at either 0.44 or 0.088 mg/ml, 5% dextrose in de-ionized water (D5W) or empty liposomes at 10 mg/ml. IT injections were administered for all groups on Days 1, 5, 9, 13, 17, and 21. Animals were euthanized at the end of study (Day 43) or when their tumors reached the specified endpoint volume of 5,000 mm3. Treatment outcome was determined by tumor growth delay (TGD), defined as the increase in the median time to endpoint (TTE) in a treatment group compared to the D5W control group. Regression response was also considered as a part of treatment efficacy during the study. Complete regression, where the tumor volume was less than 13.5 mm3 for three consecutive measurements, was classified as a tumor-free survivor (TFS).

The two-tailed logrank test was used to determine the statistical significance of the difference between the overall survival of a treatment group versus the D5W control group.

Results: There was one survivor in the D5W control group, which was classified as a complete regression/tumor free survivor (CR/TFS). The median TTE was 13.8 days, establishing a maximum possible TGD of 29.2 days (212%). The median TTE was earlier than the study endpoint (Day 43) because the tumors grew very quickly, requiring the test animal to be sacrificed before receiving all of the intended doses.

Significant (P<0.01) tumor growth delay was observed for Group 2 after six IT injections of pbi-shRNA™ STMN1 LP at 0.44 mg/ml (50 ug/animal). The treatment yielded a median TTE of 18.5 days (34% TGD). Out of this treatment group there were six study survivors, of which three were partial regressions and one TFS.

None of the other treatment groups yielded significant results against the D5W control group (Table 8).

Overall, there were tumor free survivors in Group 1 (n=1), Group 2 (n=1) Group 5 (n=1) and Group 6 (n=1). There were partial regressions in Group 2 (n=3), Group 4 (n=2) and Group 5 (n=1).

TABLE 8

Treatment outcomes for TGD in HCT-116 xenograft tumors.

| Treatments | Group | TTE Range | TGD | Significance vs Control |
|---|---|---|---|---|
| Empty Liposome | 1 | 15-43 days | 13% | NS |
| pbi-shRNA ™ STMN1-LP 0.44 mg/ml | 2 | 11-43 days | 34% | P < 0.01 |
| pbi-shRNA ™ STMN1-LP 0.088 mg/ml | 3 | 11-25 days | -6% | NS |
| pGBI5-LP 0.44 mg/ml | 4 | 11-43 days | 9% | NS |
| pGBI5-LP 0.088 mg/ml | 5 | 11-43 days | 11% | NS |
| D5W Control | 6 | 11-43 days | n/a | n/a |

TTE = Time to endpoint; TGD = Tumor growth delay; n/a = not applicable; NS = Not significant.

The pbi-shRNA™ STMN1-LP treatments yielded significant TGD at 0.44 mg/ml dose against the D5W control treatment and there was no adverse survival limitations.

Histopathology: There was no significant difference in tumor histomorphology across the six experimental groups. Variable degrees of necrosis, inflammation, fibrosis, and mineralization were common in tumors from all the groups.

Study 2: RE-PTL-134. Human breast adenocarcinoma cell line MDA-MB-231 was used to evaluate the safety effect of pbi-shRNA™ STMN1-LP and pGBI5-LP in female Harlan rnu/rnu nude rats (Charles River Discovery Services, Piedmont Research Center) in Study RE-PTL-134. Xenograft tumors were initiated by injecting 1×107 MDA-MB-231 tumor cells into the right flank of the test rats. The study included six test groups (n=20) that received 114 ul/animal of one of the following, pbi-shRNA™ STMN1-LP at either 0.44 or 0.088 mg/ml, pGBI5-LP at either 0.44 or 0.088 mg/ml, 5% dextrose in de-ionized water (D5W) or empty liposome at 10 mg/ml. IT injections were administered for all groups on Days 1, 5, 9, 13, 17, and 21. Animals were euthanized at the end of study (Day 36) or when their tumors reached the specified endpoint volume of 8,000 mm3. Treatment outcome was determined by tumor growth delay (TGD), defined as the increase in the median time to endpoint (TTE) in a treatment group compared to the D5W control group. Regression response was also considered as a part of treatment efficacy during the study. Complete regression, where the tumor volume was less than 13.5 $mm^3$ for three consecutive measurements, was classified as a tumor-free survivor (TFS).

The two-tailed logrank test was used to determine the statistical significance of the difference between the overall survival of a treatment group versus the D5W control group.

Results: There were four survivors in the D5W control group, two of which exhibited self-limiting growth. The median TTE was 21.0 days, establishing a maximum possible TGD of 15.0 days (71%).

None of the treatment groups showed significance compared to the control D5W group (Table 9). There was one TFS in Group 3: pbi-shRNA™ STMN1-LP at 0.088 mg/ml. There was also a treatment related (TR) death in Group 4: pGBI5-LP 0.44 mg/ml. Treatment related deaths are classified as attributable to treatment side effects as evidenced by clinical signs and/or necropsy, or due to unknown causes during the dosing period or within 14 days of the last dose. Animals classified as TR deaths were assigned a TTE value equivalent to the day of death. However, for this treatment related death, no body weight loss or clinical signs of drug toxicity were observed. The TTE Range, shown in Table 9, is higher than the Median TTE for 5 of the 6 groups. This is due to the TTE calculation performed by Charles River when conducting the experiment. When animals were sacrificed before the end of the study the TIE was recorded as the last day in the study. This lowers the median value outside of the range of observed TTEs.

TABLE 9

Treatment outcomes for TGD in MDA-MB-231 xenograft tumors.

| Treatments | Group | TTE Range | TGD | Significance vs Control |
|---|---|---|---|---|
| Empty Liposome | 1 | 22-36 days | 4% | NS |
| pbi-shRNA ™ STMN1-LP 0.44 mg/ml | 2 | 22-36 days | -2% | NS |
| pbi-shRNA ™ STMN1-LP 0.088 mg/ml | 3 | 22-36 day) | 2% | NS |
| pGBI5-LP 0.44 mg/ml | 4 | 22-36 days | 4% | NS |
| pGBI5-LP 0.088 mg/ml | 5 | 22-36 days | 6% | NS |

TABLE 9-continued

Treatment outcomes for TGD in MDA-MB-231 xenograft tumors.

| Treatments | Group | TTE Range | TGD | Significance vs Control |
|---|---|---|---|---|
| D5W Control | 6 | 21.0 days (22-36 days) | n/a | n/a |

TTE = Time to endpoint; TGD = Tumor growth delay; n/a = not applicable; NS = Not significant (P > 0.05); * = Treatment related death.

Overall, the regimens were well tolerated and there was again no adverse survival effect demonstrated in the MDA-MB-231 human breast adenocarcinoma xenograft model.

Histopathology: There was no significant difference in tumor histomorphology across the six experimental groups. Tumors were morphologically consistent with carcinomas and showed variable degrees of necrosis, inflammation, mineralization, fibrosis, and/or hemorrhage.

Study 3: RE-PTL 135. Human melanoma cell line A2058 was used to evaluate the survival effect of pbi-shRNA™ STMN1-LP and pGBI5-LP in female Harlan rnu/rnu nude rats (Charles River Discovery Services, Piedmont Research Center) in RE-PTL-135. Xenograft tumors were initiated by injecting 1×107 A2058 tumor cells into the right flank of the test rats. The study included six test groups (n=20) that received 114 ul/animal of one of the following, pbi-shRNA™ STMN1-LP at either 0.44 or 0.088 mg/ml, pGBI5-LP at either 0.44 or 0.088 mg/ml, 5% dextrose in de-ionized water (D5W) or empty liposome at 10 mg/ml. IT injections were administered for all groups on Days 1, 5, 9, 13, and 17. The animals reached endpoint before receiving the last injection on Day 21. Animals were euthanized at the end of study (Day 20) or when their tumors reached the specified endpoint volume of 10,000 mm3. Treatment outcome was determined by tumor growth delay (TGD), defined as the increase in the median time to endpoint (TTE) in a treatment group compared to the D5W control group. Regression response was also considered as a part of treatment efficacy during the study. Complete regression, where the tumor volume was less than 13.5 mm3 for three consecutive measurements, was classified as a tumor-free survivor (TFS). The two-tailed logrank test was used to determine the statistical significance of the difference between the overall survival of a treatment group versus the D5W control group.

Results: The median TTE was 14.8 days, establishing a maximum possible TGD of 5.2 days (35%). The D5W control group, empty liposome group and pbi-shSTMN1 LP high dose (0.44 mg/ml) each contained three survivors. There was one non-treatment related (NTR) death in Group 5; the remaining nineteen tumors in Group 5 (pGBI5-LP at 0.088 mg/ml) exceeded the maximum endpoint volume (10,000 mm3) before the designated endpoint of the study, requiring the animal to be sacrificed prior to Day 20. The outcome was significantly worse (P<0.05) compared to the control D5W group (Table 10) based on survivorship, however the injected agent did not lead to premature death as the tumors in this group reached maximum size requiring sacrifice. There were no TFS in any of the groups. There was a treatment related (TR) death in Group 4 (pGBI5-LP 0.44 mg/ml). Treatment related deaths are classified as attributable to treatment side effects as evidenced by clinical signs and/or necropsy, or due to unknown causes during the dosing period or within 14 days of the last dose. Substantial body weight loss consistent with drug toxicity was observed for this test animal. Animals classified as TR deaths were assigned a TTE value equivalent to the day of death. The NTR death in Group 5 (pGBI5-LP, 0.088 mg/ml) was due to human error as the test animal was sacrificed too early. Animals classified as NTR due to accident or human error were excluded from all calculations.

TABLE 10

Treatment outcomes for TGD in A2058 xenograft tumors.

| Treatments | Group | TTE Range | TGD | Significance vs Control |
|---|---|---|---|---|
| Empty Liposome | 1 | 13.1-20 days | −1% | NS |
| pbi-shRNA™ STMN1-LP 0.44 mg/ml | 2 | 13.1-20 days | −6% | NS |
| pbi-shRNA™ STMN1-LP 0.088 mg/ml | 3 | 13.1-19.1 days | −3% | NS |
| pGBI5-LP 0.44 mg/ml | 4 | 13.1-20 days | 0% | NS |
| pGBI5-LP 0.088 mg/ml | 5 | 13.0-18.3 days | −5% | P < 0.05*** |
| D5W Control | 6 | 13.3-20 days | n/a | n/a |

TTE = Time to endpoint; TGD = Tumor growth delay; n/a = not applicable; NS = Not significant (P > 0.05);
*= Treatment related death;
**= Non-treatment related death;
***= Outcome was significantly worse than D5W control group. There were no survivors reported for this group whereas three survivors were present in the D5W control group.

No adverse survival difference was demonstrated with pbi-shRNA™ STMN1 LP and controls.

Histopathology: There was no significant difference in tumor histomorphology across the six experimental groups. Tumor cells were present in all tumors and showed variable degrees of necrosis, inflammation, mineralization, fibrosis, and/or hemorrhage.

Biodistribution data RE-PTL-125: A biodistribution study (RE-PTL-125) was performed to study distribution of pbi-shRNA™ STMN1 LP over three months after a single subcutaneous injection into biorelevant Sprague Dawley rats (6-7 week old male and female rats, at least 150 g at the time of treatment). All phases of this study were conducted in accordance with 21 CFR, Part 58, Good Laboratory Practice for Non-clinical Laboratories Studies. The in-life portion of the study was performed by Charles River Laboratories (Spencerville, Ohio). DNA extraction and plasmid DNA analysis of tissues was performed by Harlan Laboratories, Inc. (Switzerland). Gradalis, Inc. performed the RNA analysis and immune function assays.

This study determines temporal biodistribution and innate immune response to a single subcutaneous (SC) injection of pbi-shRNA™ STMN1 LP, in normal, healthy rats that are fully capable of mounting an immune response. There is a total of three treatment groups in the study (Table 11). The SC injections were administered as a single slow and even infusion for at least one minute of 100 μg pbi-shRNA™ STMN1 DNA in a total volume of 220 μl.

TABLE 11

Study design for subcutaneous injection of pbi-shRNA™ STMN1 LP in rats.

| Group | Treatment | Dose | Injection Volume | Total number of Rats |
|---|---|---|---|---|
| 1 | pbi-shRNA™ STMN1 LP | 100 ug | 220 ul | 50 female, 50 male |
| 2 | D5W (diluent control) | N/A | 220 ul | 50 female, 50 male |
| 3 | Non-treated | N/A | None | 5 female, 5 male |

Rat body weight was measured weekly for the entire study. After injection, 10 rats from each group (5 female and 5 male) were sacrificed at 1 of 10 time points post injection: 6 hr, 24 hr, 48 hr, Day 3, Day 4, Day 7, Day 14, Day 30, Day 60 and Day 90 (Table 12). Surviving rats were monitored for up to three months. At necropsy, blood and various internal organs (13 total) were collected for immune and molecular analysis. Animals were euthanized by cervical dislocation following administration of $CO_2$ at the first sign of distress or as scheduled.

TABLE 12

Sacrifice schedule of animals following single SC injection of either pbi-shRNA ™ STMN1 LP or D5W control.

| Time of sacrifice | Animals sacrificed | Collection of blood for plasma (ELISA) | Collection of tissues for molecular analysis |
|---|---|---|---|
| 6 hr | 5 F/5 M | Yes | No |
| 24 hr | 5 F/5 M | Yes | Yes |
| 48 hr | 5 F/5 M | Yes | Yes |
| Day 3 | 5 F/5 M | Yes | Yes |
| Day 4 | 5 F/5 M | Yes | Yes |
| Day 7 | 5 F/5 M | Yes | Yes |
| Day 14 | 5 F/5 M | No | Yes |
| Day 30 | 5 F/5 M | No | Yes |
| Day 60 | 5 F/5 M | No | Yes |
| Day 90 | 5 F/5 M | No | Yes |

Prior to analyzing study samples, the method for the quantification of pGBI2 plasmid DNA was validatated by Harlan (Switzerland) to define linearity, accuracy, efficacy, limit of detection and limit of quantification. The amplification range tested 108, 107, 106, 105, 104, 103, 102, 80, 40, 25, 10, 5, 2.5 and 1 copy. The standard curve derived from the validation had an upper-limit of quantification (ULOQ) of 108 copies and a lower-limit of quantification (LLOQ) of 25 copies. Samples with a Cq≥38 cycles was considered negative. The limit of detection established was 1 copy. Also, the presence of rat genomic DNA was found to have no effect on the quantification method.

Approximately 300 mg of each tissue was homogenized in a guanidinium thiocyanate based buffer. DNA was then extracted from the homogenate. Plasmid detection was determined by qPCR reaction using 1 μg of total DNA per well tested in triplicate. Each qPCR plate contained a standard curve used to determine plasmid DNA copy number per μs of total DNA by comparing the average Cq value of each sample against the standard curve on each plate. The limit of quantification (LOQ) was determined independently for each plate. The standard deviation of each plate was found to be ±1 Cq cycle. A total of 150 plates were analyzed containing extracted DNA from all the samples from Day 1, 2, 3, 4, 7, 14 and 30. As per FDA guidelines, samples with a determined copy number value of ≥50 copies/ug total DNA were considered positive for pDNA detection.

For mature shRNA expression, the stem-loop RT-QPCR method was used (as described in Section 1.3) for analysis with the same homogenates as used for pDNA detection. The lower limit of quantitation (LLOQ) for mature shRNA was determined to be 73.04 fmole/g tissue.

Results: Plasmid DNA Distribution: The biodistribution pattern of pbi-shSTMN1 pDNA detection was established over seven time points, Day 1 (24 hr), 2 (48 hr), 3, 4, 7, 14 and 30 by qPCR (Table 13). Tissues from Day 60 and Day 90 time points were not analyzed because no plasmid was detected beyond the Day 14 time point.

TABLE 13

Samples with detectable levels of pbi-shSTMN1 pDNA after a single SC injection in rats.

| | Day 1 | Day 2 | Day 3 | Day 4 | Day 7 | Day 14 | Day 30 |
|---|---|---|---|---|---|---|---|
| Blood | 4 | | 2 | | | | |
| BM | | | | 1 | | | |
| Brain | 1 | | 1 | 1 | | | |
| Diaphragm | 1 | | 1 | | | | |
| Heart | | | | | | | |
| Kidney | 2 | | | | | 1 | |
| Liver | 1 | | 2 | | | | |
| LN | 4 | | 1 | 1 | 1 | 1 | |
| Lung | 7 | 4 | 8 | 8 | 7 | 2 | |
| Muscle | 1 | | 1 | | | | |
| Inj. Site (Skin) | 10* | 10 | 10* | 9** | 9 | 3 | |
| Spleen | 5 | 5 | 10 | 3 | 5 | 2 | |
| Testes | | | | | | | |
| Ovaries | 2 | 1 | 1 | | 1 | | |
| Total | 38 | 20 | 37 | 23 | 23 | 9 | 0 |

Positive samples have copy number detection ≥ 50 copies.
*= one D5W control sample detected as positive;
**= two D5W control samples detected as positive.

Overall, the injection site (skin), spleen and lung contain the most number of animals with detectable levels of pDNA over a period of 14 days. Day 1 and Day 3 show widespread pDNA distribution, with plasmid detected in all tissues except the bone marrow, heart and testes in Day 1 and the bone marrow, heart, kidney and testes in Day 3. There is a marked decrease in pDNA detection by Day 14 and no plasmid was detected by Day 30 in any tissues.

No plasmid was detected in the heart or testes at any time point. The bone marrow, brain, diaphragm, kidney, liver, muscle and ovaries are positive for pDNA detection in less than samples overall out of 70 total animals per group.

Four (n=70) D5W-treated control animals from Day 1, 3 and 0.4 presented with detectable levels of plasmid DNA in the injection site (skin). The copy number for all four samples were 64.7 copies (day 1), 139.0 copies (day 3), 60.9 copies (day 4) and 60.0 copies (day 4). This could be explained by interplate variation, which could account for the copy number being calculated as higher than 50 copies, or due to experimental error. No other false positive samples were detected in any other time points in the skin or any other tissue evaluated.

Mature shRNA Expression Distribution: The biodistribution pattern of mature shRNA transcribed from pbi-shSTMN1 LP in 13 rat tissues (including blood) was investigated. It is the mature shRNA that complexes with RISC and executes the RNAi interference function on STMN1 mRNA.

For the tissues collected from the injection sites, the mature shRNA was detected from the samples of day 1, 2, 3, 4 and 7 post-injection. No mature shRNA was detected from samples of day 14 and day 30 post-injection. The mature shRNA had an expression range of 93.78-38,322.45 fmole/g tissue in the injection sites.

For the injection sites, mature shRNA expression emerged as early as 24 hours post-injection and was detectable at 7 days with a median value of $1.98 \times 10^4$ fmole/g tissue. The samples at day 14 and day 30 did not display detectable expression of mature shRNA targeting STMN1. The results suggest that the exogenous mature shRNA persists but for no more than 0.7 days but less than 14 days after a single subcutaneous injection in rats.

Three out of 10 samples from day 2, 3, 4, 7 post-injection were determined as positive, while 2 out of 10 samples were determined as positive from day 1 post-injection from the injection. 300 mg of tissue was homogenized and used for mature shRNA measurement, which represents about 30-60% of the skin tissue harvested from the injection site. The possibility that the mature shRNA expression may not be evenly distributed in the injection sites and that some animals with undetectable mature shRNA expression were actually positive cannot be ruled out. Another explanation is that the subcutaneous injection may deliver the plasmid to different parts of the hypodermis layer, where the composition of cell types determines the transfection efficiency and mature shRNA processing. The expression of mature shRNA could be more efficient in rapidly proliferating cells, such as adipocytes, histocytes and fibroblasts in the subcutis layer.

For all the organs (excluding the injection sites) collected on day 1 and day 2 post-injection, there was no detectable level of mature shRNA transcribed from pbi-shSTMN1 LP. Therefore, no measurement of mature shRNA was taken on tissues harvested beyond day 2 post-injection.

Even though plasmid was detected from a variety of organs at different time points, including blood, lung, liver, heart, spleen, and kidney, no mature shRNA targeting STMN1 was detected from the same tissues in which plasmid was detected. This suggests that even though the plasmid was delivered to those organs, the transcribed mature shRNA was at a low level that may not be sufficient to execute the RNA interference function. The results further suggest that the subcutaneous injection of pbi-shSTMN1 LP may not elicit shRNA-mediated toxicities or side effects in major organs due to inability to provide sufficient material enabling detectable expression of mature shRNA.

Immune function analysis is pending and consists of plasma cytokine determinations at 7 timepoints (day—5, 6, 24 and 48 hours; 3, 4 and 7 days post-injection). ELISA assays for rate IL-1β, IL-6, TNFα and INFβ are being conducted to determine if there are any significant post-injection cyctokine expression changes.

Toxicology data: RE-PTL-106 Design: Study RE-PTL-106 was performed to determine safety and toxicity of the pbi-shRNA™ STMN1 LP) over 3 months, after a single intravenous injection to Harlan-Sprague Dawley rats (6-7 week old male and female rats, at least 150 g at the time of treatment). This study was a non-GLP study except for the work performed by Texas A&M University (TAMU), which was conducted in accordance with 21 CFR, Part 58, Good Laboratory Practice (GLP) for Non-clinical Laboratory Studies.

All animal care and related study procedures conducted at UNT were not blinded during the course of the study. All blood and serum analysis conducted by Research Animal Diagnostic Laboratory (RADIL), Columbia, Mo. and all histopathology analysis conducted by TAMU was performed in a blinded manner.

This study examined safety and toxicity of pbi-shRNA™ STMN1 LP when administered as a single IV injection to normal, healthy rats that were fully capable of mounting an immune response. There were a total of 5 groups in the study (Table 14). Each group consisted of 60 rats (30 male and 30 female). Three (3) groups were given pbi-shRNA™ STMN1 LP at one of 3 doses: 1.5, 15, and 150 ug. These doses were equivalent to 0.4, 4 and 40 ug doses respectively in immune-competent mice (weighing 20 g). Two (2) groups served as controls and were injected with either empty liposomes or the diluent (D5W) only (Table 8).

Rat body weight was measured every week for the duration of the study. Ten rats (5 male and 5 female) from each group were sacrificed at one of 6 time points (Days 2, 7, 14, 30, 60, or 90) post-treatment, and blood and internal tissues were harvested. Blood was collected for toxicology analysis (CBC, serum chemistry and coagulation tests). Tissues were collected for histopathology analysis. At the first sign of distress during the study period, animals were euthanized by cervical dislocation following administration of anesthesia as per IACUC requirements at University of North Texas, Fort Worth, Tex. FFPE tissues were sectioned and stained using H&E at the Animal Resources Center, UT Southwestern Medical Center, Dallas, Tex. Histopathology analysis is currently being performed at CVP laboratory at TAMU, College Station.

TABLE 14

(RE-PTL-106) Rat groups for intravenous injections.

| Treatment | Total Number of Rats* |
|---|---|
| 1.5 ug pbi-shRNA ™ STMN1 LP | 30 female 30 male |
| 15 ug pbi-shRNA ™ STMN1 LP | 30 female 30 male |
| 150 ug pbi-shRNA ™ STMN1 LP | 30 female 30 male |
| 0 ug D5W | 30 female 30 male |
| 0 ug Empty Liposome | 30 female 30 male |

*5 male and 5 female rats per treatment group were sacrificed per time point (Days 2, 7, 14, 30, 60 and 90 days post injection).

Groups of rats were injected in batches to account for scheduling issues and ability to perform complete necropsies on only 10 rats in a single day. Thus, only 10 rats were injected IV on any single day. As a result 50 rats that were to be sacrificed for a time-point, were divided among 5 days with 10 rats being sacrificed per day.

All data analyses were performed using SPSS13.0 software (SPSS Inc; Chicago, Ill.).

Differences in various CBC and serum chemistry parameters were analyzed at specific time-points (Days 2, 7, 14, 30, 60 and 90) or within a dose group by oneway analysis of variance (ANOVA). Post-hoc comparisons were made using the Tukey test to identify specific groups varying in these parameters.

Differences in rat body weights between treatment groups at specific time-points were determined using oneway ANOVA. Post-hoc comparisons were made using the Tukey test.

Repeated Measures ANOVA (post-hoc Tukey test) was performed to determine differences in rat body weights over time.

RE-PTL-106 Results: Cage-side Observations: Treatment with diluent (D5W) or empty liposomes did not demonstrate toxicity in the animals. Administration of pbi-shRNA™ STMN1 LP at doses of either 1.5 or 15 ug also did not lead to behavioral changes in any animal during the period of the study. 1/60 animals treated with pbi-shRNA™ STMN1 LP at a dose of 150 ug died within 24 hrs post-injection. 15/59 surviving rats treated with 150 ug pbi-shRNA™ STMN1 LP demonstrated behavioral changes which resolved by 24 hrs. None of the surviving rats demonstrated any toxicity beyond 24 hrs.

Rat Body Weights: The rat body weights were not affected adversely by the administered treatments. See Appendix 3.

Coagulation and Serum chemistry: Although serum chemistry parameters (e.g.: creatinine, AST, sodium, potassium, etc.) demonstrated significant differences (either higher or lower than the reference range of the assay), their exact levels were not different enough from the reference range to be considered "biologically relevant differences." See Appendix 4

Coagulation: PT and PTT values of >60 and >120 respectively were excluded from statistical analysis. This could be attributed to technical error while sampling blood. All treatment and control groups demonstrated normal PT levels at all time-points. PTT levels, for the most part, were within the normal range of the assay. Rats treated with 150 ug pbi-shRNA™ STMN1 LP demonstrated elevated levels compared to the reference range on Days 2 and 90. Empty liposome group also demonstrated markedly higher levels for PTT assay on Day 90, which differed from 1.5 ug, 15 ug and D5W groups. There was neither a dose nor time-dependent trend observed for the coagulation tests, which were primarily normal.

Glucose: With the exception of Day 7, glucose levels on Days 2, 14, 30, 60 and 90 demonstrated elevated levels for at least 1 treatment group as compared to the reference range. Treatment with diluent led to elevated glucose levels only on Days 30 and 60. Treatment with empty liposomes led to elevated glucose levels on Days 2, 30 and 60. Although glucose levels were higher compared to the reference range for certain study groups, correlation of glucose levels with effect of lipoplexes cannot be determined conclusively as all the rats were fed ad libitum. Moreover, the glucose alterations were also observed in the control groups indicating absence of an effect related to pbi-shRNA™ STMN1 LP administration.

Kidney function (Creatinine, Urea nitrogen, Creatine kinase): Urea nitrogen levels were normal throughout the study period for all the treatment and control groups. Creatinine levels were also normal with some minor alterations on Days 2 and 7, which resolved to fall within the reference range on subsequent time-points. Creatine kinase levels were normal for all treatment and control groups on Days 2, 7, 14, 30 and 60. On Day 90, creatine kinase levels for the highest dose group (150 ug pbi-shRNA™ STMN1 LP) were significantly elevated compared to the reference range and other treatment groups (which demonstrated normal creatine kinase levels). Kidney function was normal after treatment with 3 doses of pbi-shRNA™ STMN1 LP with the exception of the Day 90 time-point for the 150 ug dose group.

Liver function (Albumin, total bilirubin, ALT, ALP, AST): Albumin and ALP levels were normal for all treatment and control groups at all time-points: Total bilirubin levels were also within the normal reference range for all groups on Days 2, 30, 60 and 90. Minor alterations were observed at the lower concentrations of the pbi-shRNA™ STMN1 LP treatment (1.5 ug and 15 ug) on Days 7 and 14. On these 2 days, total bilirubin levels were normal for the 150 ug dose group and groups dosed with empty liposomes or D5W. ALT levels were within the reference range for all treatment and control groups throughout the study period with minor alterations demonstrated on Day 14 by the groups treated with 1.5 ug and empty liposomes. AST levels were within the reference range for all treatment and control groups on Days 7 and 60. On Days 2, 14, 30 and 90, AST levels were either below the reference range or were altered at the lowest dose group or by empty liposomes. There was neither a dose nor time-dependent trend observed for the liver function tests.

Electrolytes (sodium, potassium and chloride): Chloride levels were within the reference range throughout the study period with the exception of the 1.5 ug group on Day 14. Overall, sodium levels tended to be lower than the reference range of the assay. Although potassium levels demonstrated significant elevation, these were not considered to be biologically relevant. Overall, potassium levels demonstrated only minor alterations for the treatment and control groups. The electrolyte profile did not display any dose-dependent or time-dependent alterations.

With the exception of elevated creatine kinase levels on Day 90 for the highest dose group and elevated AST levels for the lowest dose group on Day 14, the serum chemistry parameters did not demonstrate dose- or time-dependent alterations.

Complete Blood Counts: Administration of pbi-shRNA™ STMN1 LP did not significantly alter the complete blood counts in treated animals. The only exception was reduced platelet counts that were observed on Day 2 for animals treated with 150 ug pbi-shRNA™ STMN1 LP. Platelet counts were within normal reference range for this group for all the latter time-points.

Pathology: Glass slides from paraffin embedded tissue were submitted to the Texas A&M University, Translational Pathology Research Laboratory. Pathologists were blinded with regard to treatment group and time period therefore animal number and gender were used to generate reports. After completion of the qualitative evaluation the pathologists were informed of the treatment group and time period data to facilitate in depth analysis and evaluation of the preliminary findings.

In potential target organs (lungs, heart, kidneys, skeletal muscle) no consistent gross or microscopic lesions were attributable to any of the treatments. There were no statistically significant histological changes in any treatment group at any post-treatment time period that indicated an adverse effect on any target organ.

Gross and histological changes identified in "non-target" organs were sporadic, infrequent, and did not correspond to any particular treatment group in the study.

In conclusion, the pathology assessment showed that for the six time periods evaluated the systemic effect of injected pbi-shRNA™ STMN1 LP were within established safety standards; thus, pbi-shRNA™ STMN1 LP within the scope of this Study was safe and caused no adverse effects when injected intravenously.

RE-PTL-127 Design: Study RE-PTL-127 was performed to determine safety and toxicity of the pbi-shRNA™ STMN1 LP over a 3 month period after a single subcutaneous injection into Sprague Dawley rats (6-7 week old male and female rats, at least 150 g at the time of treatment). All phases of this study were conducted in accordance with 21 CFR, Part 58, Good Laboratory Practice (GLP) for Non-clinical Laboratory Studies. One subcutaneous injection of either pbi-shRNA™ STMN1 LP, empty lipsome, or D5W control agent was administered on Day 0 in the scapular/mid-dorsal region of each test animal (Table 15).

TABLE 15

Experimental Design.

| Group No. | Males | Females | Test Material | Dose Volume (ul/dose) |
|---|---|---|---|---|
| 1 | 45 | 45 | pbi-shRNA ™ STMN1 LP | 220 |
| 2 | 45 | 45 | Empty Liposome | 220 |
| 3 | 45 | 45 | D5W | 220 |

Test animals, 5 males and 5 females from each treatment group (n = 30), were necropsied on Day 1, 2, 3, 4, 7, 14, 30, 60, and 90.

All personnel performing observations, clinical pathology and necropsies were blinded to the test articles. The study director was not blinded to the test articles. Histology and histopathology were performed on the necropsied tissues.

RE-PTL-127 Summary of Results: No mortality occurred during the duration of the toxicity study. Also, no effects on body weight, organ weight, hematology and coagulation parameters, or clinical chemistry parameters were observed during the study. It was found that raised areas developed at the location of the administration of the pbi-shRNA™

STMN1 LP and the empty liposome treated animals. Raised areas in the pbi-shRNA™ STMN1 LP treated animals persisted whereas those observed in the empty liposome treated animals resolved by Day 30. The raised areas seem to be liposome related since they occurred in both the treatment groups and were not observed in the D5W treated control animals.

For gross pathology, liposome-related changes were observed at the injection site during necropsy. Thickening, pale areas, dark areas, and mottled areas were observed at Day 1-Day 4 in animals treated with pbi-shRNA™ STMN1 LP and empty liposome. By Day 7, thickening was no longer observed and by Day 14, only pale areas persisted at the injection site. Pale areas were observed at Days 30, 60, and 90 only in the pbi-shRNA™ STMN1 LP treated animals.

For histopathology, minimal to moderate subcutaneous sterile inflammatory foci characterized by a central focus of fibrin, degenerating neutrophils and basophilic material was found at the injection site of pbi-shRNA™ STMN1 LP treated animals. This was presumed to be the area of necrotic connective tissue surrounding the injection site. There was also mild to moderate acute inflammation of the subcuticular tissue around the injection site foci. These sterile inflammatory foci were resolved by Day 14, except edema, but the subacute inflammation remained. By Day 30, many of the injection site lesions had resolved but animals treated with pbi-shRNA™ STMN1 LP or empty liposome still showed signs of minimal chronic inflammation or granulomas.

Overall, the subcutaneous injection of pbi-shRNA™ STMN1 LP was well tolerated by rats. Changes were mainly related to the injection site at gross pathology. These changes appear to be related to the liposome rather than the active pbi-shRNA™ STMN1 summary of unscheduled deaths: Summary of unscheduled animal deaths are outlined in Table 16.

TABLE 16

Summary of animal numbers and sacrifice intervals for various studies.

| Animal Study | Animal Report Reference | Number of animals used in Study | Purpose of Study (tumor model) | Unscheduled Deaths | Time of Sacrifice |
| --- | --- | --- | --- | --- | --- |
| RE-PTL-105 | RE-TIR-120 | 50 athymic nude mice | Assess efficacy (CCL-247 tumor xenograft) | None | 2 weeks after the last IT injection |
| RE-PTL-107 | RE-TIR-125, 129, 153, 154, 155, 158 | 60 athymic nude mice | Assess efficacy (CCL-247 tumor xenograft) | None | Day 32 (n = 48 mice) or 48 hr (n = 12) after the last IT injection |
| RE-PTL-115 | RE-TIR-156, 161, 164 | 48 athymic nude mice | Assess efficacy (CCL-247 tumor xenograft) | None | Day 26 after the last IT injection |
| RE-PTL-114 | RE-TIR-144, 143, 146, 147 | 75 athymic nude mice | Assess STMN knockdown (CCL-247 tumor xenograft) | None | 24, 48, 72 hr after the last IT injection |
| RE-PTL-120 | RE-TIR-191 | 51 nude mice | Assess efficacy (Low passage primary Melanoma tumorgraft) | None | Day 26 after the last IT injection |
| RE-PTL-109 | RE-TIR-110, 111, 112, 113, 116, 118, 122, 128, 130, 131, 132, 133, 138, 139, 140, 142, 145, 149 | 57 athymic nude mice | Assess efficacy (low passage primary Osteoscarcoma tumorgraft) | None | At various times during the study after the last IT injection |
| RE-PTL-133 | RE-TIR-252 | 120 female Harlan rnu/rnu nude rats | Efficacy/Survival | None | Day 43, or when tumor size reaches 5,000 mm$^3$ |
| RE-PTL-134 | RE-TIR-253 | 120 female Harlan rnu/rnu nude rats | Efficacy/Survival | 1* | Day 36, or when tumor size reaches 8,000 mm$^3$ |
| RE-PTL-135 | RE-TIR-254 | 120 female Harlan rnu/rnu nude rats | Efficacy/Survival | 2** | Day 20, or when tumor size reaches 5,000 mm$^3$ |
| RE-PTL 125 | RE-TIR-250, 259 | 210 Sprague Dawley rats (105 males and 105 females) | Biodistribution | None | Days 1, 2, 3, 4, 7, 14, 30, 60, and 90 after single subcutaneous injection |

TABLE 16-continued

Summary of animal numbers and sacrifice intervals for various studies.

| Animal Study | Animal Report Reference | Number of animals used in Study | Purpose of Study (tumor model) | Unscheduled Deaths | Time of Sacrifice |
|---|---|---|---|---|---|
| RE-PTL-127 | RE-TIR-251 | 270 rats (135 males and 135 females) | Toxicology | None | Days 1, 2, 3, 4, 7, 14, 30, 60, and 90 after single subcutaneous injection |

*female rat, died on Day 22, pGBI5-LP 0.44 mg/ml;
**one female rat died on Day 20, pGBI5-LP 0.44 mg/ml; one female rat was euthanized for sampling too early, was classified as a non-treatment related death and was censored from analysis;
***female rat, died 24 hours post, high dose (150 ug) injection.

Preclinical Studies, In vivo animal studies; Safety Analysis: GNE lipoplexes have been tested in vivo by intramuscular injection into Balb/c mice. The pUMVC3-GNE DNA was complexed with DOTAP:Chol and administered to Balb/c mice via IM injection. Six male and six female mice per cohort were given a single dose of 0, 10, or 40 ug DNA and observed for signs per dose level of toxicity. None of the animals displayed signs of acute toxicity and the animals were sacrificed 2 weeks post injection. Major organs were collected (liver, lung, spleen, kidney, injected muscle, and non-injected muscle) and analyzed by RT-qPCR for GNE expression. The murine tissues from this toxicology study were cryopreserved, sectioned, and stained with H&E. A certified veterinary pathologist examined the slides from each tissue harvested, at each dose administered.

Uninjected group: No unexpected abnormalities were identified in any organs involving the 12 mice. Myodegeneration (or possible artifact) was noted in the right muscle of 1/12 mice. Six of 12 livers showed common expected abnormalities (2/12 extramedullary hematopoiesis, 1/12 cholangitis, 3/12 vacuolation).

1.1.2 0 ug DNA:lipoplex: No unexpected abnormalities were identified in any organ involving the 12 mice. Minimal cholangitis and diffuse hepatocyte vacuolation was observed in 2 livers, but these were not different from the uninjected group. Four of 12 mice demonstrated lesions in the injected right muscle. Myodegeneration with little or no inflammatory response and associated tissue mineralization was noted in 2 mice. Inflammatory response accompanying myofiber degeneration primarily comprising of histiocytes and a few lymphocytes was noted in 2 mice. The myopathic changes were attributed to the IM injection.

10 ug DNA:lipoplex: No unexpected abnormalities were identified in any organ involving the 12 mice. Mild, diffuse hepatocyte vacuolation was observed in 1 liver, but this was not different from the uninjected group. Only one of the 12 mice demonstrated lesion in the injected right muscle. Myodegeneration with inflammatory response and associated tissue mineralization was noted in 1 mouse. The myopathic changes were attributed to localized tissue trauma due to the 1M injection.

40 ug DNA:lipoplex: No unexpected abnormalities were identified in any organ involving the 12 mice. Minimal hepatocyte vacuolation was observed in 1 liver, but this was not different from the uninjected group (Table 1). Six of 12 mice had a lesion in the injected right muscle. Myodegeneration and associated tissue mineralization was noted in 5 mice. Mild to moderate inflammatory response accompanying mineralization was noted in 1 mouse. The myopathic changes were attributed to localized tissue trauma due to the IM injection. Representative photomicrographs of injected and uninjected control muscles are shown in FIG. 1.

TABLE 17

Mouse Histopathology Summary.

| | Observations | Untreated | 0 ug | 10 ug | 40 ug |
|---|---|---|---|---|---|
| 1 | Gross histopathology | No unexpected abnormalities for any tissue examined | No unexpected abnormalities for any tissue examined | No unexpected abnormalities for any tissue examined | No unexpected abnormalities for any tissue examined |
| 2 | Myodegeneration and tissue mineralization (right injected muscle) | 1 | 2 | — | 5 |
| 3 | Myodegeneration and Myositis (right injected muscle) | — | 2 | 1 | 1 |
| 4 | Cholangitis | 1 | 1 | — | — |
| 5 | Hepatocyte Vacuolation | 3 | 1 | 1 | 1 |
| 6 | Extramedullary hemtopoiesis | 2 | — | — | — |
| 7 | Bile duct hyperplasia | 1 | — | — | — |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

SEQUENCE LISTING

```
<160> NUMBER OF SEQ ID NOS: 10

<210> SEQ ID NO 1
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 1
ggcacaaatg gctgccaaa                                                  19

<210> SEQ ID NO 2
<211> LENGTH: 19
<212> TYPE: DNA
<213> ORGANISM: artificial sequence
<220> FEATURE:
<223> OTHER INFORMATION: synthetic oligonucleotide
```

-continued

```
<400> SEQUENCE: 2
ggcgcaaatg gctgccaag                                                    19

<210> SEQ ID NO 3
<211> LENGTH: 147
<212> TYPE: DNA
<213> ORGANISM: artificial sequence
<220> FEATURE:
<223> OTHER INFORMATION: synthetic oligonucleotide

<400> SEQUENCE: 3
tgctgttgac agtgagcgcg gcacaaatgg ctgccaaata gtgaagccac agatgtattt       60
ggcagccatt tgtgccttgc ctactgcctc ggaagcttaa taaggatct tttattttca      120 ttggatctgt gtgttggttt tttgtat                                         147

<210> SEQ ID NO 4
<211> LENGTH: 147
<212> TYPE: DNA
<213> ORGANISM: artificial sequence
<220> FEATURE:
<223> OTHER INFORMATION: synthetic oligonucleotide

<400> SEQUENCE: 4
tgctgttgac agtgagcgcg gcacaaatgg ctgccaaata gtgaagccac agatgtattt       60
ggcagccatt tgtgccttgc ctactgcctc ggaagcttaa taaggatct tttattttca      120 ttggatctgt gtgttggttt tttgtat                                         147

<210> SEQ ID NO 5
<211> LENGTH: 147
<212> TYPE: DNA
<213> ORGANISM: artificial sequence
<220> FEATURE:
<223> OTHER INFORMATION: synthetic oligonucleotide

<400> SEQUENCE: 5
tgctgttgac agtgagcgcg gcacaaatga ttgccaaata gtgaagccac agatgtattt       60
ggcagccatt tgtgccttgc ctactgcctc ggaagcttaa taaggatct tttattttca      120 ttggatctgt gtgttggttt tttgtat                                         147

<210> SEQ ID NO 6
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 6
cgccaccaga cataatagct gaca                                              24

<210> SEQ ID NO 7
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 7
tagccagaag tcagatgctc aagg                                              24
```

<210> SEQ ID NO 8
<211> LENGTH: 4122
<212> TYPE: DNA
<213> ORGANISM: artificial sequence
<220> FEATURE:
<223> OTHER INFORMATION: synthetic oligonucleotide

<400> SEQUENCE: 8

```
tggccattgc atacgttgta tccatatcat aatatgtaca tttatattgg ctcatgtcca      60
acattaccgc catgttgaca ttgattattg actagttatt aatagtaatc aattacgggg     120
tcattagttc atagcccata tatggagttc cgcgttacat aacttacggt aaatggcccg     180
cctggctgac cgcccaacga cccccgccca ttgacgtcaa taatgacgta tgttcccata     240
gtaacgccaa tagggacttt ccattgacgt caatgggtgg agtatttacg gtaaactgcc     300
cacttggcag tacatcaagt gtatcatatg ccaagtacgc cccctattga cgtcaatgac     360
ggtaaatggc ccgcctggca ttatgcccag tacatgacct tatgggactt tcctacttgg     420
cagtacatct acgtattagt catcgctatt accatggtga tgcggttttg gcagtacatc     480
aatgggcgtg atagcggttt gactcacggg gatttccaa gtctccaccc cattgacgtc     540
aatgggagtt tgttttggca ccaaaatcaa cgggactttc caaaatgtcg taacaactcc     600
gccccattga cgcaaatggg cggtaggcgt gtacggtggg aggtctatat aagcagagct     660
cgtttagtga accgtcagat cgcctggaga cgccatccac gctgttttga cctccataga     720
agacaccggg accgatccag cctccgcggc cgggaacggt gcattggaac gcggattccc     780
cgtgccaaga gtgacgtaag taccgcctat agactctata ggcaccccc tttggctctt     840
atgcatgcta tactgttttt ggcttgggc ctatacaccc ccgcttcctt atgctatagg     900
tgatggtata gcttagccta taggtgtggg ttattgacca ttattgacca ctccaacggt     960
ggagggcagt gtagtctgag cagtactcgt tgctgccgcg cgcgccacca gacataatag    1020
ctgacagact aacagactgt tccttttcca t gggtctttt tgcagtcacc gtcgtcgact    1080
gctgttgaca gtgagcgcgg cacaaatggc tgccaaatag tgaagccaca gatgtatttg    1140
gcagccattt gtgccttgcc tactgcctcg gaagcttaat aaaggatctt ttatttcat     1200
tggatctgtg tgttggtttt tgtatgcgg ccgcggatcc agatcttttt ccctctgcca    1260
aaaattatgg ggacatcatg aagccccttg agcatctgac ttctggctaa taaggaaat     1320
ttattttcat tgcaatagtg tgttggaatt ttttgtgtct ctcactcgga aggacatatg    1380
ggagggcaaa tcatttaaaa catcagaatg agtatttggt ttagagtttg gcaacatatg    1440
cccattcttc cgcttcctcg ctcactgact cgctgcgctc ggtcgttcgg ctgcggcgag    1500
cggtatcagc tcactcaaag gcggtaatac ggttatccac agaatcaggg gataacgcag    1560
gaaagaacat gtgagcaaaa ggccagcaaa aggccaggaa ccgtaaaaag gccgcgttgc    1620
tggcgttttt ccataggctc cgcccccctg acgagcatca caaaaatcga cgctcaagtc    1680
agaggtggcg aaacccgaca ggactataaa gataccaggc gtttccccct ggaagctccc    1740
tcgtgcgctc tcctgttccg accctgccgc ttaccggata cctgtccgcc tttctccctt    1800
cgggaagcgt ggcgctttct catagctcac gctgtaggta tctcagttcg gtgtaggtcg    1860
ttcgctccaa gctgggctgt gtgcacgaac cccccgttca gcccgaccgc tgcgccttat    1920
ccggtaacta tcgtcttgag tccaacccgg taagacacga cttatcgcca ctggcagcag    1980
ccactggtaa caggattagc agagcgaggt atgtaggcgg tgctacagag ttcttgaagt    2040
ggtggcctaa ctacggctac actagaagaa cagtatttgg tatctgcgct ctgctgaagc    2100
```

```
cagttacctt cggaaaaaga gttggtagct cttgatccgg caaacaaacc accgctggta    2160
gcggtggttt ttttgtttgc aagcagcaga ttacgcgcag aaaaaaagga tctcaagaag    2220
atcctttgat cttttctacg gggtctgacg ctcagtggaa cgaaaactca cgttaaggga    2280
ttttggtcat gagattatca aaaggatctc acctagat cctttttaaat taaaaatgaa    2340 gttttaaatc aatctaaagt atatatgagt aaacttggtc tgacagttac caatgcttaa    2400
tcagtgaggc acctatctca gcgatctgtc tatttcgttc atccatagtt gcctgactcg    2460 ggggggggg gcgctgaggt ctgcctcgtg aagaaggtgt tgctgactca taccaggcct    2520
gaatcgcccc atcatccagc cagaaagtga gggagccacg gttgatgaga gctttgttgt    2580
aggtggacca gttggtgatt ttgaactttt gctttgccac ggaacggtct gcgttgtcgg    2640
gaagatgcgt gatctgatcc ttcaactcag caaaagttcg atttattcaa caaagccgcc    2700
gtcccgtcaa gtcagcgtaa tgctctgcca gtgttacaac caattaacca attctgatta    2760
gaaaaactca tcgagcatca aatgaaactg caatttattc atatcaggat tatcaatacc    2820
atatttttga aaaagccgtt tctgtaatga aggagaaaac tcaccgaggc agttccatag    2880
gatggcaaga tcctggtatc ggtctgcgat tccgactcgt ccaacatcaa tacaacctat    2940
taatttcccc tcgtcaaaaa taaggttatc aagtgagaaa tcaccatgag tgacgactga    3000
atccggtgag aatggcaaaa gcttatgcat ttctttccag acttgttcaa caggccagcc    3060
attacgctcg tcatcaaaat cactcgcatc aaccaaaccg ttattcattc gtgattgcgc    3120
ctgagcgaga cgaaatacgc gatcgctgtt aaaaggacaa ttacaaacag gaatcgaatg    3180
caaccggcgc aggaacactg ccagcgcatc aacaatattt tcacctgaat caggatattc    3240
ttctaatacc tggaatgctg ttttcccggg gatcgcagtg gtgagtaacc atgcatcatc    3300
aggagtacgg ataaaatgct tgatggtcgg aagaggcata aattccgtca gccagtttag    3360
tctgaccatc tcatctgtaa catcattggc aacgctacct ttgccatgtt tcagaaacaa    3420
ctctggcgca tcgggcttcc catacaatcg atagattgtc gcacctgatt gcccgacatt    3480
atcgcgagcc catttatacc catataaatc agcatccatg ttggaattta atcgcggcct    3540
cgagcaagac gtttcccgtt gaatatggct cataacaccc cttgtattac tgtttatgta    3600
agcagacagt tttattgttc atgatgatat attttttatct tgtgcaatgt aacatcagag    3660
attttgagac acaacgtggc tttcccccc ccccattat tgaagcattt atcagggtta    3720
ttgtctcatg agcggataca tatttgaatg tatttagaaa aataaacaaa tagggggttcc    3780 gcgcacattt ccccgaaaag tgccacctga cgtctaagaa accattatta tcatgacatt    3840
aacctataaa aataggcgta tcacgaggcc ctttcgtctc gcgcgtttcg gtgatgacgg    3900
tgaaaacctc tgacacatgc agctcccgga cggtcaca gcttgtctgt aagcggatgc    3960
cgggagcaga caagcccgtc agggcgcgtc agcgggtgtt ggcgggtgtc ggggctggct    4020
taactatgcg gcatcagagc agattgtact gagagtgcac catatgcggt gtgaaatacc    4080
gcacagatgc gtaaggagaa aataccgcat cagattggct at               4122
```

<210> SEQ ID NO 9
<211> LENGTH: 4220
<212> TYPE: DNA
<213> ORGANISM: artificial sequence
<220> FEATURE:
<223> OTHER INFORMATION: synthetic oligonucleotide

```
<400> SEQUENCE: 9
tggccattgc atacgttgta tccatatcat aatatgtaca tttatattgg ctcatgtcca        60
acattaccgc catgttgaca ttgattattg actagttatt aatagtaatc aattacgggg       120
tcattagttc atagcccata tatggagttc cgcgttacat aacttacggt aaatggcccg       180
cctggctgac cgcccaacga cccccgccca ttgacgtcaa taatgacgta tgttcccata       240
gtaacgccaa tagggacttt ccattgacgt caatgggtgg agtatttacg gtaaactgcc       300
cacttggcag tacatcaagt gtatcatatg ccaagtacgc ccctattga cgtcaatgac       360
ggtaaatggc ccgcctggca ttatgccag tacatgacct tatgggactt cctacttgg        420
cagtacatct acgtattagt catcgctatt accatggtga tgcggttttg gcagtacatc       480
aatgggcgtg gatagcggtt tgactcacgg gatttccaa gtctccaccc cattgacgtc       540
aatgggagtt tgttttggca ccaaaatcaa cgggactttc caaaatgtcg taacaactcc       600
gccccattga cgcaaatggg cggtaggcgt gtacggtggg aggtctatat aagcagagct       660
cgtttagtga accgtcagat cgcctggaga cgccatccac gctgttttga cctccataga       720
agacaccggg accgatccag cctccgcggc cgggaacggt gcattggaac gcggattccc       780
cgtgccaaga gtgacgtaag taccgcctat agactctata ggcacacccc tttggctctt       840
atgcatgcta tactgttttt ggcttggggc ctatacaccc ccgcttcctt atgctatagg       900
tgatggtata gcttagccta taggtgtggg ttattgacca ttattgacca ctccaacggt       960
ggagggcagt gtagtctgag cagtactcgt tgctgccgcg cgcgccacca gacataatag     1020
ctgacagact aacagactgt tcctttccat gggtcttttc tgcagtcacc gtcgtcgact     1080
gctgttgaca gtgagcgcgg cacaaatggc tgccaaatag tgaagccaca gatgtatttg     1140
gcagccattt gtgccttgcc tactgcctcg gagatcctgc tgttgacagt gagcgcggca     1200
caaatgattg ccaaatagtg aagccacaga tgtatttggc agccatttgt gccttgccta     1260
ctgcctcgga agcttaataa aggatctttt attttcattg gatctgtgtg ttggtttttt     1320
gtatgcggcc gcggatccag atcttttttcc ctctgccaaa aattatgggg acatcatgaa     1380
gccccttgag catctgactt ctggctaata aggaaatttt attttcattg caatagtgtg     1440
ttggaatttt ttgtgtctct cactcggaag acatatgggg agggcaaatc atttaaaaca     1500
tcagaatgag tatttggttt agagtttggc aacatatgcc cattcttccg cttcctcgct     1560
cactgactcg ctgcgctcgg tcgttcggct gcggcgagcg gtatcagctc actcaaaggc     1620
ggtaatacgg ttatccacag aatcagggga taacgcagga agaacatgt gagcaaaagg     1680
ccagcaaaag gccaggaacc gtaaaaaggc cgcgttgctg gcgttttttcc ataggctccg     1740
ccccctgac gagcatcaca aaaatcgacg ctcaagtcag aggtggcgaa acccgacagg     1800
actataaaga taccaggcgt ttccccctgg aagctccctc gtgcgctctc ctgttccgac     1860
cctgccgctt accggatacc tgtccgcctt tctcccttcg ggaagcgtgg cgctttctca     1920
tagctcacgc tgtaggtatc tcagttcggt gtaggtcgtt cgctccaagc tgggctgtgt     1980
gcacgaaccc cccgttcagc ccgaccgctg cgccttatcc ggtaactatc gtcttgagtc     2040
caacccggta agacacgact tatcgccact ggcagcagcc actggtaaca ggattagcag     2100
agcgaggtat gtaggcggtg ctacagagtt cttgaagtgg tggcctaact acggctacac     2160
tagaagaaca gtatttggta tctgcgctct gctgaagcca gttaccttcg gaaaagagt     2220
tggtagctct tgatccggca aacaaaccac cgctggtagc ggtggttttt ttgtttgcaa     2280
gcagcagatt acgcgcagaa aaaaaggatc tcaagaagat cctttgatct tttctacggg     2340
```

```
gtctgacgct cagtggaacg aaaactcacg ttaagggatt ttggtcatga gattatcaaa    2400
aaggatcttc acctagatcc ttttaaatta aaaatgaagt tttaaatcaa tctaaagtat    2460
atatgagtaa acttggtctg acagttacca atgcttaatc agtgaggcac ctatctcagc    2520
gatctgtcta tttcgttcat ccatagttgc ctgactcggg ggggggggc gctgaggtct    2580 gcctcgtgaa gaaggtgttg ctgactcata ccaggcctga atcgcccat catccagcca    2640 gaaagtgagg gagccacggt tgatgagagc tttgttgtag gtggaccagt tggtgatttt    2700
gaacttttgc tttgccacgg aacggtctgc gttgtcggga agatgcgtga tctgatcctt    2760
caactcagca aaagttcgat ttattcaaca aagccgccgt cccgtcaagt cagcgtaatg    2820
ctctgccagt gttacaacca attaaccaat tctgattaga aaaactcatc gagcatcaaa    2880
tgaaactgca atttattcat atcaggatta tcaataccat atttttgaaa aagccgtttc    2940
tgtaatgaag gagaaaactc accgaggcag ttccatagga tggcaagatc ctggtatcgg    3000
tctgcgattc cgactcgtcc aacatcaata caacctatta atttcccctc gtcaaaaata    3060
aggttatcaa gtgagaaatc accatgagtg acgactgaat ccggtgagaa tggcaaaagc    3120
ttatgcattt ctttccagac ttgttcaaca ggccagccat tacgctcgtc atcaaaatca    3180
ctcgcatcaa ccaaaccgtt attcattcgt gattgcgcct gagcgagacg aaatacgcga    3240
tcgctgttaa aaggacaatt acaaacagga tcgaatgca accggcgcag gaacactgcc    3300
agcgcatcaa caatatttc acctgaatca ggatattctt ctaatacctg gaatgctgtt    3360
ttcccgggga tcgcagtggt gagtaaccat gcatcatcag gagtacggat aaaatgcttg    3420
atggtcggaa gaggcataaa ttccgtcagc cagtttagtc tgaccatctc atctgtaaca    3480
tcattggcaa cgctaccttt gccatgtttc agaaacaact ctggcgcatc gggcttccca    3540
tacaatcgat agattgtcgc acctgattgc ccgacattat cgcgagccca tttataccca    3600
tataaatcag catccatgtt ggaatttaat cgcggcctcg agcaagacgt ttcccgttga    3660
atatggctca taacacccct tgtattactg tttatgtaag cagacagttt tattgttcat    3720
gatgatatat tttatcttg tgcaatgtaa catcagagat tttgagacac aacgtggctt    3780 tcccccccc cccattattg aagcatttat cagggttatt gtctcatgag cggatacata    3840
tttgaatgta tttagaaaaa taaacaaata ggggttccgc gcacatttcc ccgaaaagtg    3900
ccacctgacg tctaagaaac cattattatc atgacattaa cctataaaaa taggcgtatc    3960
acgaggccct ttcgtctcgc gcgtttcggt gatgacggtg aaaacctctg acacatgcag    4020
ctcccggaga cggtcacagc ttgtctgtaa gcggatgccg ggagcagaca gcccgtcag    4080 ggcgcgtcag cgggtgttgg cgggtgtcgg gctggctta actatgcggc atcagagcag    4140
attgtactga gagtgcacca tatgcggtgt gaaataccgc acagatgcgt aaggagaaaa    4200
taccgcatca gattggctat                                               4220
```

<210> SEQ ID NO 10
<211> LENGTH: 4122
<212> TYPE: DNA
<213> ORGANISM: artificial sequence
<220> FEATURE:
<223> OTHER INFORMATION: synthetic oligonucleotide

<400> SEQUENCE: 10

```
tggccattgc atacgttgta tccatatcat aaatatgtaca tttatattgg ctcatgtcca     60
acattaccgc catgttgaca ttgattattg actagttatt aatagtaatc aattacgggg    120
tcattagttc atagcccata tatggagttc cgcgttacat aacttacggt aaatggcccg    180
```

```
cctggctgac cgcccaacga cccccgccca ttgacgtcaa taatgacgta tgttcccata    240
gtaacgccaa tagggacttt ccattgacgt caatgggtgg agtatttacg gtaaactgcc    300
cacttggcag tacatcaagt gtatcatatg ccaagtacgc cccctattga cgtcaatgac    360
ggtaaatggc ccgcctggca ttatgccag tacatgacct tatgggactt tcctacttgg     420
cagtacatct acgtattagt catcgctatt accatggtga tgcggttttg gcagtacatc    480
aatgggcgtg gatagcggtt tgactcacgg ggatttccaa gtctccaccc cattgacgtc    540
aatgggagtt tgttttggca ccaaaatcaa cgggactttc caaaatgtcg taacaactcc    600
gccccattga cgcaaatggg cggtaggcgt gtacggtggg aggtctatat aagcagagct    660
cgtttagtga accgtcagat cgcctggaga cgccatccac gctgttttga cctccataga    720
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctccaacggt    960
ggagggcagt gtagtctgag cagtactcgt tgctgccgcg cgcgccacca gacataatag   1020
ctgacagact aacagactgt tccttttcat gggtctttc tgcagtcacc gtcgtcgact    1080
gctgttgaca gtgagcgcgg cacaaatgat tgccaaatag tgaagccaca gatgtatttg   1140
gcagccattt gtgccttgcc tactgcctcg gaagcttaat aaaggatctt ttattttcat   1200
tggatctgtg tgttggtttt ttgtatgcgg ccgcggatcc agatcttttt ccctctgcca   1260
aaaattatgg ggacatcatg aagccccttg agcatctgac ttctggctaa taaggaaat    1320 ttattttcat tgcaatagtg tgttggaatt ttttgtgtct ctcactcgga aggacatatg   1380
ggagggcaaa tcatttaaaa catcagaatg agtatttggt ttagagtttg gcaacatatg   1440
cccattcttc cgcttcctcg ctcactgact cgctgcgctc ggtcgttcgg ctgcggcgag   1500
cggtatcagc tcactcaaag gcggtaatac ggttatccac agaatcaggg gataacgcag   1560
gaaagaacat gtgagcaaaa ggccagcaaa aggccaggaa ccgtaaaaag gccgcgttgc   1620
tggcgttttt ccataggctc cgcccccctg acgagcatca caaaaatcga cgctcaagtc   1680
agaggtggcg aaacccgaca ggactataaa gataccaggc gtttccccct ggaagctccc   1740
tcgtgcgctc tcctgttccg accctgccgc ttaccggata cctgtccgcc tttctccctt   1800
cgggaagcgt ggcgctttct catagctcac gctgtaggta tctcagttcg gtgtaggtcg   1860
ttcgctccaa gctgggctgt gtgcacgaac ccccgttca gcccgaccgc tgcgccttat    1920
ccggtaacta tcgtcttgag tccaacccgg taagacacga cttatcgcca ctggcagcag   1980
ccactggtaa caggattagc agagcgaggt atgtaggcgg tgctacagag ttcttgaagt   2040
ggtggcctaa ctacggctac actagaagaa cagtatttgg tatctgcgct ctgctgaagc   2100
cagttacctt cggaaaaaga gttggtagct cttgatccgg caaacaaacc accgctggta   2160
gcggtggttt ttttgtttgc aagcagcaga ttacgcgcag aaaaaagga tctcaagaag    2220 atcctttgat cttttctacg ggtctgacg ctcagtggaa cgaaaactca cgttaaggga    2280
ttttggtcat gagattatca aaaaggatct tcacctagat ccttttaaat taaaaatgaa   2340
gttttaaatc aatctaaagt atatatgagt aaacttggtc tgacagttac caatgcttaa   2400
tcagtgaggc acctatctca gcgatctgtc tatttcgttc atccatagtt gcctgactcg   2460 ggggggggg gcgctgaggt ctgcctcgtg aagaaggtgt tgctgactca taccaggcct   2520
gaatcgcccc atcatccagc cagaaagtga gggagccacg gttgatgaga gctttgttgt   2580
```

```
aggtggacca gttggtgatt ttgaactttt gctttgccac ggaacggtct gcgttgtcgg    2640
gaagatgcgt gatctgatcc ttcaactcag caaaagttcg atttattcaa caaagccgcc    2700
gtcccgtcaa gtcagcgtaa tgctctgcca gtgttacaac caattaacca attctgatta    2760
gaaaaactca tcgagcatca aatgaaactg caatttattc atatcaggat tatcaatacc    2820
atatttttga aaaagccgtt tctgtaatga aggagaaaac tcaccgaggc agttccatag    2880
gatggcaaga tcctggtatc ggtctgcgat tccgactcgt ccaacatcaa tacaacctat    2940
taatttcccc tcgtcaaaaa taaggttatc aagtgagaaa tcaccatgag tgacgactga    3000
atccggtgag aatggcaaaa gcttatgcat ttctttccag acttgttcaa caggccagcc    3060
attacgctcg tcatcaaaat cactcgcatc aaccaaaccg ttattcattc gtgattgcgc    3120
ctgagcgaga cgaaatacgc gatcgctgtt aaaaggacaa ttacaaacag gaatcgaatg    3180
caaccggcgc aggaacactg ccagcgcatc aacaatattt tcacctgaat caggatattc    3240
ttctaatacc tggaatgctg ttttcccggg gatcgcagtg gtgagtaacc atgcatcatc    3300
aggagtacgg ataaaatgct tgatggtcgg aagaggcata aattccgtca gccagtttag    3360
tctgaccatc tcatctgtaa catcattggc aacgctacct ttgccatgtt tcagaaacaa    3420
ctctggcgca tcgggcttcc catacaatcg atagattgtc gcacctgatt gcccgacatt    3480
atcgcgagcc catttatacc catataaatc agcatccatg ttggaattta atcgcggcct    3540
cgagcaagac gtttcccgtt gaatatggct cataacaccc cttgtattac tgtttatgta    3600
agcagacagt tttattgttc atgatgatat attttatct tgtgcaatgt aacatcagag    3660
attttgagac acaacgtggc tttccccccc cccccattat tgaagcattt atcagggtta    3720
ttgtctcatg agcggataca tatttgaatg tatttagaaa aataaacaaa tagggggttcc    3780 gcgcacattt ccccgaaaag tgccacctga cgtctaagaa accattatta tcatgacatt    3840
aacctataaa aataggcgta tcacgaggcc ctttcgtctc gcgcgtttcg gtgatgacgg    3900
tgaaaacctc tgacacatgc agctcccgga gacggtcaca gcttgtctgt aagcggatgc    3960
cgggagcaga caagcccgtc agggcgcgtc agcgggtgtt ggcgggtgtc ggggctggct    4020
taactatgcg gcatcagagc agattgtact gagagtgcac catatgcggt gtgaaatacc    4080
gcacagatgc gtaaggagaa aataccgcat cagattggct at                      4122
```

What is claimed is:

1. A method of suppressing a tumor cell growth in a human subject comprising the steps of:
   identifying the human subject in need for suppression of the tumor cell growth; and
   administering an expression vector in a therapeutic agent carrier complex to the human subject in an amount sufficient to suppress the tumor cell growth, wherein the expression vector expresses one or more shRNAs capable of inhibiting an expression of a target gene that is Stathmin 1 in the one or more target cells via RNA interference;
   wherein the one or more shRNAs comprise a bifunctional RNA molecule that activates a cleavage-dependent and a cleavage-independent RNA-induced silencing complex for reducing the expression level of the target gene;
   wherein the inhibition results in an apoptosis, an arrested proliferation, or a reduced invasiveness of the tumor cells.

2. The method of claim 1, wherein the therapeutic agent carrier comprises a bilamellar invaginated vesicle (BIV).

3. The method of claim 1, wherein the therapeutic agent carrier comprises one or more receptor targeting moieties that are small molecule bivalent beta-turn mimics.

4. The method of claim 1, wherein administering is selected from the group consisting of subcutaneous, intravenous, intraperitoneal, intramuscular, and intravenous injection.

5. The method of claim 1, wherein administering comprises intratumoral injection.

6. The method of claim 1, wherein administering comprises injecting with a DNA:lipoplex.

7. The method of claim 1, wherein the bifunctional RNA molecule targets at least one of the 5'-UTR or the 3'UTR of Stathmin-1.

8. The method of claim 1, wherein the bifunctional shRNA comprises a RNA sequence defined by DNA SEQ ID NO: 3.

9. The method of claim 1, wherein the bifunctional shRNA comprises a RNA sequence defined by DNA SEQ ID NO: 4.

10. The method of claim 1, wherein the bifunctional shRNA comprises a RNA sequence defined by DNA SEQ ID NO: 5.

11. The method of claim 1, wherein at least one target site sequence is within a Stathmin 1 gene cDNA sequence.

12. The method of claim 1, wherein at least one target site sequence is defined by SEQ ID NO: 1 or SEQ ID NO: 2.

13. The method of claim 1, wherein the therapeutic agent carrier is a compacted DNA nanoparticle.

14. The method of claim 13, wherein the DNA nanoparticle is compacted with one or more polycations.

15. The method of claim 14, wherein the one or more polycations is a 10 kDA polyethylene glycol (PEG)-substituted cysteine-lysine 3-mer peptide (CK30PEG10k).

16. The method of claim 13, wherein the compacted DNA nanoparticles are further encapsulated in a liposome.

17. The method of claim 1, wherein the therapeutic agent carrier is a liposome.

18. The method of claim 17, wherein the liposome is a reversibly masked liposome.

19. A method of suppressing a tumor cell growth in a subject comprising the steps of:
    identifying the human subject in need for suppression of the tumor cell growth; and
    administering a composition comprising an expression vector that expresses one or more shRNAs capable of inhibiting an expression of a target gene that is Stathmin 1 in the one or more target cells via RNA interference, and the shRNAs target at least one of the 5'-UTR, the coding region, or the 3'-UTR of the Stathmin-1, or overlapping portions thereof in a therapeutic agent carrier complex to the subject in an amount sufficient to suppress the tumor cell growth;
    wherein the one or more shRNAs comprise a bifunctional RNA molecule that activates a cleavage-dependent and a cleavage-independent RNA-induced silencing complex for reducing the expression level of the target gene;
    wherein the inhibition results in an apoptosis, an arrested proliferation, or a reduced invasiveness of the tumor cells.

20. The method of claim 19, wherein the therapeutic agent carrier comprises a bilamellar invaginated vesicle (BIV).

21. The method of claim 19, wherein the therapeutic agent carrier comprises one or more receptor targeting moieties that are small molecule bivalent beta-turn mimics.

22. The method of claim 19, wherein administering is selected from the group consisting of subcutaneous, intravenous, intraperitoneal, intramuscular, and intravenous injection.

23. The method of claim 19, wherein administering comprises intratumoral injection.

24. The method of claim 19, wherein administering the composition comprises injecting with a DNA:lipoplex.

25. The method of claim 19, wherein the bifunctional shRNA comprises a RNA sequence defined by at least one of DNA SEQ ID NO: 3, SEQ ID NO: 4, or SEQ ID NO: 5.

26. The method of claim 19, wherein at least one target site sequence is within a Stathmin 1 gene cDNA sequence.

27. The method of claim 19, wherein at least one target site sequence is defined by SEQ ID NO: 1 or SEQ ID NO: 2.

28. The method of claim 19, wherein the therapeutic agent carrier is a compacted DNA nanoparticle.

29. The method of claim 28, wherein the DNA nanoparticle is compacted with one or more polycations.

30. The method of claim 29, wherein the one or more polycations is a 10 kDA polyethylene glycol (PEG)-substituted cysteine-lysine 3-mer peptide (CK30PEG10k).

31. The method of claim 28, wherein the compacted DNA nanoparticles are further encapsulated in a liposome.

32. The method of claim 19, wherein the therapeutic agent carrier is a liposome.

33. The method of claim 32, wherein the liposome is a reversibly masked liposome.

* * * * *